US006747187B1

(12) United States Patent
Srivastava et al.

(10) Patent No.: US 6,747,187 B1
(45) Date of Patent: Jun. 8, 2004

(54) KNOCKOUT MOUSE FOR THE TUMOR SUPPRESSOR GENE ANX7

(75) Inventors: Meera Srivastava, Potomac, MD (US); Harvey B. Pollard, Potomac, MD (US)

(73) Assignee: Henry M. Jackson Foundation for The Advancement of Military Medicine, Rockville, MD (US)

(*) Notice: Subject to any disclaimer, the term of this patent is extended or adjusted under 35 U.S.C. 154(b) by 128 days.

(21) Appl. No.: 09/633,278

(22) Filed: Aug. 4, 2000

Related U.S. Application Data

(60) Provisional application No. 60/147,255, filed on Aug. 5, 1999.

(51) Int. Cl.$^7$ .................... A01K 67/027; A01K 67/033; C12N 15/00; C12N 5/00
(52) U.S. Cl. ................... 800/18; 800/3; 800/10; 800/25; 435/320.1; 435/354; 435/463
(58) Field of Search ................. 800/14, 3, 18, 800/25; 514/44; 424/93.2; 435/6, 325

(56) References Cited

PUBLICATIONS

Nieman, Transgenic Farm Animals get off the ground. Transgenic Research 7, 73–7 (1998) Chapman & Hall.*
Sigmund, Viewoint: Are Studies in Genetically Altered Mice Out of Control?, Arterioscler Thromb Vasc. Biol., Jun. 2000, pp 1425–1429.*
Cameron, Recent Advances in Transgenic Technology, Molecular Biotechnology, vol. 7, pp253–265.*
Satoh et al., Modulation of cell surface lectin receptors on K562 human erythtolrukrmis cells induced by transfection with annexin IV CDNA, A Satoh et al., FEBS Letters 405 (1997).*
L Mullins et al., J. Clin Invest.,"Perspectives Series: Molecular Medicine in Genetically Engineered Animals, "Apr. 1996, vol. 97, No. 7, pp. 1557–1560.*
A. Bradley et al., Bio/Technology, "Modifying the Mouse: Design and Desire," May 1992, vol. 10, pp. 534–539.*
K HS Campbell et al., Theriogenology, "Totipotency or Multipotentiality of Cultured Cells: Applications and Progress," Jan. 1997, vol. 47, Issue 1, pp.63–72.*
SL Eck et al., Gene Therapy, "Gene–based Therapy,"Chap. 5, pp. 77–101.*
E Marshall, Science, "Gene Therapy's Growing Pains," Aug. 1995, vol. 269, pp. 1050–1055.*
IM Verma et al., Nature, "Gene Therapy—promises, problems and prospects," Sep. 1997, vol. 389, pp. 239–242.*
AM Brownawell et al., Journal of Biological Chemistry, "Calcium–dependent Binding of Sorcin to the N–terminal Domain of Synexin (Annexin VII)," Aug. 1997, vol. 272, No. 35, pp. 22182–22190.*
A–M Gunteski–Hamblin et al., Am.J. Physiol.,"Annexin VI overexpression targeted to heart alters cardiomyocyte function in transgenic mice," 1996, 270:pp. H1091–H1100.*

CE Cruetz et al., Journal of cell science, "Effects of the expression of mammalian annexins in yeast secretory mutants,"Dec. 1992, 103, pp. 1177–1192.*
V Doring et al.,Journal of Biological Chemistry, "Dictyostelium Annexin VII(Synexin),"Sep. 1991, vol. 266, No. 26, pp. 17509–17515.*
Arbonés et al., "Gene Targeting in Normal Somatic Cells: Inactivation of the Interferon–γ Receptor in Myoblasts," *Nature Genetics*, vol. 6, pp. 90–97 (1994).
Babinet et al., "Genome Engineering Via Homologous Recombination in Mouse Embryonic Stem (ES) Cells: An Amazingly Versatile Tool for the Study of Mammalian Biology," *An. Acad. Bras. Cienc.*, vol. 73, pp. 365–383 (2001).
Charron et al., "High Frequency Disruption of the N–myc Gene in Embryonic Stem and Pre–B Cell Lines by Homologous Recombination," *Molecular and Cellular Biology*, pp. 1799–1804 (1990).
Coll et al., "Targeted Disruption of Vinculin Genes in F9 and Embryonic Stem Cells Changes Cell Morphology, Adhesion, and Locomotion," *Proc. Natl. Acad. Sci. USA*, vol. 92, pp. 9161–9165 (1995).
Doetschman et al., "Establishment of Hamster Blastocyst–Derived Embryonic Stem (ES) Cells," *Development Biology*, vol. 127, pp. 224–227 (1988).
Farese et al., "Modification of the Apolipoprotein B Gene in HepG2 Cells by Gene Targeting," *The Journal of Clinical Investigation*, vol. 90, pp. 256–261 (1992).
Itzhaki et al., "Construction by Gene Targeting in Human Cells of a 'Conditional' CDC2 Mutant that Rereplicates its DNA," *Nature Genetics*, vol. 15, pp. 258–265 (1997).
Itzhaki et al., "Targeted Breakage of a Human Chromosome Mediated by Cloned Human Telomeric DNA," *Nature Genetics*, vol. 2, pp. 283–287 (1992).
Itzhaki et al., "Targeted Disruption of a Human Interferon–Inducible Gene Detected by Secretion of Human Growth Hormone," *Nucleic Acids Research*, vol. 19, pp. 3835–3842 (1991).
Jasin et al., "Gene Targeting at the Human CD4 Locus by Epitope Addition," *Genes & Development*, vol. 4, pp. 157–166 (1990).
Kaiser, J., "Cloned Pigs M ay Help Overcome Rejection," *Science*, vol. 295, pp. 25–27 (2002).
Lai et al., "Production of α–1,3–Galactosyltransferase Knockout Pigs by Nuclear Transfer Cloning," *Sciencexpress*, Jan. 3, pp. 1–6 (2002).

(List continued on next page.)

*Primary Examiner*—Deborah Crouch
(74) *Attorney, Agent, or Firm*—Finnegan, Henderson, Farabow, Garrett & Dunner, L.L.P.

(57) ABSTRACT

A knockout transgenic mouse containing a nonfunctional allele of the tumor suppressing gene, annexin VII. This mouse is used as a screening model for potential therapeutic agents useful in the treatment of tumors resulting from an annexin tumor suppressor disease.

19 Claims, 33 Drawing Sheets

(2 of 33 Drawing Sheet(s) Filed in Color)

OTHER PUBLICATIONS

Manjunath et al., "Targeting Disruption of CD43 Gene Enhances T Lymphocyte Adhesion," *The Journal of Immunology*, vol. 151, pp. 1528–1534 (1993).

Montrose–Rafizadeh et al., "Gene Targeting of a CFTR Allele in HT29 Human Epithelial Cells," *Journal of Cellular Physiology*, Vo. 170, pp. 299–308 (1997).

Neimann et al., "Progress in Reproductive Biotechnology in Swine," Theriogenology, vol. 56, pp. 1291–1304 (2001).

Pain et al., "Long–term In vitro Culture and Characterization of Avian Embryonic Stem Cells with Multiple Morphogenetic Potentialities," *Development*, vol. 122, pp. 2339–2348 (1996).

Porter et al., "Gene Targeting in Human Somatic Cells: Complete Inactivation of an Interferon–Inducible Gene," *Eur. J. Biochem.*, vol. 218, pp. 273–281 (1993).

Shamblott et al., "Derivation of Pluripotent Stem Cells From Cultured Human Primordial Germ Cells," *Proc. Natl. Acad. Sci. USA*, vol. 95, pp. 13726–13731 (1998).

Shim et al., "Isolation of Pluripotent Stem Cells from Cultured Porcine Primordial Germ Cells," *Biology of Reproduction*, vol. 57, pp. 1089–1095 (1997).

Shirasawa et al., "Altered Growth of Human Colon Cancer Cell Lines Disrupted at Activated Ki–ras," *Science*, vol. 260, pp. 85–88 (1993).

Song et al., "Accurate Modification of a Chromosomal Plasmid by Homologous Recombination in Human Cells," *Proc. Natl. Acad. Sci. USA*, vol. 85, pp. 6820–6824 (1987).

Sukoyan et al., "Embryonic Stem Cells Derived From Morulae, Inner Cell Mass, and Blastocysts of Mink: Comparisons of Their Pluripotencies, *Molecular Reproduction and Development*," vol. 36, pp. 148–158 (1993).

Thomson et al., "Embryonic Stem Cell Lines Derived From Human Blastocysts," *Science*, vol. 282, pp. 1145–1147 (1998).

Thomson et al., "Isolation of a Primate Embryonic Stem Cell Line," *Proc. Natl. Acad. Sci. USA*, vol. 92, pp. 7844–7848 (1995).

Thomson et al., "Pluripotent Cell Lines Derived From Common Marmoset (*Callithrix jacchus*) Blastocysts[1]," *Biology of Reproduction*, vol. 55, pp. 254–259 (1996).

Vasquez et al., "Manipulating the Mammalian Genome by Homologous Recombination," *Proc. Natl. Acad. Sci. USA*, vol. 98, pp. 8403–8410 (2001).

Waldman et al., "p21 Is Necessary for the p53–Mediated $G_1$ Arrest in Human Cancer Cells," *Cancer Research*, vol. 55, pp. 5187–5190 (1995).

Wells, K., "Toward Knockout Sheep," *Nature Biotechnology*, vol. 19, pp. 529–530 (2001).

Wheeler, M., "Development and Validation of Swine Embryonic Stem Cells: A Review," *Reprod. Fertil. Dev.*, vol. 6, pp. 563–568 (1994).

Williams et al., "Rapid Detection of Homologous Recombinants in Nontransformed Human Cells," *Proc. Natl. Acad. Sci. USA*, vol. 91, pp. 11943–11947 (1994).

Yáñez et al., "Therapeutic Gene Targeting," *Gene Therapy*, vol. 5, pp. 149–159 (1998).

Zhen et al., "Gene Targeting of X Chromosome–Linked Chronic Granulomatous Disease Locus in a Human Myeloid Leukemia Cell Line and Rescue by Expression of Recombinant gp91$^{phox}$," *Proc. Natl. Acad. Sci. USA*, vol. 90, pp. 9832–9836 (1993).

Zheng et al., "Fidelity of Targeted Recombination in Human Fibroblasts and Murine Embryonic Stem Cells," *Proc. Natl. Acad. Sci. USA*, vol. 88, pp. 8067–8071 (1991).

Srivastava et al., "Low In Vivo Levels of Human ANX7 (Annexin VII) Gene Expression are Due to Endogenous Inhibitory Promoter Sequences," *Cell Biology International*, vol. 24, pp. 475–481 (2000).

Harvey B. Pollard, et al., "$Ca^{2+}$–activated synexin forms highly selective, voltage–gated $Ca^{2+}$ channels in phosphatidylserine bilayer membranes," Proc. Natl. Acad. Sci. USA, vol. 85, pp. 2974–2978 (1988).

Harvey B. Pollard, et al., "A Molecular Basis for Synexin–Driven, Calcium–Dependent Membrane Fusion," J. exp. Biol., vol. 139, pp. 267–286 (1988).

A. Lee Burns, et al., "Calcium channel activity of purified human synexin and structure of the human synexin gene," Proc. Natl. Acad. Sci. USA, vol. 86, pp. 3798–3802 (1989).

Rudolf Hauptmann, et al., "Vascular anticoagulant β: a novel human $Ca^{2+}$/phospholipid binding protein that inhibits coagulation and phospholipase $A_2$ activity: Its molecular cloning, expression and comparison with VAC–α," Eur. J. Biochem., vol. 185, pp. 63–71 (1989).

Harvey B. Pollard, et al., "Purification and Biochemical Assay of Synexin and of the Homologous Calcium Dependent Membrane–Binding Proteins, Endonexin II and Lipocortin I," in *Methods in Cell Biology*, vol. 31, pp. 207–227 (Alan M. Tartakoff, ed.) (1989).

A. Lee Burns, et al., "Human synexin (annexin VII) polymorphisms: tissue specificity and expression in *Escherichia coli*," Biochemical Society Transactions, vol. 18, No. 6, pp. 1118–1121 (1990).

Harvey B. Pollard, et al, "Synexin, a New Member of the Annexin Gene Family, is a Calcium Channel and Membrane Fusion Protein," in *Cytokines and Lipocortins in Inflammation and Differentiation*, pp. 159–172 (M. Melli and L. Paretne, eds.) (1990).

Harvey B. Pollard, et al, "Synexin (Annexin VII): A Cytosolic Calcium–Binding Protein which Promotes Membrane Fusion and Forms Calcium Channels in Artificial Bilayer and Natural Membranes," J. Membrane Biol., vol. 117, pp. 101–112 (1990).

Karin Magendzo, et al., "Alternative Splicing of Human Synexin mRNA in Brain, Cardiac, and Skeletal Muscle Alters the Unique N–terminal Domain," The Journal of Biological Chemistry, vol. 266, No. 5, pp. 3228–3232 (1991).

Harvey B. Pollard, et al., "Synexin: Molecular Mechanism of Calcium–Dependent Membrane Fusion and Voltage–Dependent Calcium–Channel Activity," Calcium Entry and Action at the Presynaptic Nerve Terminal, Annals of the New York Academy of Sciences, vol. 635, pp. 328–351 (1989).

M. Srivastava, et al., "HIV–1 Gag shares a signature motif with annexin (Anx7) which is required for virus replication," Proc. Natl. Acad. Sci. USA, vol. 96, pp. 2704–2709 (1999).

Tim E. Hawkins, et al., "Immunological Development of Cardiovascular Function Are Normal in Annexin VI Null Mutant Mice," Molecular and Cellular Biology, vol. 19, No. 12, pp. 8028–8032 (1999).

Meera Srivastava, et al., "Defects in inositol 1,4,5–triphosphate receptor expression, $Ca^{2+}$ signaling, and insulin secretion in the anx7(+/–) knockout mouse," Cell Biology, vol. 96, No. 24, pp. 13783–13788 (1999).

Harvey B. Pollard, et al., "Synexin (Annexin VII) Hypothesis for $Ca^{2+}$/GTP–Regulated Exocytosis," Catecholamines, *Advances in Pharmacology*, vol. 42, pp. 81–87 (P. Goldstein et al., eds.) (1988).

Tatsuya Okafuji, et al., "Antisense–mediated regulation of Annexin VII gene expression during the transition from growth to differentiation in *Dictyostelium discoideum*," Gene, vol. 189, pp. 49–56 (1997).

Amy B. Brownawell, et al., "Calcium–dependent Binding of Sorcin to the N–terminal Domain of Synexin (Annexin VII)," The Journal of Biological Chemistry, vol. 272, No. 35, pp. 22182–22190 (1997).

Meera Srivastava, et al., "Detection and Localization of Synexin (Annexin VII) in Xenopus Adult and Embryonic Tissues Using an Antibody to the Xenopus N–terminal PGQM Repeat Domain," Experimental Cell Research 229, pp. 14–19 (1996).

Meera Srivastava, et al., "Novel isoforms of synexin in *Xenopus Laevis:* multiple tandem PGQM repeats distinguish mRNAs in specific adult tissues and embryonic stages," Biochem. J., vol. 316, pp. 729–735 (1996).

Hung Caohuy, et al., "Membrane fusion protein synexin (annexin VII) as a $Ca^{2+}$/GTP sensor in exocytotic secretion," Proc. Natl. Acad. Sci. USA, vol. 93, pp. 10797–10802 (1996).

Volker Döring, et al., "The in vivo role of annexin VII (synexin): characterization of an annexin VII–deficient Dictyostelium mutant indicates an involvement in $Ca^{2+}$–regulated processes," Journal of Cell Science, vol. 108, pp. 2065–2076 (1995).

Stefan Selbert, et al., "Expression and localization of annexin VII (synexin) in muscle cells," Journal of Cell Science, vol. 108, pp. 85–95 (1995).

Anat Shirvan, et al., "Divergent Structure of the Human Synexin (Annexin VII) Gene and Assignment to Chromosome 10," Biochemistry, vol. 33, pp. 6888–6901 (1994).

Zhen–Yong Ahang–Keck, et al,. "Genomic organization and chromosomal localization of the mouse synexin gene," Biochem. J., vol. 301, pp. 835–835 (1994).

Patrick Raynal, et al., "Annexins: the problem of assessing the biological role for a gene family of multifunctional calcium– and phospholipid–binding proteins," Biochimica et Biophysica Acta, vol. 1197, pp. 63–93 (1994).

Zhen–Yong Ahang–Keck, et al., "Mouse synexin (annexin VII) polymorphisms and a phylogenetic cmparison with other synexins,"πBiochem. J., vol. 289, pp. 735–741 (1993).

Harvey B. Pollard, et al., "Synexin (annexin VII) and membrane fusion during the process of exocytotic secretion," Progress in Brain Research, Chapter 21, vol. 92, The Peptidergic Neuron, pp 247–255 (1991).

Harvey B. Pollard, et al., "Calcium channel and membrane fusion activity of synexin and other members of the Annexin gene family," Biophys. J., vol. 62, pp. 15–18 (1992).

Ko et al., "Molecular Therapy with Recombinant p53 Adenovirus in an Androgen–Independent, Metastic Human Prostate Cancer Model," *Human Gene Therapy*, vol. 7, pp. 1683–1691 (1996).

Raynal et al., "Cell Cycle and Post–Transcriptional Regulation of Annexin Expression in IMR–90 Human Fibroblasts," *Biochem. J.*, vol. 322, pp. 365–371 (1997).

Srivastava et al., "Novel Isoforms of Synexin in Xenopus Laevis: Multiple Tandem PGQM Repeats Distinguish MRNAs in Specific Adult Tissues and Embryonic Stages," *Biochem. J.*, vol. 316, pp. 729–735 (1996).

Srivastava et al., "ANX7, a Candidate Tumor Suppressor Gene for Prostate Cancer," *PNAS*, vol. 98, pp. 4575–4580 (2001).

* cited by examiner

*FIG. 5C* BROWN GERM-LINE HETEROZYGOTE
*FIG. 5B* STRIPED CHIMERA
*FIG. 5A* BLACK FEMALE

FIG. 9A    FIG. 9B
FIG. 10A    FIG. 10B

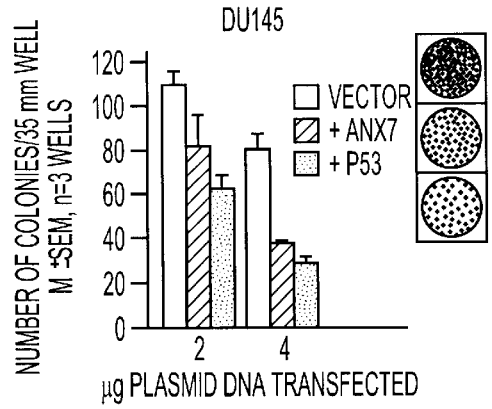 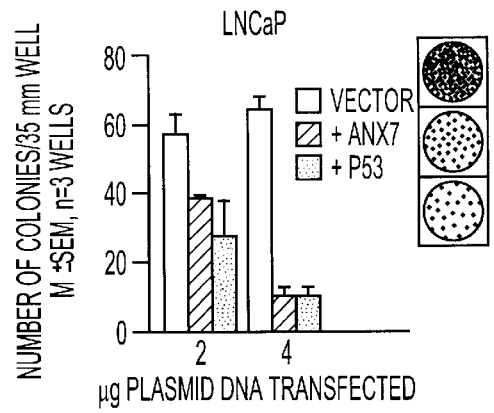
FIG. 12A  FIG. 12B
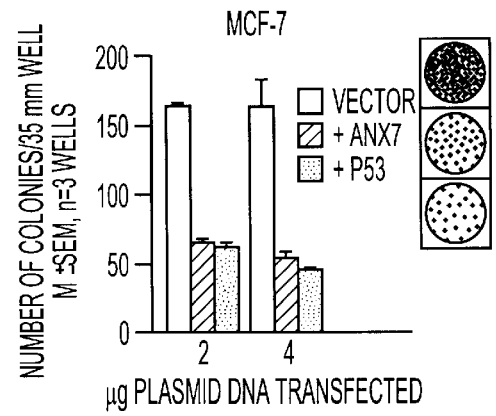 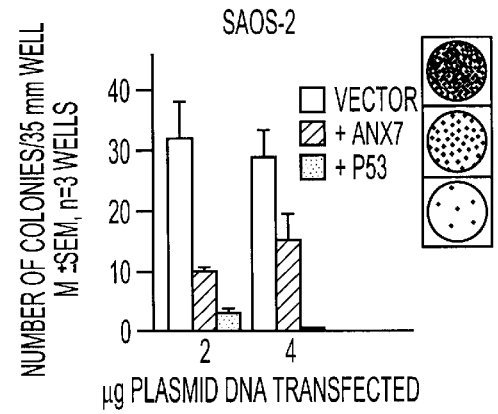
FIG. 12C  FIG. 12D

SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 1
cggatcgatc ccctcagaag aac                                                23

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (2)
<223> OTHER INFORMATION: Variable amino acid

<400> SEQUENCE: 2

Gly Xaa Gly Thr Asp Glu
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (2)
<223> OTHER INFORMATION: Variable amino acid

<400> SEQUENCE: 3

Gly Xaa Gly Thr Asn Gln
 1               5

<210> SEQ ID NO 4
<211> LENGTH: 13
<212> TYPE: PRT
<213> ORGANISM: Homo sapiens

<400> SEQUENCE: 4

Arg Asp Leu Glu Lys Asp Ile Arg Ser Asp Thr Ser Gly
 1               5                   10

KNOCKOUT MOUSE FOR THE TUMOR SUPPRESSOR GENE ANX7

This application claims the right to priority based on Provisional Patent Application No. 60/147,255, filed Aug. 5, 1999.

FIELD OF THE INVENTION

The invention is directed to tumor-susceptible non-human animals. The invention further pertains to the use of such animals in the development of anti-cancer agents and therapies.

BACKGROUND

Cancer is a set of diseases resulting from uncontrolled cell growth, which causes intractable pain and death for more than 300,000 people per year in the United States alone. Oncogenes and tumor suppressor genes are at opposite ends of a spectrum of gene actions that either promote or retard cancer cell growth. The development of cancer is believed to depend on the activation of oncogenes and the coincident inactivation of growth suppressor genes (Park, M., "Oncogenes" in *The Genetic Basis of Human Cancer* (B. Vogelstein et al., eds.) pp. 205–228 (1998)). Oncogenes are mutated, dominant forms of cellular proto-oncogenes that stimulate cell proliferation, while tumor suppressor genes are recessive and normally inhibit cell proliferation (Cooper, 1995). The loss or inactivation of tumor suppressor genes is widely thought to be one of the contributors to unregulated cancer cell growth. While the discovery and identification of oncogenes has been relatively straightforward, identifying tumor suppressor genes has been much less so (Fearon, *The Genetic Basis of Human Cancer* (B. Vogelstein et al., eds.) pp. 229–236 (1998)).

Both oncogenes and tumor-suppressing genes have a basic distinguishing feature. The oncogenes identified thus far have arisen only in somatic cells and thus have been incapable of transmitting their effects to the germ line of the host animal. In contrast, mutations in tumor-suppressing genes can be identified in germ line cells and are thus transmissible to an animal's progeny. About a dozen such tumor suppressor genes have been identified, with the hope that knowledge of their mechanism(s) might yield therapeutically relevant insights.

Tumor suppressor gene action depends on either mutation or deletion of both tumor suppressor alleles or on a reduction in the absolute level of expressed tumor suppressor protein. In their natural state, tumor suppressor genes act to suppress cell proliferation. Damage in such genes leads to a loss of this suppression, and thereby results in tumorigenesis. Knudson's "two-mutation hypothesis" is a well studied statistical model for tumor suppressor gene action which is based on the epidemiological analysis of retinoblastoma. (Knudson, A. G., *Proc. Nat. Acad. Sci. USA.* 68:820–823 (1971)). According to this model, the host is heterozygous for the tumor suppressor gene, and cancer ensues when the single remaining functional allele also mutates to create a nullizygous state. An alternative model is the "haplo-insufficient hypothesis" in which the tumor cell produces abnormally low levels of wild type tumor suppressor gene product. Thus, in both of these models the deregulation of cell growth may be mediated by the inactivation of tumor-suppressing genes (Weinberg, R. A., Scientific Amer., September 1988, pp 44–51).

Tumor suppressor genes are principally known for control of cell proliferation by their action on the cell cycle. Well-studied examples include Rb (Weinberg, R. A., *Cell,* 81:323–330 (1996)), p53 (Greenblatt, M. S. et al., *Cancer Res.* 54:4855–4878, (1994); Williams, B. O. et al., *Cold Spring Harbor Symp. Quant. Biol.* 59:449, (1994)); Levine, A. J., *Cell* 88:323–331 (1997)), and p16 (Cairns, P., et al., *Nat. Genetics* 11:210–212, (1995)); Okamoto, A., et al., *Cancer Research* 55:1448–1451, (1995)). Another example of a tumor suppressor gene acting on the cell cycle is the $p27^{KIP1}$ gene, also known simply as p27, which physiologically inhibits cyclin-dependent kinases, and thereby blocks cell proliferation (Fero, M. L., et al., *Nature* 396:177–180 (1998)).

In understanding how tumor suppressor genes impact the cell cycle, one must understand that cell cycle transitions are regulated by specific cyclin dependent kinases that consist of an activating cyclin subunit and a catalytic Cdk subunit (Polyak, K., et al., *Cell* 78:59–66 (1994)); Hartwell, L., *Cell* 71:543–546, (1992)); Nurse, P., *Nature* 344:503–508, (1990)). The functions of the respective cyclins and Cdk's in mammalian cells correspond to the different phases of the cell cycle. For example, during the G1 phase, cyclin D-Cdk4/6 and cyclin E-Cdk2 are catalytically active and rate limiting for cell cycle progression. Growth factors induce the synthesis of D-type cyclins to initiate the G1 phase. The D-type cyclins then associate with Cdk4/Cdk6, and the active Cdk's then hyperphosphorylate Rb to drive the cell past the restriction point (Buchkovich, K., et al., *Cell* 58:1097–1105 (1989)); see Weinberg, R. A., *Cell* 81:323–330 (1996)). Tumor suppressor genes have been found to affect the function of both of these types of subunits.

In addition to the cell cycle, tumor suppressor genes can also control cellular differentiation by acting as transcription factors and/or by modulating specific downstream DNA repair targets involved in maintaining genomic integrity. In this class, the tumor suppressor gene, inactivation of the tumor suppressor gene, p53, is the most common, resulting in a somatic mutation that causes malignancy (Nigro, J. M., et al., *Nature* 342:705–708 (1989); cf, review by Nguyen and Jameson, 1998). Of particular note, p53 is a frequent target for mutation in lung cancer (Takahashi, R., et al., *Science* 246:491–494 (1989)) and bladder cancers (Sidransky, D., et al., *Science* 252:706–709 (1991)). A germlne mutation for p53 is the basis for a familial cancer, the Li-Fraumeni syndrome (Srivastava, S., et al., *Nature* 348:747–749 (1990)). At the level of DNA repair, p53 works in the following manner: When DNA is damaged, a resulting signal causes stabilization of p53, which in turn causes transcriptional deregulation of p21, resulting in cell cycle arrest in the G1 phase (Hunter, T., *Cell* 75:839–841 (1993)).

Finally, tumor suppressor genes have also been implicated in controlling apoptotic cell death (Graeber, T. G., et al., *Nature* 379:88 (1996)). Again, p53 figures prominently in this process as well (Basu, A., et al., *Mol. Hum. Reprod.* 4:1099–1109 (1998)). The clear message from this brief summary is that the individual tumor suppressor genes cannot be viewed from a single perspective.

In order to study these tumor suppressor genes, model systems must be developed. Recent advances in recombinant DNA and genetic technologies have made it possible to discover and assess new tumor suppressor genes. One of the key model systems available is the transgenic animal. Such animals have been engineered to contain gene sequences that are not normally or naturally present in an unaltered animal. The techniques have also been used to produce animals which exhibit altered expression of naturally present gene sequences.

There remains a need for additional transgenic animals and methods of generating such animals, for the discovery of new tumor-suppressor genes.

SUMMARY OF THE INVENTION

The present invention provides a transgenic knockout mammal having somatic and germline cells comprising a chromosomally incorporated transgene. At least one allele of a genomic tumor suppressing annexin gene is disrupted by the transgene such that the expression of a tumor suppressing annexin gene is inhibited. This inhibition of the endogenous tumor suppressing annexin gene results in an increased susceptibility to formation of tumors as compared to a wild type mammal. The transgenic mammal may be heterozygous for this disruption. Preferably, the genomic tumor suppressing annexin gene is annexin VII. The preferred transgenic mammal is a transgenic rodent, and the more preferred transgenic mammal is a mouse.

Another embodiment of this method is the generation of transgenic embryonic stem cells. The method involves the steps of:

(a) constructing a transgene construct containing
  (i) a recombination region having all or a portion of the endogenous tumor suppressing annexin gene and
  (ii) a marker sequence which provides a detectable signal for identifying the presence of the transgene in a cell;
(b) transferring the transgene into embryonic stem cells of a mammal; and
(c) selecting embryonic stems cells having a correctly targeted homologous recombination between the transgene construct and the tumor suppressing annexin gene.

Another embodiment of the present invention comprises a method for generating a transgenic mammal having a functionally disrupted endogenous tumor suppressing annexin gene. The method involves the steps of:

(a) constructing a transgene construct containing
  (i) a recombination region having all or a portion of the endogenous tumor suppressing annexin gene and
  (ii) a marker sequence which provides a detectable signal for identifying the presence of the transgene in a cell;
(b) transferring the transgene into embryonic stem cells of a mammal;
(c) selecting embryonic stems cells having a correctly targeted homologous recombination between the transgene construct and the tumor suppressing annexin gene;
(d) transferring the cells of step (c) into a blastocyst and implanting the resulting chimeric blastocyst into a female mammal, and
(e) selecting those offspring harboring an endogenous tumor suppressing annexin gene allele comprising the correctly targeted recombination.

The preferred transgenic mammal for this method is a transgenic rodent, and the more preferred transgenic mammal is a transgenic mouse. The most preferred transgenic stem cell is a transgenic mouse stem cell. The most preferred tumor suppressing annexin gene is an annexin VII gene.

Another embodiment of the invention comprises a method for evaluating the carcinogenic potential of a test agent by contacting a transgenic mammal containing a disrupted tumor suppressing annexin gene with a test agent, and comparing the number of transformed cells in a sample of the treated transgenic mammal with the number of transformed cells in a sample from an untreated transgenic mammal. Alternatively, one can compare the number of transformed cells in a sample of the treated transgenic mammal with a control agent. The difference in the number of transformed cells in the treated transgenic mammal, compared to the number of transformed cells in the absence of treatment or in the presence of a control agent, indicates the carcinogenic potential of the test agent.

Another embodiment comprises a method of treating mammalian cancer cells lacking endogenous wild-type annexin protein, which comprises introducing a wild-type annexin tumor suppressor gene into the mammalian cancer cells, whereby the phenotype of abnormal proliferation of these mammalian cancer cells' is suppressed by the expressed annexin protein. Preferably, the mammalian cancer cell lacks at least one allele of the wild-type annexin tumor suppressor gene. Preferably, the mammalian cancer cell is an osteosarcoma cell, lung carcinoma cell, lymphoma cell, leukemia cell, soft-tissue sarcoma cell, breast carcinoma cell, bladder carcinoma cell, or prostate carcinoma cell. More preferably, the mammalian cancer cell has a mutated annexin tumor suppressor gene.

Another embodiment comprises a method for treating a patient having a neoplasm characterized by abnormally proliferating cells in a mammal comprising administering an effective dose of a recombinant replication deficient virus comprised of a DNA segment that expresses a protein having the cell growth inhibition activity of the annexin tumor suppressor gene product. In one embodiment, the patient has a neoplasm comprised of cells that substantially lack a functional annexin tumor suppressor gene product. In another preferred embodiment, the neoplasm is comprised of cells that substantially lack a functional annexin VII gene product. Preferably, the replication-deficient virus is selected from the group consisting of a retrovirus, an adenovirus, a herpes simplex virus, a vaccinia virus, a papillomavirus, and an adeno-associated virus. Most preferably, the virus is a recombinant replication deficient adenovirus expression vector.

Another embodiment comprises a composition for therapy of a neoplastic disease characterized by the lack a functional annexin tumor suppressor gene product. The treatment comprises administering a therapeutically effective dose of a recombinant replication deficient adenovirus in a pharmaceutically deliverable form.

Another embodiment comprises a method of treating a disease characterized by abnormally proliferating cells in a mammal, by:

(a) administering an expression vector coding for an annexin protein to the mammal,
(b) inserting the expression vector into the abnormally proliferating cells, and
(c) expressing the tumor suppressor annexin gene in the abnormally proliferating cells in an amount effective to suppress proliferation of those cells.

Another embodiment is a DNA construct containing a recombination region having all or a portion of the endogenous tumor suppressing annexin gene and a marker sequence which provides a detectable signal for identifying the presence of the transgene in a cell. Preferably, the construct is KSBX.pPNT, as described below.

Another embodiment comprises a cell containing the DNA construct mentioned above. More preferably, the cell is a tumor cell, and most preferably, the cell is a mammalian cancer cell lacking endogenous wild-type annexin protein. In another preferable embodiment, the construct is KSBX-.pPNT.

Another embodiment is an expression vector comprising an isolated polynucleotide sequence, which hybridizes to an annexin sequence under standard hybridization conditions and encodes a protein having the cell growth inhibition activity of an annexin protein. Preferably, the expression vector is selected from the group consisting of a retrovirus, an adenovirus, a herpes simplex virus, a vaccinia virus, a papillomavirus, and an adeno-associated virus. More preferably, the expression vector is a recombinant replication deficient adenovirus, and the polynucleotide sequence corresponds to the annexin VII gene.

Another embodiment comprises a cell transformed by the expression vector mentioned above.

Another embodiment comprises a method for identifying a polymorphism or a mutation in an exon of a human or animal tumor suppressor annexin VII gene. This method involves:
  (a) incubating, under amplification conditions, a sample of genomic DNA comprising an exon of a human or animal tumor suppressor annexin gene with a primer pair comprising:
    (i) a first primer which hybridizes to a promoter region or to an intron upstream of the exon, and
    (ii) a second primer which hybridizes to the 3'-noncoding region or to an intron downstream of the exon, such that at least one primer of the primer pair hybridizes to an intron;
  (b) producing an amplification product;
  (c) determining the nucleotide sequence of the amplification product of the exon; and
  (d) comparing the sequence of the exon obtained in step
    (b) to the sequence of a corresponding wild type exon.
A polymorphism or mutation is identified as a difference between these two sequences. Preferably, the exon is selected from the group consisting of exon 4, exon 5, exon 6, exon 7, and exon 8.

Another embodiment comprises a pharmaceutical preparation comprising an expression vector comprising an isolated polynucleotide sequence, which hybridizes to an annexin sequence under standard hybridization conditions and that encodes a protein having the cell growth inhibition activity of annexin VII, and a physiologically tolerable diluent.

BRIEF DESCRIPTION OF THE FIGURES

The file of this patent contains at least one drawing executed in color. Copies of this patent with color drawings will be provided by the Patent and Trademark Office upon request and payment of the necessary fee.

FIG. 5A illustrates a recipient nonagouti (a/a) (black female) C57B1/6 blastocyst.

FIG. 5B illustrates the synexin transgenic chimeric mouse generated by injecting ES cells (with targeting construct) derived from an agouti (A/A) mouse (brown).

FIG. 5C illustrates the all agouti progeny from this chimeric mouse, when bred to a C57B1/6 black male or C57B1/6 black female.

FIG. 9A. Metastatic Lymphosarcoma of the thymus stained with hematoxylin and eosin (H and E) from a control littermate of an anx7 (+/−) mouse.

FIG. 9B. Metastatic Lymphosarcoma of the thymus stained with hematoxylin and eosin (H and E) from an anx7 (+/−) mouse.

FIG. 10A. Lymphosarcoma of the thymus metastatic to the lung from a control littermate of an anx7 (+/−) mouse.

FIG. 10B. Lymphosarcoma of the thymus metastatic to the lung from anx7 (+/−) mouse.

FIG. 12A. Growth suppression of tumor cells by anx7 and p53 in DU145, a prostate tumor cell line, transfected with pcDNA3.1 alone (vector) or vector expressing anx7 (+anx7) or p53 (+p53).

FIG. 12B. Growth suppression of tumor cells by anx7 and p53 in LNCaP, a prostate tumor cell line, transfected with pcDNA3.1 alone (vector) or vector expressing anx7 (+anx7) or p53 (+p53).

FIG. 12C. Growth suppression of tumor cells by anx7 and p53 in MCF-7, a breast cancer cell line, transfected with pcDNA3.1 alone (vector) or vector expressing anx7 (+anx7) or p53 (+p53).

FIG. 12D. Growth suppression of tumor cells by anx7 and p53 in Saos, an osteosarcoma cell line, transfected with pcDNA3.1 alone (vector) or vector expressing anx7(+anx7) or p53 (+p53).

DETAILED DESCRIPTION

Figure 1A:
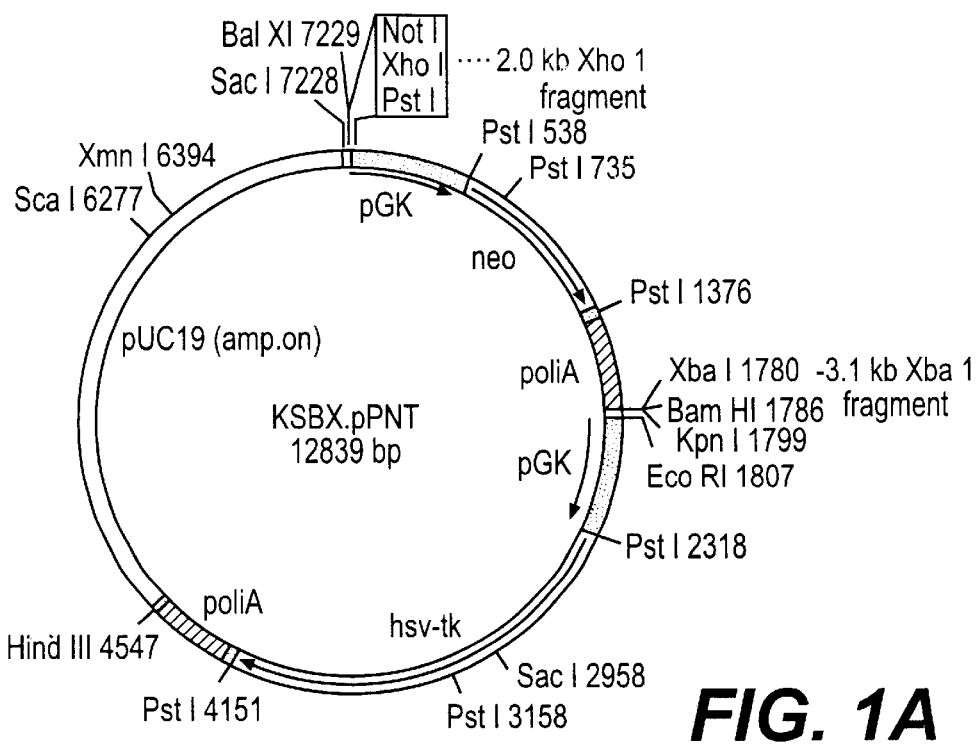
FIG. 1A depicts the targeting vector, KSBX.PPNT.
Figure 1B:
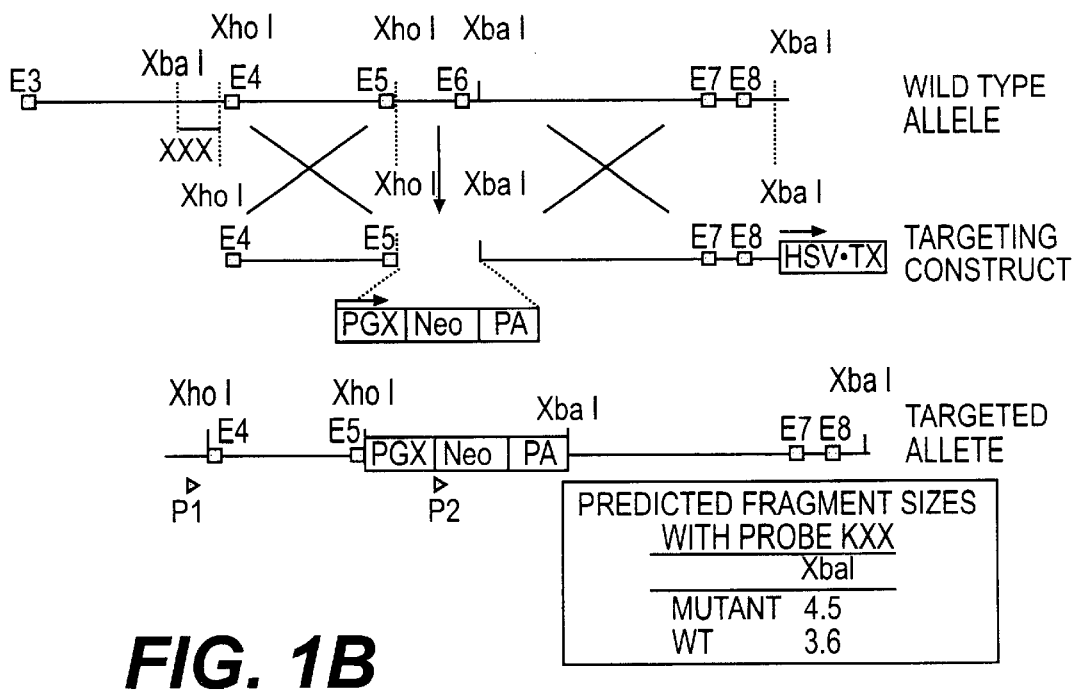
FIG. 1B depicts the restriction map of the mouse anx7 gene.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); and Manipulating the Mouse Embryo, (Cold Spring Harbor Laboratory Press, Cold Spring Harbor, N.Y., 1986).

I. Definitions

As is well known, the cells of humans and animals (especially, rodents (i.e. mouse, rat, hamster, etc.), rabbits, sheep, goats, fish, pigs, cattle and non-human primates) are "diploid" cells, and thus naturally contain two copies ("alleles") of each and every gene of their genome. A cell's "genome" consists of all of its heritable DNA (either chromosomal or non-chromosomal (i.e. episomal, viral, etc.). One of the two alleles of a gene is provided by the animal's or cell's maternal parent; the other set is provided by its paternal parent. The diploid nature of human and animal cells is described by Lewin, B. (Genes V, Oxford Univ. Press, New York (1994)), and in other similar treatises.

When a cell has two identical or substantially similar alleles of a gene, it is said to be "homozygous." In contrast, when the cell has two substantially different alleles it is said to be "heterozygous" for that gene. If both alleles are nonfunctional, then the cell is said to be "nullizygous."

An allele may be capable of being expressed by the natural processes operating in a cell. The expression of an allele results in the production of a gene product. The term "allele" as used herein is intended to denote any nucleotide sequence that affects the expression of a particular gene. It thus is intended to refer to any enhancer, promoter, processing, intervening, coding or termination sequence or region of the gene, or any sequence that stabilizes the gene product, or its mRNA, etc.

An allele of a gene is said to be "mutated" if (1) it is not expressed in a cell or animal, (2) the expression of the allele is altered with respect to the expression of the normal allele of the gene, or (3) the allele expresses a gene product, but that gene product has altered structure, activity, or characteristics relative to the gene product of a normal allele of that gene.

Thus, the terms "mutation" or "mutated" as used herein are intended to denote an alteration in the "normal" or "wild-type" nucleotide sequence of any nucleotide sequence or region of the allele. As used herein, the terms "normal" and "wild-type" are intended to be synonymous, and to denote any nucleotide sequence typically found in nature. The terms "mutated" and "normal" are thus defined relative to one another; where a cell has two chromosomal alleles of a gene that differ in nucleotide sequence, at least one of these alleles is a "mutant" allele as that term is used herein. Based on these definitions, an "endogenous tumor suppressing gene" is the "wild-type" tumor suppressing gene that exists normally in a cell, and a "mutated annexin tumor suppressor gene" defines a gene that differs in nucleotide sequence from the wild-type gene.

Mutations may have one of three effects. One effect is that a mutation may detectably alter the expression of an allele. This denotes any change in nucleotide sequence affecting the extent to which the allele is transcribed, processed or translated. Such alterations may be, for example, in (1) an enhancer, (2) a promoter, (3) a coding or termination region of the allele, (4) a mutation which stabilizes the gene product, or its mRNA, etc.

A second effect is that a mutation may detectably alter the activity of an allele. This denotes any change in nucleotide sequence that alters the capacity of the expressed gene product to mediate a function of the gene product. Such mutations include changes that diminish or inactivate one or more functions of the expressed product. Significantly, such mutations also include changes that result in an increase in the capacity of the gene product to mediate any function (for example, a catalytic or binding activity) of that gene product.

Third, a mutation may detectably alter the function of an allele. This denotes any change in nucleotide sequence that alters the capacity of a binding molecule (such as a binding protein) to specifically bind to the allele.

The mutations that cause these effects in a tumor suppressing annexin gene can be readily identified by sequencing, tumorigenicity, resilience to tumorigenicity, binding activity, etc. (see, for example, Eliyahu et al., Nature 312:646–649 (1984); Finlay et al., Molec. Cell. Biol. 8:531–539 (1988); Nigro, J. M. et al., Nature 342:705–708 (1989), all herein incorporated by reference).

An allele is said to be "chromosomal" if it either is, or replaces, one of the two alleles of a gene which a cell inherits from its ancestors, or which an animal inherits from its parents. An allele is not "chromosomal," as that term is used herein, if the allele increases the copy number of the total number of alleles of a particular gene which are present in a cell.

The cells that can be produced in accordance with the present invention include both "germ-line" and "somatic" cells. A "germ-line" cell is a sperm cell or egg cell, or a precursor or progenitor of either; such cells have the potential of transmitting their genome (including the altered tumor-suppressor allele) in the formation of progeny animals. A "somatic" cell is a cell that is not a germ-line cell.

As used herein, the term "transgene" refers to a nucleic acid sequence which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can be operably linked to one or more transcriptional regulatory sequences and any other nucleic acid, such as introns, that may be necessary for optimal expression of a selected nucleic acid. Exemplary transgenes of the present invention encode, for instance an annexin polypeptide, preferably an ANX7-polypeptide. Other exemplary transgenes are directed to disrupting one or more genomic annexin genes by homologous recombination with genomic sequences of an annexin gene, preferably an anx7 gene.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). The line(s) used to practice this invention may themselves be transgenics, and/or may be knockouts (i.e., obtained from animals which have one or more genes partially or completely suppressed).

The transgene construct may be introduced into a single stage embryo. The zygote is the best target for microinjection. The use of zygotes as a target for gene transfer has a major advantage in that in most cases the injected DNA will be incorporated into the host gene before the first cleavage (Brinster et al. (1985) PNAS 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, the exogenous genetic material should be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Any technique which allows for the addition of the exogenous genetic material into nucleic genetic material can be utilized so long as it is not destructive to the cell, nuclear membrane, or other existing cellular or genetic structures. Introduction of the transgene nucleotide sequence into the embryo may be accomplished by any means known in the art such as, for example, microinjection, electroporation, or lipofection. The exogenous genetic material is preferentially inserted into the nucleic genetic material by microinjection. Microinjection of cells and cellular structures is known and is used in the art. In the mouse, the male pronucleus reaches the size of approximately 20 micrometers in diameter which allows reproducible injection of 1–2pl of DNA solution. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of an ANX7 protein (either agonistic or antagonistic), the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) PNAS 73:1260–1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927–6931; Van der Putten et al. (1985) PNAS 82:6148–6152). Transfection is easily and efficiently obtained by culturing the blastomeres on a monolayer of virus-producing cells (Van der Putten, supra; Stewart et al. (1987) EMBO J. 6:383–388). Alternatively, infection can be performed at a later stage. Virus or virus-producing cells can be injected into the blastocoele (Jahner et al. (1982) Nature 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES) and is the preferred method of this invention. ES cells are obtained from pre-implantation embryos cultured in vitro and fused with embryos (Evans et al. (1981) Nature 292:154–156; Bradley et al. (1984) Nature 309:255–258; Gossler et al. (1986) PNAS 83:9065–9069; and Robertson et al. (1986) Nature 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240:1468–1474.

II. The Invention

Using any of the methods described above, the present invention relates to the production of non-human transgenic and chimeric animals and cells which contain at least one mutated chromosomal allele of a tumor suppressor gene. The present invention encompasses the formation of such cells and non-human animals for any annexin tumor suppressor gene. The invention is illustrated below with reference to the annexin VII tumor suppressor gene, but this example is not meant to limit the scope of the invention. The ability to manipulate this gene and to produce non-human transgenic animals which carry such mutated alleles is illustrated with respect to a particular disrupted allele. It is to be understood, however, that the invention and the methods disclosed herein can be used to produce any possible mutation in the anx7 gene. In particular, the invention includes the production of animal cells and non-human transgenic or chimeric animals which carry the particular mutations of the anx7 gene that are responsible for the lethal nullizygous state discussed below.

The nullizygous anx7 (−/−) transgenic mouse mutant has a lethal phenotype during early embryogenesis. However, the heterozygous anx7 (+/−) transgenic mouse exhibits a phenotype of gender dimorphic gigantism, generalized organomegaly, focal hyperplasia and dysplasia, and increased incidence of disparate spontaneous tumors. The combination of dysplasia and increased incidence of tumors was the first hint that the anx7 gene may be a tumor suppressor gene. As a preliminary direct test of tumor suppressor activity, the wild type human anx7 gene was transfected into two human prostate tumor cell lines, a breast cancer cell line, and an osteosarcoma cell line. The experiments with the anx7 gene systematically result in tumor cell growth arrest, as did the positive controls with the wild type p53 gene. It was therefore concluded that the anx7 is a tumor suppressor gene. The loss (either by mutation or deletion) of both anx7 alleles has been found to be an embryonic lethal event.

III. The Annexin Genes and Specifically, the Annexin VII Gene (anx 7)

The present invention concerns a non-human animal or an animal (including human) cell in which one of the two naturally present copies of an annexin gene, preferably the anx7 gene, of such non-human animal or animal cell has been rendered non-functional through a mutation (such as a deletion, insertion, or substitution in the naturally occurring annexin gene sequence).

A. General Properties of Annexins

Annexins are a family of structurally related proteins that all have the ability to bind $Ca^{2+}$ and phospholipid. These genes have been described in many organisms from mammals to molds to plants. (Raynal and Pollard, BBA 1197:63–93 (1994)). In the presence of $Ca^{2+}$, the annexins bind to acidic phospholipids with very high affinity ($K_d$ in the nM range for annexin V.) The $Ca^{2+}$ binding similarities of all the annexins is due to their common primary structure, a unique N-terminal domain (the 'tail') and a conserved C-terminal domain (the 'core'). With the exception of annexin VI, the conserved C-terminal domain is always composed of 4 repeats (annexin VI having 8) of ~70 amino acids containing an increased homology region called the "endonexin fold". Due to this conserved primary structure, all annexins have a high degree of identity with each other. Within mammals, annexins have between 40% and 60% identity with any other member of the family. (Hauptmann, R. et al. *Eur. J. Biochem.* 185:63–71 (1989)).

B. Molecular Biology of Annexins

Genomic analysis performed on annexins I, II, III, and VII showed striking similarities in the organization of these annexin genes. For annexins I, II, and III, the location of exon-intron boundaries is very well conserved in the core domain. However, comparison of the genomic structure of the anx7 gene with other annexins showed that only five of the 10 splice junctions in the core domain were conserved. These findings suggest that annexin genes may derive from a common ancestor gene, but that a precursor underwent divergent remodeling during its evolution towards annexins I, II, and III, on the one hand, and anx7 on the other. There is no apparent relationship between the exon-intron organization of annexin genes and the primary structure of the their respective proteins.

C. Annexins as Tumor Suppressor Genes

Recently attention has been directed towards the family of annexin genes, particularly the anx7 gene (a.k.a. synexin), as tumor suppressor gene candidates. Early work on the anx7 gene has shown that it is expressed in small amounts in nearly every cell (Creutz, E. C., et al., *J. Biol. Chem.* 254:553–558 (1978); ibid, 1979; Raynal and Pollard, *BBA Biomembranes* 1197:63–93(1994)). In fact, anx7 is found throughout phylogeny as a single copy gene in organisms as diverse as man (Shirvan, A., et al., *Biochemistry* 33:6888–6901 (1994)), mouse (Zhang-Keck, Z-Y., et al., *Biochem. J.* 289: 735–741 (1993), Zhang-Keck, Z-Y., et al., *Biochemical J.* 301:835–845 (1994), Xenopus (Srivastava, S., et al., *Biochemical J.* 316:729–736 (1996)), and Dictyostelium (Greenwood, M., et al., *Biochim Biophys Acta* 1088(3):429–32 (1991); Doring, V., et al., *J. Biol. Chem.* 266:17509–17515 (1991); Gierke, V., et al., *J Biol. Chem.* 226:1697–1700(1991)).

D. Annexin VII

In man, the anx7 gene is found on chromosome 10q21. Other potential tumor suppressor genes have been hypothesized to exist on chromosome 10q in the same vicinity as the anx7gene. Examples include myxoid chondrosarcoma at 10q21.1 (Shen, W. P., et al., *Cancer Genet Cytogenet.*

45:207–215 (1990)); sporadic nonmedullary thyroid carcinoma at 10q21.1 (Jenkins, R. B., et al., *Cancer* 66:1213–1220 (1990)); renal cell carcinoma at 10q21–23 (Morita, R., et al., *Cancer Res.* 51:5817–5820 (1991)); chronic myelogenous leukemia at 10q21 (Shah, N. K., et al., *Cancer Genet. Cytogenet.*, 61;183–192 (1992)); glioma at 10q21–26 (Oberstrass, J., et al., *Verh Dtsch. Ges. Pathol.* 78:413–417, (1994)); gliobiastoma, two independent regions at 10pter–q11 and 10q24–q26 (Steck, P. A., et al., *Genes Chromosomes Cancer* 12:255–261 (1995)); colonic denocarcinoma, an inverted, non-ret duplication of 10q11 to 10q21 (Solic, N., et al., *Int. J. Cancer* 62:48–57, (1995)); lung carcinoma at 10q21-10qter (Petersen, S., et al., *Br. J. Cancer* 77:270–276 (1998)); hepatocellular carcinoma at 10q (Piao, Z., et al., *Int. J. Cancer* 75:29–33 (1996)); and prostate cancer, two independent loci at 10q21 and 10q23–24 (Lacombe, L., et al., *Int. J. Cancer* 69:110–113 (1996)). A frequently deleted locus on chromosome 10q24–25 has recently been shown to harbor the PTEN tumor suppressor gene (Li J., et al., *Science* 275:1943–1947 (1997)), thus supporting the concept of multiple candidate tumor suppressor genes in this region. Finally, Ford, S., et. al. have shown that the long arm of chromosome 10 is rearranged in the prostate adenocarcinoma cell line LNCaP (*Cancer Genet. Cytogenet.* 102:6–11 (1998)).

The subcellular distribution of ANX7 protein is predominantly in membranes and to a lesser extent in the nucleus (Cardenas, A. M., et al., *Biochim. Biophys. Acta.* 1:234, 255–260 (1994); Kuijpers, G. A. J., et al., *Cell Tissue Res.* 269:323–330 (1992)). The ANX7 protein has $Ca^{2+}$-dependent membrane fusion activity (Creutz, C. E., et al., *J. Biol. Chem.* 253:2858–2866 (1978); Creutz, C. E., et al., *J. Biol. Chem.* 254:553–558 (1979)), which is profoundly potentiated by GTP (Caohuy, H., et al., *Proc. Nat Acad. Sci.* (USA), 93:10797–10802, (1996)). The action of GTP on ANX7 function is regulated by an intrinsic $Ca^{2+}$-activated GTPase. ANX7 GTPase activity is sensitive to such critical modulators of conventional G-proteins as $Al_2F_6$ and mastoparan (Caohuy, H., et al., *Secretory Systems and Toxins* (eds., Linial, M., et al.) 2:439–449 (1998)). In studies with cultured cells, ANX7 can be shown to bind and hydrolyze GTP. ANX7 protein also forms $Ca^{2+}$ channels in membranes (Pollard, H. B., et al., *Proc. Natl. Acad. Sci.* (USA) 85:2974–2978 (1988)), which can be stabilized in long open states by GTP.

Protein kinase C phosphorylates ANX7 with a 2:1 P/Protein molar ratio, both in vitro and in vivo. This is of possible relevance to ANX7 function in the cell cycle since many isoforms of PKC have been directly implicated in activating intracellular signaling (Nishizuka, Y., *Science* 258:607–614 (1992), and in specifically activating mitosis (Kolch, W., et al., *Nature* 364:426–428 (1993); Berra, E., et al., *Cell* 74:555–563 (1993); Cacace, A., et al., *Oncogene* 8:2094–2104 (1993); Morrisson, D. K., et al., *Proc. Nat Acad. Sci.* (USA) 85:8855–8859 (1998); and tumorigenicity (Housey, G. M., et al., *Cell,* 52:343–354 (1988); Mischak, H., et al.,*J. Biol. Chem.* 268:6090–6096 (1993); Persons, D. A., et al., *Cell* 52:447–458 (1988)). Quantitative phospho-ANX7 adducts have also been prepared in vitro with EGF (epidermal growth factor) receptor and pp603$^{src}$. In vivo, cells treated with tyrosine kinase activators such as epidermal growth factor (EGF) and platelet derived growth factor (PGDF) also support phosphorylation of endogenous ANX7. These reactions are of as yet unknown biological significance. However, the relevance of such reactivity to tumor suppressor gene activity is manifest by reports that splice variants of the breast and ovarian cancer susceptibility gene BRCA1 contain phosphotyrosine and play a role in cell cycle regulation (Cui, J. Q., et al., *Oncol. Rep.* 5:585–589 (1998); Wang, H., et al., *Oncogene* 15:143–157 (1997); Zhang, H. T., et al., *Oncogene* 14:2863–2869 (1997)).

IV. The Interaction of Mutant and Normal Annexin Gene Products

Studies of the clonal nature of tumor formation have suggested that tumors have a monoclonal composition, and hence arise by the clonal propagation of a single progenitor cell (Fearson, E. R. et al., *Science* 247:193–197 (1987)).

The simplest model to explain the mechanism of action of a tumor-suppressing gene is that malignancy requires two separate genetic events (e.g., loss by deletion or mutation of both functional anx7 alleles in a cell). Inactivation of only one of the two natural anx7 alleles causes the animal to be more susceptible to cancerous growths.

Transgenic animals may be used to investigate the biological implications of tumor-suppressing genes (Capecchi, M. R., *Science* 244:1288–1292 (1989)). Lavigueur, A. et al. constructed a transgenic mouse which had a single added mutant p53 gene in addition to the endogenous two wildtype p53 alleles. The mouse and its progeny overexpressed the added p53 gene. The mice were found to have a high incidence of lung, bone, and lymphoid tumors (Lavigueur, A. et al., *Molec. Cell. Biol.* 9:3982–3991 (1989)).

Thus, this invention provides a transgenic animal whose genome possesses one normal and functional anx7 allele and one non-functional (mutant) anx7 allele. Such animals could be used to study the consequences resulting from the loss of one anx7 allele, and thus would more clearly aid in elucidating the processes of oncogenesis and tumorigenesis. Such animals would also be useful in screening potential carcinogens, in developing novel antineoplastic therapeutics, and in gene therapy.

V. Homologous Recombination

The present invention uses the process of homologous recombination to introduce a specific mutation into the naturally present anx7 sequence of an animal cell, most preferably an embryonic stem (ES) cell. The mutated ES cells of non-human animals can then be either cultured in suitable cell culture medium or introduced into the uterus of a suitable recipient and permitted to develop into a non-human animal. Alternatively, the methods of the present invention may be used to alter the somatic cells of a non-human animal to produce a chimeric non-human animal.

An understanding of the process of homologous recombination (Watson, J. D., In: Molecular Biology of the Gene, 3rd Ed., W. A. Benjamin, Inc., Menlo Park, Calif. (1977)) is thus desirable in order to fully appreciate the present invention.

In brief, homologous recombination is a well-studied natural cellular process which results in the scission of two nucleic acid molecules having identical or substantially similar sequences (i.e., "homologous"), and the ligation of the two molecules such that one region of each initially present molecule is now ligated to a region of the other initially present molecule (Sedivy, J. M., *Bio-Technol.* 6:1192–1196 (1988)).

Homologous recombination is, thus, a sequence specific process by which cells can transfer a "region" of DNA from one DNA molecule to another. As used herein, a "region" of DNA is intended to generally refer to any nucleic acid molecule. The region may be of any length from a single base to a substantial fragment of a chromosome. For homologous recombination to occur between two DNA molecules, the molecules must possess a "region of homology" with respect to one another. Such a region of homology must be at least two base pairs long and having a substantially similar nucleic acid sequence.

Recombination is catalyzed by enzymes which are naturally present in both prokaryotic and eukaryotic cells. The transfer of a region of DNA may be envisioned as occurring through a multi-step process.

If either of the two participant molecules is a circular molecule, then the recombination event results in the integration of the circular molecule into the other participant. Importantly, if a particular region is flanked by regions of homology (which may be the same, but are preferably different), then two recombinational events may occur, and result in the exchange of a region of DNA between two DNA molecules. Recombination may be "reciprocal," and thus results in an exchange of DNA regions between two recombining DNA molecules. Alternatively, it may be "non-reciprocal," (also referred to as "gene conversion") and result in both recombining nucleic acid molecules having the same nucleotide sequence. There are no constraints regarding the size or sequence of the region which is exchanged in a two-event recombinational exchange.

The frequency of recombination between two DNA molecules may be enhanced by treating the introduced DNA with agents which stimulate recombination. Examples of such agents include trimethylpsoralen, UV light, etc.

VII. Production of Chimeric and Transgenic Animals: Gene Targeting Methods

One approach to producing animals having defined and specific genetic alterations has used homologous recombination to control the site of integration of an introduced marker gene sequence in tumor cells and in fusions between diploid human fibroblast and tetraploid mouse erythroleukemia cells (Smithies, O. et al., *Nature* 317:230–234 (1985)).

This approach was further exploited by Thomas, K. R., and co-workers, who described a general method, known as "gene targeting," for targeting mutations to a preselected, desired gene sequence of an ES cell in order to produce a transgenic animal (Mansour, S. L. et al., *Nature* 336:348–352 (1988); Capecchi, M. R., *Trends Genet.* 5:70–76 (1989); Capecchi, M. R., *Science* 244:1288–1292 (1989); Capecchi, M. R. et al., In: Current Communications in Molecular Biology, Capecchi, M. R. (ed.), Cold Spring Harbor Press, Cold Spring Harbor, N.Y. (1989), pp. 45–52; Frohman, M. A. et al., *Cell* 56:145–147 (1989)).

It may now be feasible to deliberately alter any gene in a mouse (Capecchi, M. R., *Trends Genet.* 5:70–76 (1989); Frohman, M. A. et al., *Cell* 56:145–147 (1989)). Gene targeting involves the use of standard recombinant DNA techniques to introduce a desired mutation into a cloned DNA sequence of a chosen locus. That mutation is then transferred through homologous recombination to the genome of a pluripotent, embryo-derived stem (ES) cell. The altered stem cells are microinjected into mouse blastocysts and are incorporated into the developing mouse embryo to ultimately develop into chimeric animals. In some cases, germ line cells of the chimeric animals will be derived from the genetically altered ES cells, and the mutant genotypes can be transmitted through breeding.

Gene targeting has been used to produce chimeric and transgenic mice in which an nptll gene has been inserted into the $\beta_2$-microglobulin locus (Koller, B. H. et al., *Proc. Natl. Acad. Sci.* (U.S.A.) 86:8932–8935 (1989); Zijlstra, M. et al., *Nature* 342:435–438 (1989); Zijlstra, M. et al., *Nature* 344:742–746 (1989); DeChiaba et al., *Nature* 345:78–80 (1990)). Similar experiments have enabled the production of chimeric and transgenic animals having a c-abl gene which has been disrupted by the insertion of an nptll gene (Schwartzberg, P. L. et al., *Science* 246:799–803 (1989)). The technique has been used to produce chimeric mice in which the en-2 gene has been disrupted by the insertion of an nptll gene (Joyner, A. L. et al., *Nature* 338:153–155 (1989)).

In order to utilize the "gene targeting" method, the gene of interest must have been previously cloned, and the intron-exon boundaries determined. The method results in the insertion of a marker gene (i.e. the nptll gene) into a translated region of a particular gene of interest. Thus, use of the gene targeting method results in the gross destruction of the gene of interest.

Significantly, the use of gene targeting to alter a gene of a cell results in the formation of a gross alteration in the sequence of that gene. The efficiency of gene targeting depends upon a number of variables, and is different from construct to construct.

VIII. The Production of Chimeric and Transgenic Animals

The chimeric or transgenic animal cells of the present invention are prepared by introducing one or more DNA molecules into a precursor pluripotent cell, most preferably an ES cell, or equivalent (Robertson, E. J., In: Current Communications in Molecular Biology, Capecchi, M. R. (ed.), Cold Spring Harbor Press, Cold Spring Harbor, N.Y. (1989), pp. 39–44, which reference is incorporated herein by reference). The term "precursor" is intended to denote only that the pluripotent cell is a precursor to the desired ("transfected") pluripotent cell which is prepared in accordance with the teachings of the present invention. The pluripotent (precursor or transfected) cell may be cultured in vivo, in a manner known in the art (Evans, M. J. et al., *Nature* 292:154–156 (1981)) to form a chimeric or transgenic animal.

Any ES cell may be used in accordance with the present invention. It is, however, preferred to use primary isolates of ES cells. Such isolates may be obtained directly from embryos such as the CCE cell line disclosed by Robertson, E. J., In: Current Communications in Molecular Biology, Capecchi, M. R. (ed.), Cold Spring Harbor Press, Cold Spring Harbor, N.Y. (1989), pp. 39–44), or from the clonal isolation of ES cells from the CCE cell line (Schwartzberg, P. A. et al., Science 246:799–803 (1989), which reference is incorporated herein by reference). Such clonal isolation may be accomplished according to the method of E. J. Robertson (In: Teratocarcinomas and Embryonic Stem Cells: A Practical Approach, (E. J. Robertson, Ed.), IRL Press, Oxford, 1987) which reference and method are incorporated herein by reference. The purpose of such clonal propagation is to obtain ES cells which have a greater efficiency for differentiating into an animal. Clonally selected ES cells are approximately 10-fold more effective in producing transgenic animals than the progenitor cell line CCE. For the purposes of the recombination methods of the present invention, clonal selection provides no advantage.

An example of ES cell lines which have been clonally derived from embryos are the ES cell lines, AB1 (hprt$^+$) or AB2.1 (hprt$^-$). The ES cells are preferably cultured on stromal cells (such as STO cells (especially SNC4 STO cells) and/or primary embryonic fibroblast cells) as described by E. J. Robertson (In: Teratocarcinomas and Embryonic Stem Cells: A Practical Approach, (E. J. Robertson, Ed., IRL Press, Oxford, 1987, pp 71–112), which reference is incorporated herein by reference. Methods for the production and analysis of chimeric mice are disclosed by Bradley, A. (In: Teratocarcinomas and Embryonic Stem Cells: A Practical Approach, (E. J. Robertson, Ed.), IRL Press, Oxford, 1987, pp 113–151), which reference is incorporated herein by reference. The stromal (and/or fibroblast) cells serve to eliminate the clonal overgrowth of abnormal ES cells. Most preferably, the cells are cultured in the presence of leukocyte inhibitory factor ("lif") (Gough, N. M. et al., *Reprod. Fertil. Dev.* 1:281–288 (1989); Yamamori, Y. et al., *Science* 246:1412–1416 (1989), both of which references are incorporated herein by reference). Since the gene encoding lif has been cloned (Gough, N. M. et al., *Reprod. Fertil. Dev.* 1:281–288 (1989)), it is especially preferred to transform stromal cells with this gene, by means known in the art, and to then culture the ES cells on transformed stromal cells that secrete lif into the culture medium.

ES cell lines may be derived or isolated from any species (for example, chicken, etc.), although cells derived or isolated from mammals such as rodents (i.e. mouse, rat, hamster, etc.), rabbits, sheep, goats, fish, pigs, cattle, primates and humans are preferred.

IX. Uses of the Present Invention

The present invention provides human or animal cells which contain a desired gene sequence in one of the two annexin gene alleles of the cell's genome. In a first embodiment, the invention also provides a means for producing non-human chimeric or transgenic animals whose cells contain such a sequence. The animals which may be produced through application of the described method include chicken, non-human mammals (especially, rodents (i.e. mouse, rat, hamster, etc.), rabbits, sheep, goats, fish, pigs, cattle and non-human primates).

The cells and non-human animals of the present invention have both diagnostic and therapeutic utility.

A. Diagnostic Utility

Since the invention provides a cell, or a transgenic or chimeric non-human animal, that contains a single functional allele of the anx7 gene, and since such cells will become tumor cells upon the mutation of the functional allele to a non-functional form, the present invention can be used to identify an agent that is capable of affecting a characteristic of an animal cell that is attributable to the presence or expression of a tumor-suppressing gene. A characteristic of an animal cell is said to be "attributable to the presence or expression of a tumor-suppressing gene," if the characteristic is altered by the absence or lack of expression of the tumor-suppressing gene. Examples of such characteristics include tumorigenesis, resilience to tumorigenesis, the extent, distribution, incidence, location, grade, etc. of tumors, etc.

In one embodiment, such agents can decrease the tumorigenic (or neoplastic) potential of the cells or animals. Such agents are discussed below with regard to the therapeutic potential of the invention.

In a second embodiment, such agent can increase the tumorigenic (or neoplastic) potential of the cells or animals. Thus, the cells and non-human animals of the present invention have utility in testing potential or suspected carcinogens for tumorigenic activity. They may be used to identify and assess the tumorigenic effects of agents that may be present, for example, in the environment (such as environmental pollutants in air, water or soil), or resulting from environmental exposures to chemicals, radioisotopes, etc. They may also be used to facilitate studies of the effects of diet on oncogenesis. They may be used to determine whether potential or present food additives, chemical waste products, chemical process by-products, water sources, proposed or presently used pharmaceuticals, cosmetics, etc., have tumorigenic activity. They may also be used to determine the tumorigenic potential of various energy forms (such as UV rays, X-rays, ionizing radiation, gamma rays of elemental isotopes, etc.).

The frequency at which a mutational event occurs is dependent upon the concentration of a mutagenic chemical agent, or the intensity of a mutagenic radiation. Thus, since the frequency of a single cell receiving two mutational events is the square of the frequency at which a single mutational event will occur, the cells and non-human animals of the present invention shall be able to identify neoplastic (mutagenic) agents at concentrations far below those needed to induce neoplastic changes in natural cells or animals. This is because one allele of the tumor suppressing gene anx7 has already been mutated in the transgenic mouse of the present invention.

One especially preferred cell is a non-human cell in which one of the natural anx7 alleles has been replaced with a functional human anx7 allele and the other of the natural anx7 alleles has been mutated to a non-functional form. Alternatively, one may employ a non-human cell in which the two natural anx7 alleles have been replaced with a functional and a non-functional allele of the human anx7 gene.

Such cells may be used, in accordance with the methods described above, to assess the neoplastic potential of agents in cells containing the human anx7 allele. More preferably, such cells are used to produce non-human animals which do not contain any natural functional anx7 alleles, but which contain only one functional human anx7 allele. Such non-human animals can be used to assess the tumorigenicity of an agent in a non-human animal expressing the human anx7 gene product.

1. In Vitro Assays

In one embodiment, one may employ the cells of the present invention, in in vitro cell culture, and incubate such cells in the presence of an amount of the agent whose tumorigenic potential is to be measured. This embodiment therefore comprises an in vitro assay of tumorigenic activity.

Although many carcinogenic agents may directly mediate their tumorigenic effects, some agents will not exhibit tumorigenic potential until metabolized, or until presented to a susceptible cell along with one or more "co-carcinogenic" factors. The present invention permits the identification of such "latent" carcinogenic and "co-carcinogenic" agents. In accordance with this embodiment of the invention, the presence of a "latent" carcinogen can be identified by merely maintaining cell or animal exposure to a candidate agent. Alternatively, the cells of the present invention can be incubated in "conditioned" culture medium (i.e. medium containing the candidate agent that was used to culture other cells before being used to culture the cells of the present invention).

The present invention permits the identification of co-carcinogenic factors capable of inducing neoplastic effects in the presence of a second agent. Such factors can be identified by culturing the cells of the present invention in the presence of two or more candidate agents simultaneously, and then assaying for neoplasia. The transformation of the cells to a neoplastic state would be indicative of tumorigenic (or neoplastic) activity of the assayed agent. Such a neoplastic state may be evidenced by a change in cellular morphology, by a loss of contact inhibition, by the acquisition of the capacity to grow in soft agar, or most preferably, by the initiation of expression of tumor antigens.

The use of tumor antigens as a means of detecting neoplastic activity is preferred since such antigens may be readily detected. As is well known in the art, antibodies, or fragments of antibodies, may be used to quantitatively or qualitatively detect the presence tumor of antigens on cell surfaces. Since any cell type (i.e. lung, kidney, colon, etc.) may be employed to form the anx7-mutated cells of the present invention, it is possible to determine whether an agent has a tissue specific tumorigenic potential. To accomplish this goal, one would incubate a candidate agent in the presence of anx7-mutated cells derived from any of a variety of tissue types. Since tumors have tumor-specific antigens, and since antibodies capable of binding to such antigens have been isolated, it is possible to use such antibodies to characterize any tumor antigens which may be expressed by the anx7-mutated cells. Such detection may be accomplished using any of a variety of immunoassays. For example, by radioactively labeling the antibodies or antibody fragments, it is possible to detect the antigen through the use of radioimmune assays.

A good description of a radioimmune assay (RIA) may be found in Laboratory Techniques and Biochemistry in Molecular Biology, by Work, T. S., et al., North Holland Publishing Company, NY (1978), with particular reference to the chapter entitled "An Introduction to Radioimmune Assay and Related Techniques" by Chard, T., incorporated by reference herein. Examples of suitable radioisotopic labels include $^{3}H$, $^{111}In$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, $^{109}Pd$, etc.

Alternatively, enzyme labels, non-radioactive isotopic labels, fluorescent labels, chemiluminescent labels or other suitable labels can be employed. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc. Examples of suitable non-radioactive isotopic labels include $^{157}Gd$, $^{55}Mn$, $^{162}Dy$, $^{52}Tr$, $^{56}Fe$, etc.

Examples of suitable fluorescent labels include an $^{152}Eu$ label, a fluorescein label, an isothiocyanate label, a rhodamine label, a phycoerythrin label, a phycocyanin label, an allophycocyanin label, an o-phthaldehyde label, a fluorescamine label, etc.

Examples of chemiluminescent labels include a luminal label, an isoluminal label, an aromatic acridinium ester label, an imidazole label, an acridinium salt label, an oxalate ester label, a luciferin label, a luciferase label, an aequorin label, etc. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al. (*Clin. Chim. Acta* 70:1–31 (1976)), and Schurs, A. H. W. M., et al. (*Clin. Chim. Acta* 81:1–40 (1977)). Coupling techniques mentioned in the latter are the glutaraldehyde method, the periodate method, the dimaleimide method, the m-maleimidobenzyl-N-hydroxy-succinimide ester method, all of which methods are incorporated by reference herein.

The above-described in vitro assay has the advantageous features of potentially lower cost than presently used assays, and the capacity to readily screen large numbers of agents. Use of this embodiment facilitates comparisons of test results obtained at different times and conditions. Moreover, because it is possible to use very large numbers of cells in such assays, it is possible to detect the tumorigenic activity of tumorigenic agents even at very low concentrations. Lastly, since this embodiment can be performed using human cells, it provides a means for determining the tumorigenic (or neoplastic) potential of a test compound on human cells.

2. In Vivo Assays

In a second embodiment, one may employ the non-human animals of the present invention, and provide to such animals (by, for example, inhalation, ingestion, injection, implantation, etc.) an amount of the agent whose tumorigenic potential is to be measured. The formation of tumors in such animals (as evidenced by direct visualization by eye, or by biopsy, imaging, detection of tumor antigens, etc.) would be indicative of tumorigenic activity of the assayed agent.

The use of the non-human animals of the present invention is preferred over naturally occurring non-human animals because natural animals contain two functional anx7 alleles and thus require two mutational events in order to lead to loss of functional anx7 activity. In contrast, since the non-human animals of the present invention have only one functional anx7 allele, only one mutational event is needed to cause total loss of anx7 function.

The detection of tumors in such animals can be accomplished by biopsy, imaging, or by assaying the animals for the presence of cells which express tumor antigens. For example, such detection may be accomplished by removing a sample of tissue from a subject and then treating the isolated sample with any suitably labeled antibodies (or antibody fragments) as discussed above. Preferably, such in situ detection is accomplished by removing a histological specimen from the subject, and providing the labeled antibody to such specimen. The antibody (or fragment) is preferably provided by applying or by overlaying the labeled antibody (or fragment) to a sample of tissue. Through the use of such a procedure, it is possible to determine not only the presence of antigen, but also the distribution of the antigen on the examined tissue. Using the present invention, those of ordinary skill will readily perceive that any of a wide variety of histological methods (such as staining procedures) can be modified in order to achieve such in situ detection.

Alternatively, the detection of tumor cells may be accomplished by in vivo imaging techniques, in which the labeled antibodies (or fragments thereof) are provided to the subject, and the presence of the tumor is detected without the prior removal of any tissue sample. Such in vivo detection procedures have the advantage of being less invasive than other detection methods, and are, moreover, capable of detecting the presence of antigen-expressing cells in tissue which cannot be easily removed from the patient. Additionally, it is possible to assay for the presence of tumor antigens in body fluids (such as blood, lymph, etc.), stools, or cellular extracts. In such immunoassays, the antibodies (or antibody fragments) may be utilized in liquid phase or bound to a solid-phase carrier, as described below.

The use of an in vivo assay has several advantageous features. The in vivo assay permits one not only to identify tumorigenic agents, but also to assess the kind(s) of tumors induced by the agent, the number and location (i.e. whether organ or tissue specific) of any elicited tumors, and the grade (clinical significance) of such elicited tumors. It further permits an assessment of tumorigenicity which inherently considers the possible natural metabolism of the introduced agent, the possibility that the introduced agent (or its metabolic by-products) might selectively accumulate in specific tissues or organs of the recipient animal, the possibility that the recipient animal might recognize and repair or prevent tumor formation. In short, such an assay provides a true biological model for studying and evaluating the tumorigenic potential of an agent in a living non-human animal.

3. Immunoassays of Tumor Antigens

The in vitro, in situ, or in vivo detection of tumor antigens using antibodies (or fragments of antibodies) can be improved through the use of carriers. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen. Thus, the support configuration may be spherical, as in a bead, or cylindrical, as in the inside surface of a test tube, or the external surface of a rod. Alternatively, the surface may be flat such as a sheet, test strip, etc. Those skilled in the art will note many other suitable carriers for binding monoclonal antibody, or will be able to ascertain the same by use of routine experimentation.

The binding molecules of the present invention may also be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested (i.e., blood, lymph, liquified stools, tissue homogenate, etc.) and a quantity of detectably labeled soluble antibody is added to permit detection and/or quantitation of the ternary complex formed between solid-phase antibody, antigen, and labeled antibody.

Typical immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody. This type of forward sandwich assay may be a simple "yes/no" assay to determine whether antigen is present or may be made quantitative by comparing the measure of labeled antibody with that obtained for a standard sample containing known quantities of antigen. Such "two-site" or "sandwich" assays are described by Wide at pages 199–206 of Radioimmune Assay Method, edited by Kirkham and Hunter, E. & S. Livingstone, Edinburgh, 1970.

In another type of "sandwich" assay, which may also be useful to identify tumor antigens, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

The immunometric assays for antigen require that the particular binding molecule be labeled with a "reporter molecule." These reporter molecules or labels, as identified above, are conventional and well-known to the art. In the practice of the present invention, enzyme labels are a preferred embodiment. No single enzyme is ideal for use as a label in every conceivable immunometric assay. Instead, one must determine which enzyme is suitable for a particular assay system. Criteria important for the choice of enzymes are turnover number of the pure enzyme (the number of substrate molecules converted to product per enzyme site per unit of time), purity of the enzyme preparation, sensitivity of detection of its product, ease and speed of detection of the enzyme reaction, absence of interfering factors or of enzyme-like activity in the test fluid, stability of the enzyme and its conjugate, availability and cost of the enzyme and its conjugate, and the like. Included among the enzymes used as preferred labels in the immunometric assays of the present invention are peroxidase, alkaline phosphatase, beta-galactosidase, urease, glucose oxidase, glycoamylase, malate dehydrogenase, and glucose-6-phosphate dehydrogenase. Urease is among the more preferred enzyme labels, particularly because of chromogenic pH indicators which make its activity readily visible to the naked eye.

B. Therapeutic Utility

Significantly, the cells and animals of the present invention can be used to identify agents that decrease the tumorigenic (or neoplastic) potential of the cells or animals. Such agents can be "anti-tumor agents" and/or "chemopreventative agents." "Anti-tumor agents" act to decrease the proliferation of the cells (or the growth, dissemination, or metastasis of tumors in the chimeric or transgenic animals). "Chemopreventative agents" act to inhibit the formation of new tumors. Such agents may have general activity (inhibiting all new tumor formation), or may have a specific activity (inhibiting the distribution, frequency, grade, etc.) of specific types of tumors in specific organs and tissue. Thus, the present invention permits the identification of novel antineoplastic therapeutics. Any of the assays in section A. above may be used for determining tumor-suppressing activity.

The transgenic cells and non-human animals of the present invention can be used to study human gene regulation of the anx7 gene. For example, such cells and animals can be used to investigate the interactions of the anx7 gene with oncogenes or other tumor suppressor genes. Thus, they may be used to identify therapeutic agents which have the ability to impair or prevent neoplastic or tumorigenic development. Such agents have utility in the treatment and cure of cancer in humans and animals. Significantly, potential therapeutic agents are frequently found to induce toxic effects in one animal model but not in another animal model. To resolve the potential of such agents, it is often necessary to determine the metabolic patterns in various species, and to then determine the toxicities of the metabolites. The present invention permits one to produce transgenic cells or animals which could facilitate such determinations.

When providing the therapeutic agents of the present invention to the cells of an animal, pharmaceutically acceptable carriers (i.e. liposomes, etc.) are preferably employed. Such agents can be formulated according to known methods to prepare pharmaceutically useful compositions, whereby these materials, or their functional derivatives, are combined in admixture with a pharmaceutically acceptable carrier vehicle. Suitable vehicles and their formulation, are described, for example, in Nicolau, C. et al. (*Crit. Rev. Ther. Drug Carrier Syst.* 6:239–271 (1989)), which reference is incorporated herein by reference.

In order to form a pharmaceutically acceptable composition suitable for effective administration, such compositions will contain an effective amount of the desired gene sequence together with a suitable amount of carrier vehicle.

Additional pharmaceutical methods may be employed to control the duration of action. Control release preparations may be achieved through the use of polymers to complex or absorb the desired gene sequence (either with or without any associated carrier). The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate the agent into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions.

C. Use in Research and in Gene Therapy

The cells and non-human animals of the present invention may be used to investigate gene regulation, expression and organization in animals. The methods of the present invention may be used to produce alterations in a regulatory region of the native anx7 gene sequence. Thus, the invention provides a means for altering the nature or control of transcription or translation of the anx7 gene, and of altering the anx7 gene itself. For example, the invention enables one to introduce mutations which result in increased or decreased gene expression. Similarly, it enables one to impair or enhance the transcriptional capacity of the natural anx7 gene in order to decrease or increase its expression. Thus, the present invention permits the manipulation and dissection of the anx7 gene. Such abilities are especially valuable in gene therapy protocols and in the development of improved animal models of cancer.

The principles of gene therapy are disclosed by Oldham, R. K. (In: Principles of Biotherapy, Raven Press, N.Y., 1987), and similar texts. Disclosures of the methods and uses for gene therapy are provided by Boggs, S. S. (*Int. J. Cell Clon.* 8:80–96 (1990)); Karson, E. M. (*Biol. Reprod.* 42:39–49 (1990)); Ledley, F. D., In: Biotechnology, A Comprehensive Treatise, volume 7B, Gene Technology, VCH Publishers, Inc. NY, pp 399–458 (1989)), all of which references are incorporated herein by reference.

In one embodiment of the present invention, DNA encoding either a functional anx7 gene, variants of that gene, or other genes which influence the activity of the anx7 gene, may be introduced into the somatic cells of an animal (particularly mammals including humans) in order to provide a treatment for cancer (i.e. "gene therapy"). Most preferably, viral or retroviral vectors are employed for this purpose.

Retroviral vectors are a common mode of delivery and in this context are retroviruses from which all viral genes have been removed or altered so that no viral proteins are made in cells infected with the vector. Viral replication functions are provided by the use of retrovirus "packaging" cells that produce all of the viral proteins but that do not produce infectious virus.

Introduction of the retroviral vector DNA into packaging cells results in production of virions that carry vector RNA and can infect target cells, but such that no further virus spread occurs after infection. To distinguish this process from a natural virus infection where the virus continues to replicate and spread, the term transduction rather than infection is often used.

Non-retroviral vectors have been used in genetic therapy. One such alternative is the adenovirus (Rosenfeld, M. A., et al., *Cell* 68:143155 (1992); Jaffe, H. A. et al., *Nature Genetics* 1:372–378 (1992); Lemarchand, P. et al., *Proc. Natl. Acad. Sci. USA* 89:6482–6486 (1992)). Major advantages of adenovirus vectors are their potential to carry large segments of DNA (36 Kb genome), a very high titre ($10^{11}$/ml), ability to infect non-replicating cells, and suitability for infecting tissues in situ, especially in the lung. The most striking use of this vector so far is to deliver a human cystic fibrosis transmembrane conductance regulator (CFTR) gene by intratracheal instillation to airway epithelium in cotton rats (Rosenfeld, M. A., et al., *Cell* 63:143–155 (1992)). Similarly, herpes viruses may also prove valuable for human gene therapy (Wolfe, J. H. et al., *Nature Genetics* 1:379–384 (1992)). Of course, any other suitable viral vector may be used for genetic therapy with the present invention.

Another gene transfer method for use in humans is the transfer of plasmid DNA in liposomes directly to human cells in situ (Nabel, E. G., et al., *Science* 249:1285–1288 (1990)). Plasmid DNA should be easy to certify for use in human gene therapy because, unlike retroviral vectors, it can be purified to homogeneity. In addition to liposome-mediated DNA transfer, several other physical DNA transfer methods, such as those targeting the DNA to receptors on cells by conjugating the plasmid DNA to proteins, have shown promise in human gene therapy (Wu, G. Y., et al., *J. Biol. Chem.* 266:14338–14342 (1991); Curiel, D. T., et al., *Proc. Natl. Acad. Sci. USA,* 88:8850–8854 (1991)).

In applying these methods of therapy, it has been observed that certain tumor cells return to normal function when fused with normal cells, suggesting that replacement of a missing factor, such as a wild-type tumor suppressor gene expression product may serve to restore a tumor cell to a normal state (reviewed by Weinberg, R. A., *Cancer Research* 49:3713–3721, at 3717 (1989)).

These observations have led to research aimed at providing genetic treatment of tumor cells having defective tumor suppressor genes. The proposed method of treatment requires identification of the damaged tumor suppressor gene, and introduction of the corresponding undamaged gene (including a promoter and a complete encoding sequence) into the affected tumor cells by means of a vector such as an adenovirus vector able to express the gene product. It is proposed that the incorporated functional gene will convert the target cell to a non-malignant state.

For example, The Regents of the University of California, in Patent Cooperation Treaty patent application (by Lee et al., number WO 90/05180, having an international filing date of Oct. 30, 1989 and published May 17, 1990), disclose a scheme for identifying an inactive or defective tumor suppressor gene and then replacing such a defective gene with its functional equivalent. In particular, the WO 90/05180 application proposes, based on in vitro studies, to insert a functional RB[110] gene into an RB-minus tumor cell by means of a retroviral vector in order to render such cells non-malignant.

Although, as indicated above, such gene therapy can be provided to a recipient in order to treat (i.e. suppress, attenuate, or cause regression) an existing neoplastic state, the principles of the present invention can also be used to provide a prophylactic gene therapy to individuals who, due to inherited genetic mutations, or somatic cell mutation, contain cells having impaired anx7 gene expression (for example, only a single functional allele of the anx7 gene). Such therapy could be administered in advance of the detection of cancer in order to lessen the individual's predisposition to the disease.

Having now generally described the invention, the same will be more readily understood through reference to the following examples which are provided by way of illustration, and are not intended to be limiting of the present invention, unless specified.

EXAMPLE I

Production and Characterization of a Transgenic Mouse for the anx7 Gene

Before beginning the actual production of transgenic mice, the genomic locus for annexin VII (anx7) was characterized. Then, a transgene construct ("targeting vector") was prepared based on this characterization. This construct carries the necessary elements to facilitate the transgenic animal construction.

The anx7 genomic locus from a 129SV/CPJ mouse genomic library (Stratagene), which contained 14 exons of the anx7 gene spanning about 34 kb, was screened with mouse anx7 cDNA probe (Zhang-Keck, et al., Biochem. J. 301:835–845.)

Figure 2:
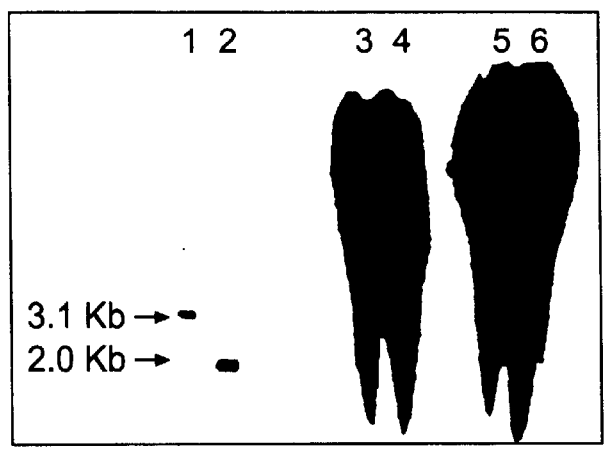
FIG. 2 depicts the southern blot analysis of the targeting construct.

In order to assess which segments of the genomic locus were most suitable for use in the targeting vector, several restriction fragments including three Xba I fragments (1.9, 3.6 and 3.1 kb) and one Xho I fragment (2.0 kb) encompassing this region were subcloned, labeled with $^{32}$[P], and tested for the presence of repetitive sequences. Repetitive sequences are undesirable because they can cause random insertion of the anx7 gene into any part of the chromosome. Therefore, these regions were removed. A Southern blot analysis revealed that only the 3.1 kb Xba I genomic DNA fragment and the 2.0 kb Xho I genomic DNA fragment of the four fragments tested, when used as a probe, gave sharp bands on a genomic Southern of mouse ES cell DNA. In FIG. 2, the genomic DNA derived from ES cells was digested with Hind III, blotted and hybridized with $^{32}$P-labeled genomic fragments. A single band was seen with probes from the 3.1 kb Xba I fragment (lane 1) and the 2.0 kb Xho I fragment (lane 2) of mouse anx7. A smear was noted with the 1.9 kb and 3.6 kb Xba I fragments (lanes 3, 4 and 5, 6, respectively). Thus, the conclusion drawn is that the single band fragments do not contain repetitive sequences and therefore, were used in the targeting vector.

A. Construction of the Targeting Vector

To construct the anx7 gene targeting vector, the 2.0 kb Xho I genomic DNA fragment (containing exons 4 and 5) and the 3.1 kb Xba I genomic DNA fragment (containing exons 7 and 8) were inserted into the Xho I site and the XbaI site of pPNT, respectively, to generate the replacement type targeting vector termed KSBX.pPNT (See FIG. 1A). The vector, pPNT (obtained from Dr. Heiner Westphal's laboratory at NICHD, NIH) contained PGKneo and PGKtk cassettes, separated and flanked by a number of unique cloning sites. The neo gene was determined to be in the same orientation as the anx7 gene. A herpes simplex virus thymidine kinase (TK) gene was also added to the targeting vector as a marker sequence which would be deleted in the event of homologous recombination between the targeting vector and the wild type allele. This allowed selection against cells that had undergone nonhomologous integration.

B. Transfection and Selection of ES Cells

Pluripotent embryonic stem cells (referred to as "ES" cells) are cells which may be obtained from embryos until the early post-implantation stage of embryogenesis. The cells may be propagated in culture, and are able to differentiate either in vitro or in vivo upon implantation into a mouse as a tumor. ES cells have a normal karyotype (Evans, M. J. et al., *Nature* 292:154–156 (1981); Martin, G. R. et al., *Proc. Natl. Acad. Sci.* (*U.S.A.*) 78:7634–7638 (1981)).

Upon injection into a blastocyst of a developing embryo, ES cells will proliferate and differentiate, thus resulting in the production of a chimeric animal. ES cells are capable of colonizing both the somatic and germ-line lineages of such a chimeric animal (Robertson, E. et al., Cold Spring Harb. Conf. Cell Prolif. 10:647–663 (1983); Bradley A. et al., Nature 309:255–256 (1984); Bradley, A. et al., Curr. Top. Devel. Biol. 20:357–371 (1986); Wagner, E. F. et al., Cold Spring Harb. Symp. Quant. Biol. 50:691–700 (1985); (all of which references are incorporated herein by reference).

Because ES cells may be propagated in vitro, it is possible to manipulate such cells using the techniques of somatic cell genetics. Thus, it is possible to select ES cells which carry mutations (such as in the hprt gene (encoding hypoxanthine phosphoribosyl transferase) (Hooper, M. et al., *Nature* 326:292–295 (1987); Kuehn, M. R. et al., *Nature* 326:295–298 (1987)). Such selected cells can then be used to produce chimeric or transgenic mice which fail to express an active enzyme, and thus provide animal models for diseases.

The ES cells used here were derived from mouse strain 129SvJ and maintained in culture on primary mouse embryo fibroblast (PMEF) feeder cells carrying a neomycin gene. The culture medium was supplemented with leukemia inhibitory factor (1500 units/ml). The targeting vector was linearized by the restriction endonuclease Not I and transfected into the J1 cell line (Li et al. 1992) by electroporation of 3×10$^6$ ES cells. The genetically altered ES cells containing the targeted allele were selected with G418 (Gibco) at 350 μg/ml and Gancyclovir (Bristol Myers) at 0.2 μM.

To screen for homologous recombinant ES clones, genomic DNA was isolated from those clones exhibiting dual resistance (selected against neomycin and Gancyclovir). Genomic DNA was isolated from cultured cells by digestion overnight at 55° C. in lysis buffer (10 mM Tris-HCl, pH 7.5/100 mM NaCl/1 mM EDTA/100 μg/ml proteinase K) followed by precipitation with iso-propanol. The pellet was washed with 70% ethanol and dissolved in 100 μl of 1×TE, pH 8.0 at 55° C. overnight.

Figure 3A:
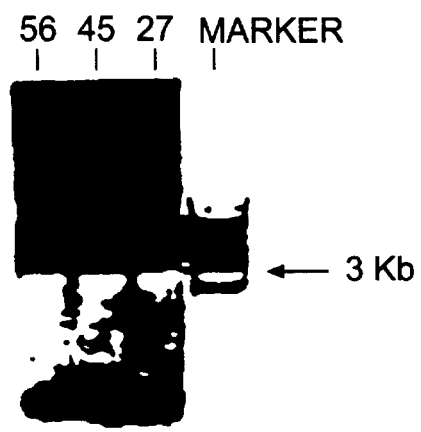
FIG. 3A depicts the PCR analysis of ES cell clones transfected with KSBX.pPNT.
Figure 3B:
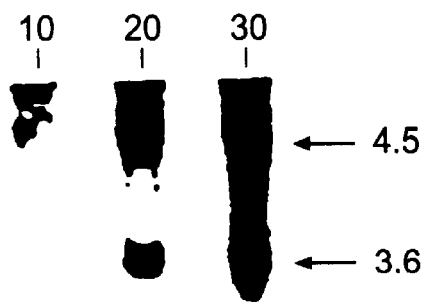
FIG. 3B depicts the southern blot analysis of genomic DNA digested with Xba 1, blotted and hybridized with KXX probe.

The genomic DNA from each clone was used as a template for PCR amplifications with a anx7 specific flanking primer and a PGK-neo-specific primer (5'-CGGATCGATCCCCTCAGAAGAAC-3') (SEQ ID NO:1). Three out of 250 clones yielded a PCR band of the correct size. FIG. 3A depicts the PCR analysis of ES cell clones transfected with KSBX.pPNT. To verify the results of the PCR screening, DNA from PCR-positive ES clones was digested with Xba I and hybridized with a genomic DNA probe, KXX, which is external to the 5'-flank introduced into the targeting vector (See FIG. 3B). The probe detected the predicted 3.6 kb wild-type and 4.5 kb mutant fragments representing the normal and altered alleles of anx7, respectively. Thus, the data indicated that the targeting vector had been successfully generated and that genetically altered heterozygous ES cells had been isolated which had undergone a single targeted integration event at the anx7 locus.

C. Preparation of Chimeras

Figure 4:
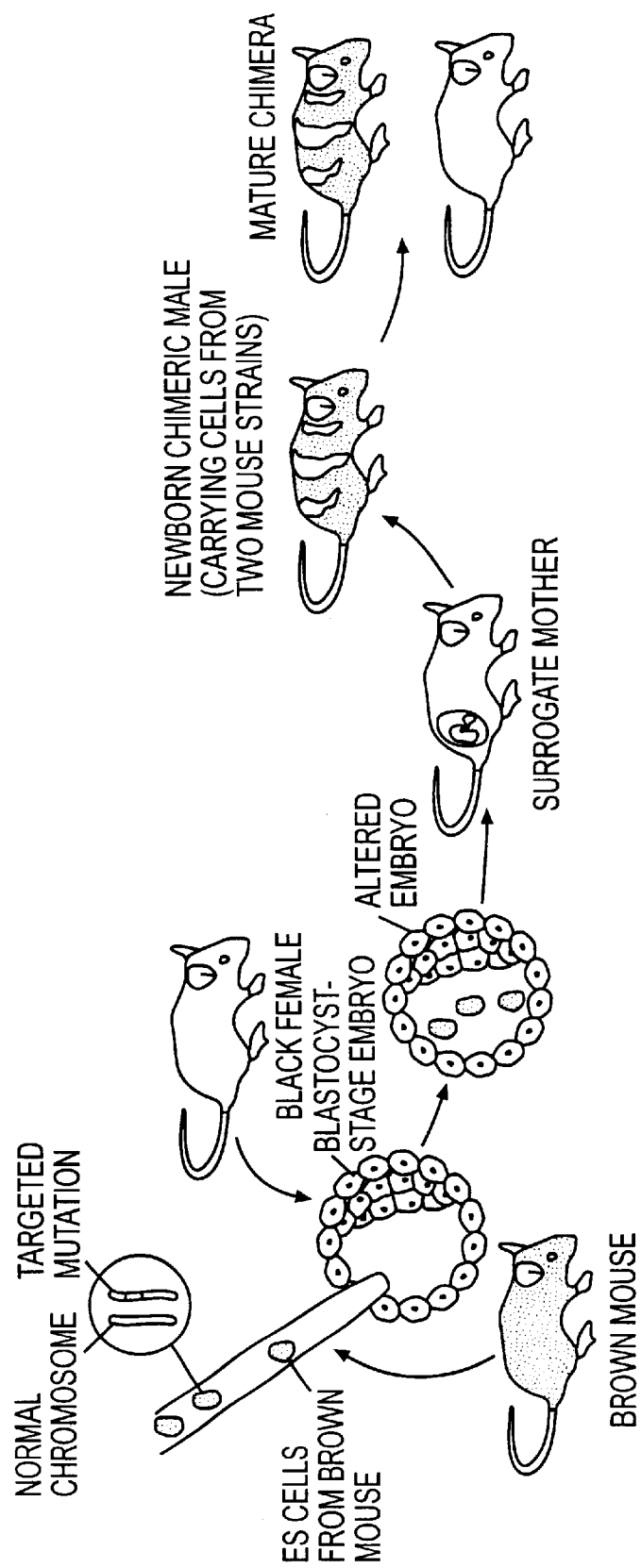
FIG. 4 illustrates a schematic sketch of the generation of chimera.

The strategy for generating the chimeras containing the desired targeted mutation is shown in FIG. 4. In this example, the altered ES cells were microinjected into the blastocoel cavity of a 4.5 day preimplantation mouse embryo from a C57B1/6J mouse. Then, the embryos were transferred surgically into the uterine horn of a pseudopregnant mouse and development was allowed to progress to birth.

Resulting chimeric animals were backcrossed to C57BL6/J mice, and germline transmission was scored by coat color. All agouti (A/A) mice (i.e., brown) offspring were tested for the presence of the mutated anx7 allele by PCR amplification using the same conditions described above for the detection of homologous recombination events in the ES cells. Normally, the ES cells are derived from mice with distinguishable coat color alleles (brown, shown in FIG. 4 as black) compared to recipient blastocyst (black, shown in FIG. 4 as white).

More specifically, ES cells (with targeting construct) derived from an agouti (A/A) mouse (brown) were injected into a recipient nonagouti (a/a) (black female) C57B1/6 blastocyst (See FIG. 5A). Chimeric males and females were mated to non-agouti (black, a/a) females and males, respectively. Any progeny having black coats were excluded immediately. One of the chimeric females gave birth to a brown male mouse and so was a candidate for harboring the chosen mutation in one of the two copies of the anx7 gene in every cell. This chimeric female is illustrated in FIG. 5B: an anx7 transgenic chimeric mouse having an almost entirely agouti brown coat and thus, greater than 95% of the hair follicle cells were derived from the ES cells. Further, since the progeny from this chimeric mouse, when bred to a C57B1/6 black male or black female, were all agouti (brown), it was concluded that most, if not all, of the germline cells produced by this mouse were also derived from the ES cells (FIG. 5C).

Figure 6:
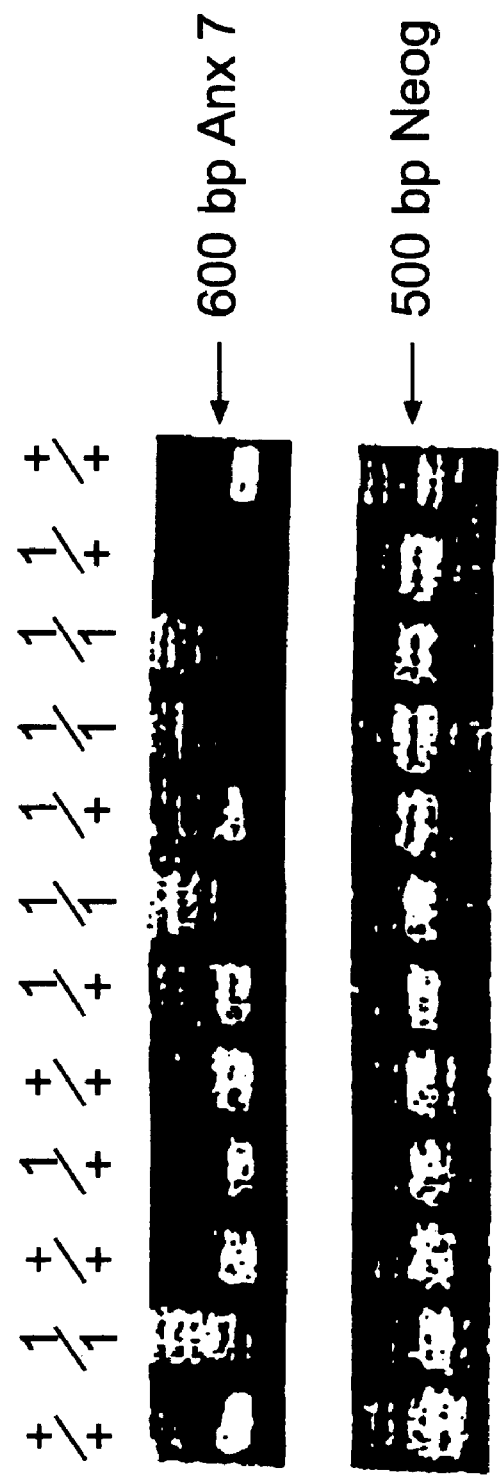
FIG. 6 illustrates the PCR analysis of genomic DNA from yolk sac of anx7(+/+), anx7(+/−), and anx7(−/−) embryos.

Breeding of the chimeras with C57B1/6J strain mice resulted in thirty germ line heterozygotes for the anx7 gene. No anx7(−/−) mutants were found out of 140 pups screened, implying that anx7 deficient mutants die in utero. To investigate the timing of embryonic lethality, mice from embryonic days E8 to E17 were genotyped. Of the viable 120 embryos analyzed, 25% were anx7 (−/−) at E10, but by E11 none of them had survived. The Yolk sac DNA of these embryos was used as a template for PCR analyses as described above. Polymerase chain reaction analysis showed the absence of anx7 transcripts in anx7 (−/−) mutants. (See FIG. 6.)

D. Anatomical and Histological Studies of the Chimeras

Figure 8:
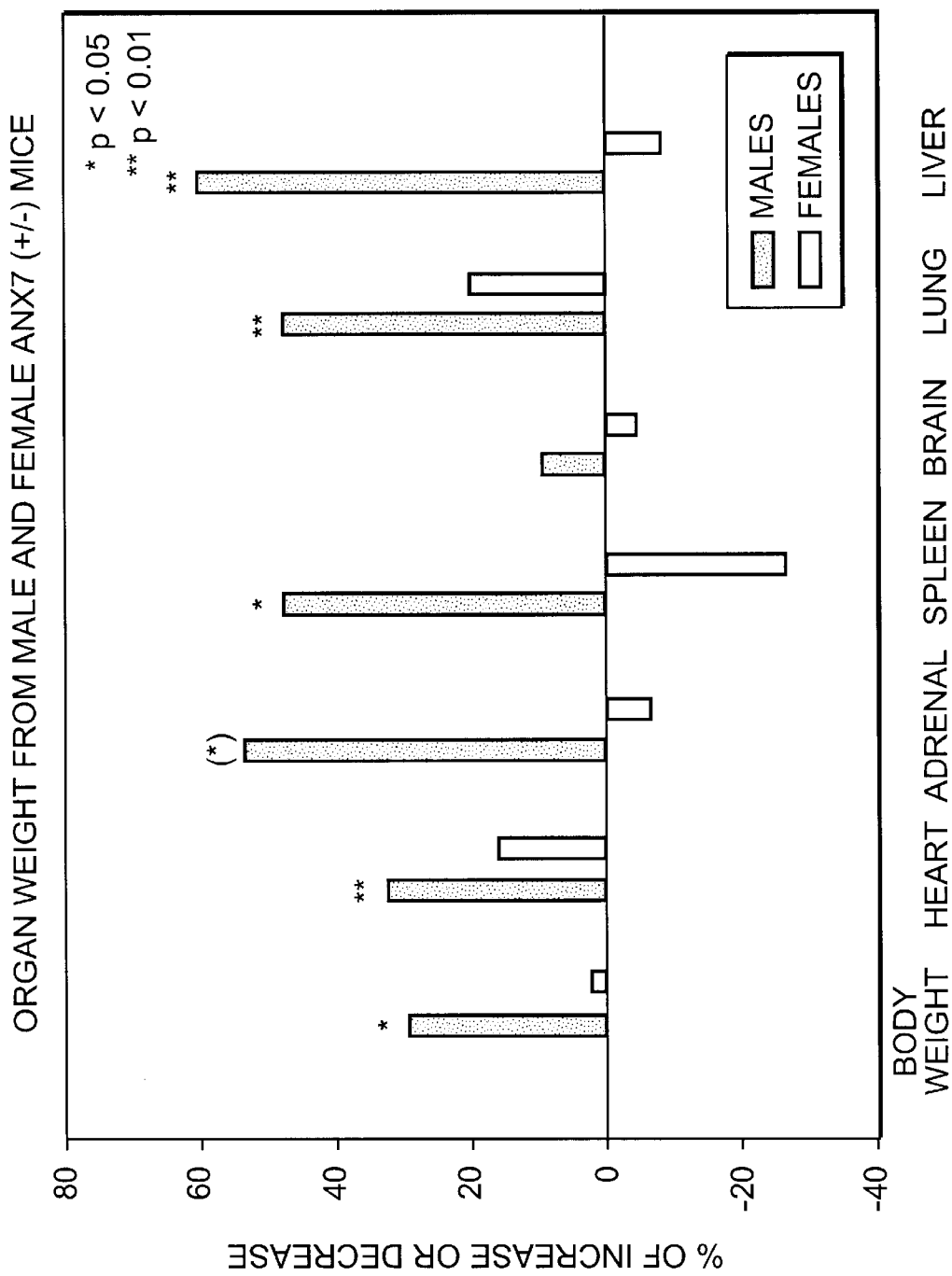
FIG. 8. The percent increase in organ weights of control mice compared with anx7 (+/−) transgenic mice.

Thirty F2 generation hybrids from anx7 (+/−) and anx7 (+/+) mice were weighed at regular intervals. Nine month old anx7(+/−) and anx7(+/+) mice were sacrificed and their internal organs were weighed. The following tissues were fixed in 10% buffered formalin: brain, pituitary, heart, lung, liver, pancreas, adrenals, kidney, spleen and thymus. For pathological studies, these tissues were embedded in paraffin, cut in 5 µm sections, and stained with hematoxylin and eosin. The results are shown in FIG. 8 and discussed below.

Figure 7A:
FIG. 7A illustrates the increased growth of an anx7(+/−) mouse compared with the control mouse.
Figure 7B:
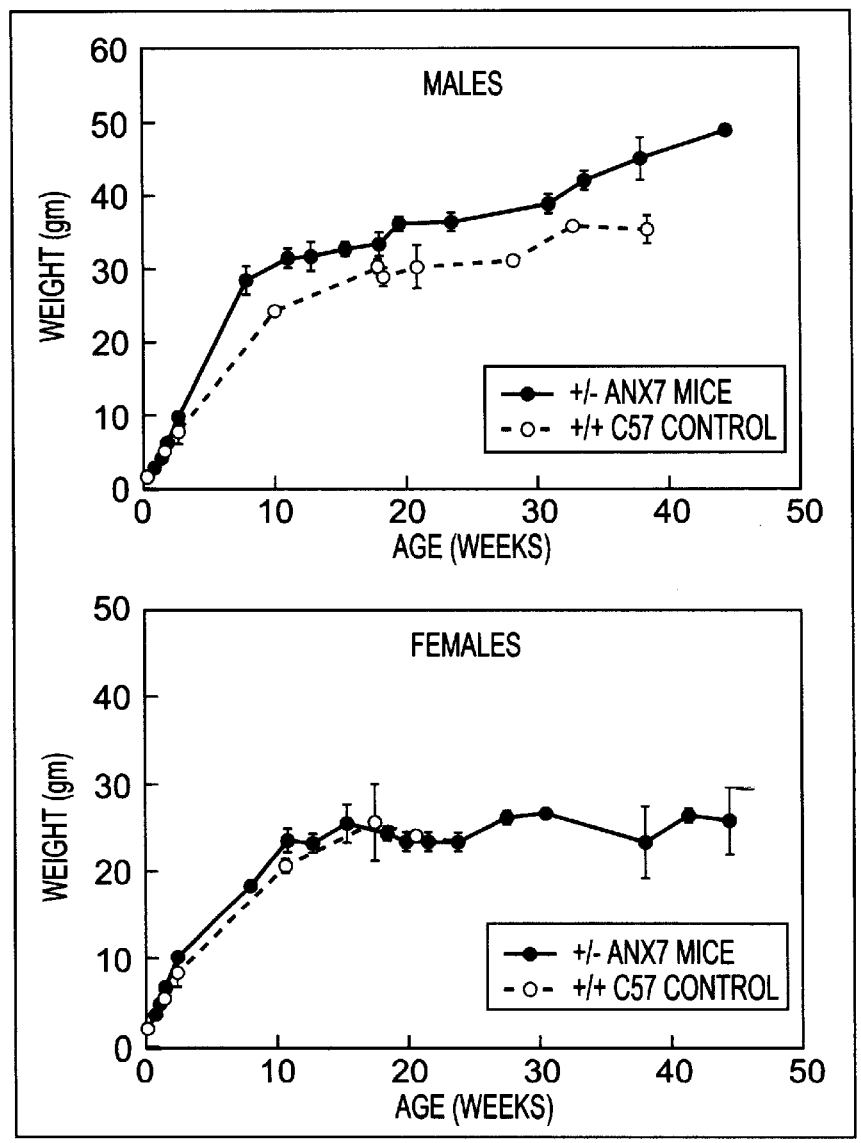
FIG. 7B. Representative growth curve of thirty anx7(+/+) and anx7(+/−) littermates as a function of age.

At birth, the anx7 (+/−) heterozygotes are indistinguishable in size or behavior from wild type littermates or founder mates. However, as shown in FIG. 7A, by 6–8 weeks, the larger male anx7 (+/−) heterozygotes are clearly distinguishable in their relative gigantism from smaller normal. To measure this difference quantitatively, the weights of a set of animals systematically followed (see FIG. 7B). By the 9th month of life, male heterozygotes weighed 40.7±4.4 (SEM, n=5) grams, compared to controls, which were 33.2±2.2 (SEM, n=5) grams. This relative weight increment for males of ca. 25% was statistically significant and not due to obesity. By contrast, no changes were noted in the weight gains with age for females.

Male anx7 (+/−) mice begin to grow at a greater rate than normal littermate controls by about the fourth week after birth. By contrast, female anx7 (+/−) mice do not vary from their controls. Male mutant growth thereafter does not appear to abate. The data in FIG. 7 show growth up to six months of age. However, when these same animals were weighed at 13 months of age, evidence of continued growth over this subsequent time period was noted. Weights as high as 60 grams were noted for some of these heterozygous animals. Postmortem examination has systematically shown that the animals are not fat, but merely large. Organ weight studies performed at 6 months of age showed that many internal organs in anx7 (+/−) males weighed much more than normal, but were of grossly normal structure. It is remarkable that, in light of our subsequent focus on the hyperplastic Islets of Langerhans, the pancreas was one of several organs that were not larger than normal. However, the islets do make up less than 2% of the islet by volume.

The growth phenotype of gender-specific gigantism and organomegaly of the anx7 (+/−) mouse is fundamentally different from that of other reported mouse knockouts. With the exception of the p27$^{kip1}$(−/−) mouse (Fero et al, 1996; Nakayama, K., et al., *Cell* 85:707–720 (1996)), the reported instances of mutation-based gigantism are mostly endocrine in origin, and are due to increases of either growth hormone (Palmiter, R., et al., *Nature* 300:611–615 (1982)), IGF-1 (Mathews, L., et al.,*Endocrinology* 123:2827–2833 (1988)), or IGF-2 (Wolf, E., et al., *Endocrinology* 135:1877–1886 (1994)). However, the levels of serum IGF-1 in the anx7 (+/−) mouse are within normal limits. In addition, since the levels of IGF-1 integrate the pulsatile levels of growth hormone, it was concluded that average GH levels were probably normal as well in anx7 (+/−) mice. GH levels measured in overnight-fasted animals showed no change in males. One qualitative parallel between the growth kinetics of male anx7 (+/−) mice and those mice transgenic for GH or IGF-1, is a postpartum delay in the onset of enhanced growth. The anx7 (+/−) male mice and mice transgenic for GH begin to grow at 3–4 weeks, while those transgenic for IGF-1 begin to grow only after 6–8 weeks. Mice overproducing IGF-2 are heavier than control mice at birth, but do not sustain the increase in weight into adulthood. Finally, pituitary gland histology in male and female anx7 (+/−) mutants cannot be distinguished from wildtype histologies (data not shown). Consistently, the selective distribution of organomegaly noted for the anx7 (+/−) male mutant is distinct from that associated with high levels of GH, IGF-1 and IGF-2 (Palmiter, R., et al., *Science* 222:809–814 (1983); Mathews, L., et al., *Endocrinology* 123:2827–2833 (1988); Quaife, C., et al., *Endocrinology* 114:40–48 (1989); Wolf, E., et al., *Endocrinology* 135:1877–1886 (1994); Ward, A., et al., *Proc. Nat. Acad. Sci.* (*USA*) 91:10365–10369 (1994)), or with the generalized, gender-independent organomegaly reported for the p27kip1 (−/−) mouse. Finally, blood insulin levels in fasting or fed anx7 (+/−) mice were not profoundly different from levels in control animals, indicating that hyperinsulinism is not a viable explanation either. Together, these data thus further validate the conclusion that the documented growth anomalies in the anx7 (+/−) mouse are probably not related to pituitary hyperfunction. The fact that unique growth anomalies in the anx7 (+/−) mouse are gender-specific constitute a further distinct internal genetic control for the anx7 (+/−) mouse mutation.

As further shown in FIG. 8, the increased weight of the anx7 male (+/−) mice was found to occur coincidentally with enlargement of many internal organs. Furthermore, in this separate study, many of the major organs appear to be disproportionately larger than the ca. 25% increment in whole body weights. The most evident example of this situation is the heart, which is nearly 80% heavier than hearts from normal male liftermate controls. The brain is 8% heavier on average than brains in normal controls, but the difference is not statistically significant. Grossly, the male mutants were just large, not fat.

Finally, in an effort to determine whether sexually dimorphic anomalies of growth hormone or other hormones of pituitary origin might explain the male gigantism, we examined the concentrations of IGF-1 and corticosterone in plasma from wildtype and heterozygous animals. However, neither IGF-1 nor corticosterone levels varied between wildtype or mutant when comparing like genders. In addition, the pituitaries of males and females, mutant and normal littermate controls were not found to be histologically different when comparing like genders (n=6, each; data not shown).

EXAMPLE II
Spontaneous Tumors in anx7(+/−) Mice

A total of 50 heterozygous animals, aged 100–200 days, were subjected to a complete post mortem examination, and 10 proved to have histologically verifiable, macroscopic tumors. These tumors occurred in both male and female animals. The tumors found principally included lymphosarcoma of the thymus, insulinoma, and hepatocellular carcinoma. No instance of defined tumors was detected in the control animals.

In a second set of 50 heterozygotes, aged ca. 1 year old, a vastly increased tumor incidence of ca. 50% was detected. In the older animals the principal tumors were also lymphosarcoma of the thymus and hepatocellular carcinoma. In some instances more than one type of tumor was detected in the same animal. In addition, there were several instances of dysplastic thymic organization in otherwise "normal" mutant animals.

Lymphosarcoma of the thymus is a frequently occurring tumor in these mutants. One particularly interestingly example of this tumor is shown in FIG. 9. This tumor was found as an unencapsulated, 1-cm$^3$ tan fleshy mass occupying the anterior thoracic cavity, which surrounded the heart and compressed the lungs. The tumor mass is composed of sheets of monomorphic cells supported by a fine fibrovascular stroma. As shown in FIG. 9B, the cells are small, round, and non-adherent, with well-demarcated borders, scant lightly basophilic cytoplasm, single central round deeply basophilic nuclei, and, generally, a single central prominent nucleolus. There is a moderate mitotic rate, averaging 1/high powered field, and there are numerous large 'tingible body' macrophages which are scattered among the neoplastic cells. At the organismic level the neoplastic cells were found to infiltrate and expand the mediastinum, and to extend into the lung along branches of the pulmonary artery (see FIG. 10B). The tumor effaced the bronchial lymph nodes and was also seen to disseminate to the kidneys (not shown).

Figure 11A:
FIG. 11A. Hepatocellular carcinoma in liver tissue from a control littermate of an anx7 (+/−) mouse.

Although less frequently found than the lymphosarcoma, the hepatocellular carcinomas are remarkable by their size. The hepatocellular carcinoma shown in FIG. 11 is an unencapsulated mass (1×0.5×0.5 cm) composed of large polygonal cells arranged in cords and trabeculae. The mitotic rate is less than 1/10 high power fields. Cells have discrete cytoplasmic borders, abundant granular to finely vacuolated eosinophilic cytoplasm and a large centralized round vesicular nucleus. In most cells there is a single prominent magenta nucleolus, although occasional nuclei contain multiple nucleoli. Neoplastic cells are observed to infiltrate adjacent hepatic parenchyma.

(1) Example of Lymphosarcoma of the Thymus:

A section from a lymphosarcoma of the thymus, taken at 50-× magnification, is shown in FIG. 9B, with a sample of normal thymus shown in FIG. 9A for comparison. The board certified veterinary pathologist's description is as follows:

Description of thymic mass in mouse, MS9801634: There is a 1 cm$^3$ tan fleshy mass occupying the anterior thoracic cavity, surrounding the heart and compressing the lungs. The mass is composed of sheets of monomorphic cells supported by a fine fibrovascular stroma. The cells are small, round, and non-adherent, with well demarcated borders, scant lightly basophilic cytoplasm, single central round deeply basophilic nuclei and generally a single central prominent nucleolus. There is a moderate mitotic rate, averaging 1/high powered field. Numerous large 'tingible body' macrophages are scattered among the neoplastic cells. The mass is unencapsulated. Neoplastic cells infiltrate and expand the mediastinum, extend into the lung along branches of the pulmonary artery, efface the bronchial lymph nodes, and disseminate to the kidneys. Cell morphology is consistent with lymphosarcoma.

A section is shown of tumor cell infiltration into the lung in FIG. 10B, in which extensions along branches of the pulmonary artery are prominent. For comparison, control lung from an anx7(+/+) mouse is shown in FIG. 10A. In many other examples of lymphosarcoma of the thymus, metastases to the pancreas have been frequently noted.

Figure 11B:
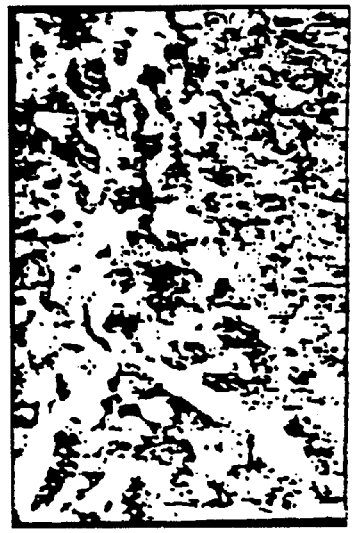
FIG. 11B. Hepatocellular carcinoma in liver tissue from an anx7 (+/−) mouse.

(2) Example of Hepatocellular Carcinoma:

A section from a hepatocellular carcinoma, taken at 100-× magnification, is shown in FIG. 11B. For comparison a sample of normal liver from an anx7(+/+) mouse shown in FIG. 11A. The board certified veterinary pathologist's description is as follows.

Description of mass (1×0.5×0.5 cm) from (region around liver of) mouse MS9901058: . . . is composed of large polygonal cells arranged in cords and trabeculae. Cells have discrete cytoplasmic borders, abundant granular to finely vacuolated eosinophilic cytoplasm and a large centralized round vesicular nucleus. In most (cells) there is a single prominent magenta nucleolus; occasional nuclei contain multiple nucleoli. The mass is unencapsulated and neoplastic cells infiltrate adjacent hepatic parenchyma. The mitotic rate is less than 1/10 high power fields.

Cell morphologies are consistent with lymphosarcoma of the thymus and hepatocellular carcinoma, respectively. Since other types of tumors have also been detected, albeit with lesser frequencies, it would appear that the anx7 (+/−) phenotype is not expressed as an obvious preference for one tumor type to the exclusion of others. The wild type human anx7 gene suppresses growth of a variety of human tumor cell lines.

EXAMPLE III
Determination of Levels of ANX7 Protein in Tissues from anx7 (+/−) Mouse As noted above, certain organs (e.g., heart and pancreatic islets) in the anx7(+/−) mouse exhibit organomegaly. Tissues from anx7 (+/−) and control mice were harvested, frozen on dry ice, and then homogenized in boiling SDS buffer, and then assessed for ANX7 protein. Aliquots containing identical amounts of protein were separated by SDS-PAGE, transblotted to nitrocellulose, and ANX7 visualized using rabbit anti-ANX7 primary antibody, HRP-conjugated secondary antibody, and ECL detection on X-Ray film.

Figure 13:
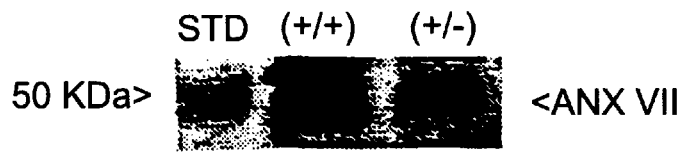
FIG. 13 depicts EM pictures showing pancreatic P-cells from anx7 (+/−) and control (+/+) littermates.

As shown in FIG. 13, ANX7 levels in the pancreas of male anx7 (+/−) mice contain 20–30% of the ANX7 levels in pancreatic tissue from control animals. Heart tissue was also run in parallel, with similar results. ANX7 from heart has a tissue-specific cassette exon edited into the higher molecular weight edited product.

ANX7 levels appear to be much lower in mutant than in control pancreas, heart, and other tissues. Tissue specific editing processes do not appear to influence the lower expression levels in mutant mice. Thus the remaining intact copy of the anx7 gene in the anx7(+/−) mouse appears to be unable to compensate for the loss of function of the knocked out allele.

EXAMPLE IV
Production of Recombinant Adenovirus Expressing Wild Type and Mutant anx7 for Gene Therapy Compared with the chemically based gene transfer systems, the adenovirus system is more efficient and quantitative for introducing specific genes into cells. Adenovirus recombinants of anx7 sense, anti-sense, and mutations are constructed by cotransfection into human embryonic kidney cells (HEK293) with a replication-deficient adenovirus vector, QBI-Ad5 (Quantum Biotechnologies, Inc., Laval, Quebec, Canada). In the HEK293 cells recombinant adenoviral vectors containing the anx7 cDNA sequence are formed by homologous recombination. HEK293 cell lysates from approximately 20 plaques per construct are analyzed for recombinant virus by PCR, using primers from the anx7 cDNA. Cell lysates from plaques that are positive by PCR analysis are then further characterized for expression of ANX7 protein by Western blot analysis. Plaques that express ANX7 robustly are further plaque-purified and isolated in higher titer from HEK293 cells for further experiments.

Wild type and mutant anx7 genes are engineered into replication-deficient adenoviral vectors, and adenoviral particles prepared, purified, titered, and systematically tested by administration to HEK293 cells. A variety of wild type and mutant anx7 genes have been prepared in the adenovirus vector, and many have been expressed as recombinant adenoviral particles. The anx7 mutations, not shown here, include 16 combinations of the mutated calcium binding sites in the four repeats; two site directed mutations against protein kinase C sites; five mutations directed against GTP binding sites; and an antisense anx7 construct.

EXAMPLE V
Production of Dominant Negative Mutants of ANX7

Dominant negative mutants of tumor suppressor genes have been useful for investigating the mechanism of action of tumor suppressor genes. An alternative approach to study the role of the tumor suppressing anx7 gene is to use mutated anx7 constructs with dominant negative activity to suppress the function of endogenous anx7 gene. "Dominant negative" genes encode abnormal proteins that repress the function of their normal counterparts in a dominant manner. Thus, one way to examine the role of anx7 is to utilize "dominant negative" mutant constructs that would suppress normal ANX7 function in wild type cells and then determine if the expression of these constructs would alter the growth and differentiation, especially under $Ca^{2+}$ limiting conditions.

In order to construct these dominant negative mutants, mutations at some or all of the four $Ca^{2+}$ binding sites on ANX7 were chosen as the sites of mutational events. Using standard techniques, site directed mutations were introduced into the calcium binding sites in combinations of all four crystallographically defined endonexin fold motifs. All four have the consensus sequence [GXGTDE] (SEQ ID NO:2) and the mutations were engineered to generate the amidated analogues of the charged residues (viz [GXGTNQ]) (SEQ ID NO:3). Thus, 16 different combinations were prepared, including the wild type ANX7. The combinations were single mutations (e.g., 1, 2, 3 & 4); mutations at two sites (e.g., 1 & 2, 1 & 3, etc.) mutations at three sites (e.g., 1&2&3, 2&3&4, etc.) and all four sites (e.g., 1&2&3&4).

Figure 14:
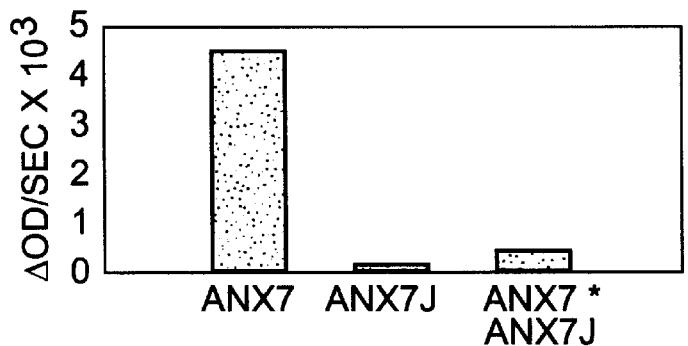
FIG. 14 depicts the dominant negative activity of ANX7J mutant when mixed with wild typ ANX7 in an in vitro membrane fusion assay.

All the mutants were prepared and tested in the phosphatidylserine liposome fusion assay (Couhay, et al., Proc. Nat. Acad. Sci. (USA) 93:10797–10802 (1996)). Some were as active as the wild type, while others were much less active. As shown in FIG. 14, one mutant, ANX7J, was both intrinsically inactive, and profoundly inhibitory when mixed with equi-molar amounts of wild type ANX7 (viz., 1 μg each of ANX7 proteins). Thus, ANX7J behaves as a dominant negative mutant in the in vitro test.

EXAMPLE VI
Human ANX7 as a Target for Protein Kinases, in Vitro and in Vivo

Threonine/serine protein kinases such as Protein Kinase C (PKC) and tyrosine kinases are known to phosphorylate tumor suppressor genes such as p53 or BRCA1, respectively. For in vitro tests, purified recombinant ANX7 is mixed with purified protein kinases, and assays performed. For in vivo tests, agonists for specific receptors are mixed with cells, and endogenous ANX7 labeling is detected.

Figure 15:
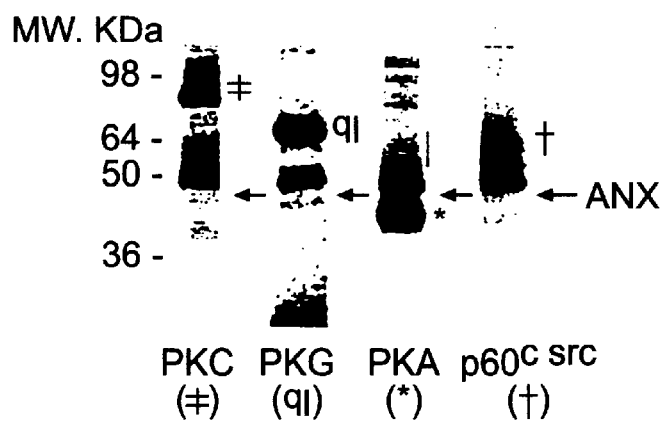
FIG. 15 depicts the phoshorylation of ANX7 by different protein kinase subunits.

A series of purified protein kinases were tested for in vitro activity on recombinant ANX7. These included protein kinase C (PKC), cAMP-dependent protein Kinase (PKA), cGMP-dependent protein kinase (PKG), Casein kinase I and casein Kinase II, $Ca^{2+}$/calmodulin Kinase II, and the tyrosine kinases, p60$^{src}$ and epidermal growth factor receptor kinase (EGFR-kinase). The assays determined the molar ratio of $^{32}$[P]/ANX7 protein after a 30-minute incubation under the best experimental conditions. As partially summarized in FIG. 15, of the enzymes tested, only five were active. These were PKC (molar ratio=2.0), PKG (molar ratio=1.0), PKA (molar ratio=1.0), p60$^{src}$ (molar ratio=1.0), and EGFR kinase (molar ratio not determined). ANX7 activity in a $Ca^{2+}$-dependent membrane fusion assay was vastly potentiated by PKC treatment of the ANX7. One of two candidate PKC sites on ANX7 were selected and mutated from serine (S) to alanine (A), with substantial loss of activity. By contrast, no activity was detected when recombinant ANX7 was exposed to casein kinase I, casein kinase II, or $Ca^{2+}$/calmodulin kinase II.

To test for PKC phosphorylation under in vivo conditions, chromaffin cells were equilibrated with $^{32}$[P] to label endogenous ATP, and exposed to phorbol-12-myristate-13-acetate (PMA) to activate PKC. Substantial $^{32}$[P]-labeled endogenous ANX7 was detected by immunoprecipitation, which was blocked by specific PKC inhibitors.

In addition, at the in vivo cellular level, we also asked whether endogenous ANX7 might be labeled when human adenocarcinoma A431 cells were exposed to either epidermal growth factor (EGF) or platelet derived growth factor (PDGF). In both cases substantial levels of $^{32}$[P]-labeled endogenous ANX7 were detected by immunoprecipitation.

Thus, ANX7 can be labeled by a broad spectrum of protein kinases, both in vitro and in vivo. The exceptions of casein kinases I and II serve to distinguish ANX7 from p53 types of target molecules.

EXAMPLE VII
GTP-binding Site Mutations in Human anx7

ANX7 is a $Ca^{2+}$-activated GTPase, which contains the five putative RAS-type canonical GTP binding sites. Since it was not known prior to these experiments which mutations in these GTPase domains might be important for ANX7 activity, mutant ANX7's containing discrete site-directed RAS-like mutations were constructed and expressed. These mutations were G-2 (QinT); G-4 (NRsN); and G-5 (EiSG). Binding of 8-azido-GTP could then be used to assess GTP binding.

The wild type and mutant ANX7 proteins were expressed in the pTrc99A expression system in E. coli, and purified to ca. 90% by differential ammonium sulfate precipitation and column chromatography on Ultragel AcA54 (see Cauhuy et al, 1996 for more details). Specific ANX7 protein content of the 47 KDa or the 51 KDa bands were estimated by using the $^{125}$[I] anti-mouse IgG secondary antibody to label transblotted samples on nitrocellulose that had been bound by primary monoclonal antibody 10E7. ANX7 and ANX7 mutants were photolabeled by 8-$N_3$-$^{32}$[P]-GTP in the presence of 2 mM glutathione to block non-specific binding.

Western blots and protein blots showed that substantial amounts of mutant proteins could be prepared. The PhosphoImager data reveal that the LI mutation entirely blocks GTP binding, while NI, TA1 and FL mutants are approximately 60% active. By contrast, the TA2 mutation is approximately 50% activated. "FLS" represents recombinant full-length anx7, or ANX7. The TA1 and TA2 mutations are in a higher molecular weight ANX7 isoform containing the cassette exon #6, and for that reason run slower on the SDS gel. In RAS, the equivalent LI mutation prevents GTP from binding, just as it does in ANX7.

These data serve to validate the structural basis of the intrinsic GTPase activity of ANX7.

EXAMPLE VIII
Culture and Assay of Tumor Suppressor Gene Activity in Tumor Cell Lines Suppression of Human Tumor Cell Proliferation by Human anx7 Gene Tumor cell lines can be grown in vitro, and this growth is suppressed when wild type tumor suppressor genes are transfected into the tumor cells (e.g., Greenblatt, M. S., et al., Mutations in the p53 Tumor Suppressor Gene: Clues to Cancer Etiology and Molecular Pathogenesis, *Cancer Res.*, 54:4855–4878 (1994)). For example, certain human prostate tumor cell lines can be suppressed when a mutated Rb gene is supplanted by a wild type Rb gene (Huang, H. J-S., et al., *Science* 242:1563–1566, (1988); Bookstein, R., et al., *Science* 247:712–715, (1990)). Equivalent results have been reported for a human bladder carcinoma cell line (Takahashi, R., et al., *Proc. Nat. Acad. Sci. (USA)* 88:5257–5261 (1991)). Similar reports have also been made for the p53 gene (e.g., Eliyahu, D., et al., *Proc. Nat. Acad. Sci. (USA)*, 86:8763–8767 (1989); Finlay, C. A., et al., *Cell* 57:1083–1093 (1989); Isaacs, W. B., et al., *Cancer Res.*, 51:4716–4720 (1991)). Specific examples include suppression of growth of human colorectal cancer cells (Baker, S. J., et al., *Science* 249:912–915 (1990)) and human prostate cancer cells lines such as LNCaP and DU145 (Srivastava, S., et al., *Nature* 348:747–749 (1998)). Although many susceptible tumor cells contain p53 mutations, it is even possible to suppress the growth of cancer cells with transfected p53 which contain endogenous wild type p53 (Clayman, G. L., et al., *Cancer Res.* 55:1–6 (1995); Katayose, D., et al., *Clin. Cancer Res.* 1:889–897 (1995)). With the transfection paradigm, it is possible to raise wild type p53 levels as high as 100-fold over control expression levels.

Cells were obtained from the ATCC and handled as follows:

Prostate cancer cell line DU145 was cultured in Eagle's Minimum Essential Medium with 2 mM L-glutamine and Earle's BSS, adjusted to contain 1.5 g/L sodium bicarbonate, 0.1 mM non-essential amino acids, 1.0 mM sodium pyruvate (Sigma Chemical Co., St. Louis, Mo. ), and 10% fetal bovine serum (Intergen Co., Purchase, N.Y.).

Prostate cancer cell line LNCaP was cultured in RPMI 1640 medium with 2mM L-glutamine adjusted to contain 1.5% sodium bicarbonate, 4.5 g/L glucose, 10 mM HEPES, 1.0 mM pyruvate (Sigma Chemical Co.), and10% fetal bovine serum (Intergen Co., Purchase, N.Y.).

Osteosarcoma cell line Saos-2 was cultured in McCoy's 5a medium with 1.5 mM L-glutamine (Sigma Chemical Co.), and 15% fetal bovine serum (Intergen Co., Purchase, N.Y.).

Breast cancer cell line MCF7 was cultured in Eagle's Minimum Essential Medium with 2 mM L-glutamine and Earle's BSS adjusted to contain 1.5 g/L sodium bicarbonate, 0.1 mM non-essential amino acids, 1.0 mM sodium pyruvate (Sigma Chemical Co., St. Louis, Mo.), 0.01 mg/ml bovine insulin (Life Technologies Inc.), and 10% fetal bovine serum (Intergen Co., Purchase, N.Y.).

Cells were plated in 6-well plates (35 mm wells) and grown in appropriate media to approximately 70% confluency for transfection in media appropriate to the cell type. Transfection parameters were initially optimized using a plasmid expressing β-galactosidase. These studies suggested that 2–4 ug plasmid DNA and 6 ul lipofectamine would produce maximum transfection efficiency. Cells were therefore transfected for 5 hrs with various amounts (1–6 ug) of several plasmids (pcDNA3.1 alone obtained from or containing/expressing cDNA encoding human anx7, p53 or NMDA receptor subunit 2C) and lipofectamine (6 ul; Life Technologies Inc., Grand Island, N.Y.) in reduced serum medium (Optimem 1, Life Technologies Inc.) essentially as recommended by the supplier.

Approximately 36 hrs later, selection with G418 (Genetic, Life Technologies Inc.) at 800 ug per ml medium was initiated. Cells were then maintained with medium changes every 3–4 days, always containing G418. After approximately 1 week of G418 selection, most non-transfected cells had died. After approximately 2 weeks of selection, when many macroscopic colonies could be seen in wells transfected with pcDNA3, the cells were rinsed with phosphate-buffered saline (PBS), fixed with 2% formaldehyde in PBS for 15 min, stained with 0.5% crystal violet in PBS for 15 min and rinsed 1–2 times with distilled $H_2O$, dried and stored for subsequent quantification of colonies. Colonies visible in each well without magnification were counted and average values (mean+standard error of the mean) were determined for wells transfected with each concentration of each plasmid.

As shown in FIG. 12, all four tumor cell lines are suppressed in a DNA-dose dependent manner by both anx7 and p53, but not by the vector controls. Two prostate tumor cell lines, DU145 (FIG. 12A) and LNCaP (FIG. 12B), a breast cancer cell line MCF-7 (FIG. 12C), and an osteosarcoma cell line (Saos-2) (FIG. 12D), were transfected with the vector alone or the vector expressing anx7 (+anx7) or a vector expressing p53 (+p53).

EXAMPLE IX

State of anx7 mRNA and ANX 7 Protein During Cell Cycle in Human Fibroblasts

Tumor suppressor genes are principally known for control of cell proliferation by their action on different aspects of the cell cycle. To determine whether anx7 plays a role in this process, it is crucial to know the state of anx7 mRNA and ANX7 protein as a function of position in the cell cycle of untransformed cells. The state of anx7 mRNA and ANX7 protein in human IMR-90 fibroblasts can be studied by the serum-deprivation/addition method to synchronize the cell cycles, and changes occurring during this period can then be studied.

(1) Cells, cell cycle assays, and immunodetection:

IMR-90 cells, obtained from the ATCC, were cultured and synchronized by serum deprivation to arrest the cells in $G_o$, and then activation by serum addition, as described by Raynal et al. (1997) (See above). Progression through the cell cycle was followed by $^3$[H]-thymidine incorporation (5 $\mu$Ci/ml) over a 4 hour period and by monoclonal immunodetection of cdc-2 (Zymed). ANX7 was detected with a polyclonal rabbit anti-ANX7 antibody against a conserved internal ANX7 peptide, (RDLEKDIRSDTSG) (SEQ ID NO:4). Detection was on the basis of $^{125}$[I]-second antibody and Molecular Dynamics PhosphoImager quantification. Our own recombinant ANX7 was used to standardize the assays.

(2) Analysis of mRNA:

For construction of an anx7 RNAse protection assay, templates were constructed using a PCR amplification kit (Perkin-Elmer Cetus, Norwalk, Conn.), with a primer set as described by Raynal et al (1997). RNAse protection assays were analyzed by separating the products by denaturing PAGE and autoradiography.

Confluent human IMR-90 fibroblasts are incubated for 72 hours in a serum-free medium, and 10% serum is added at time zero to activate the cell cycle. As shown in the Raynal, et al (*Biochem. J.* 322:365–371 (1997), incorporated by reference), cdc2 (a.k.a., cdk2) synthesis is followed by immunoblotting to mark the G2/M-phase, while DNA synthesis to mark the S-phase is followed by incorporation of $^3$[H]-thymidine. The relative expression of ANX7 over the cycle period is determined by Western blot analysis. Other annexins serve as controls for the experiment of Raynal et al.

There is a small but significant reduction of ANX7 protein levels at the transition between S and G2/M. However, anx7 mRNA levels do not vary appreciably over the entire cell cycle.

EXAMPLE X

Methods for Determining Polymorphism or Mutation in the anx7 Gene (1) Analysis of RNA Transcripts Matched tumor and adjacent normal tissues from mice and human are obtained and immediately embedded in OCT (Miles Inc. Diagnostics Division Elkhart, Ind.) and frozen at −70° C. With LCM (laser-gene capture microdissection) of tumor and normal cells are obtained from a heterozygous mouse and human specimens. Using a cryotome, 1.0-micron sections are cut from frozen tissues and stained by hematoxylin (H) and eosin (E). The H & E slides are read by the pathologist to ensure the presence of >70% tumor cells. The neoplastic area are outlined on each slide. The unstained frozen sections on the slides are stored at −70° C. until DNA was extracted. The H&E stained slides are used as a template and corresponding frozen sections will be superimposed on it. The normal and tumor cells dissected by LCM are used for RNA extraction and purification by Ransom B reagent (Tel-Test, Inc., Friendwood, Tex.). Tumor and normal tissue RNAs are reverse-transcribed using random hexamers and Superscript (Life Technology, Gaithersburg, Md.). Five CDNA fragments representing the complete anx7 protein coding sequence are amplified using pfu DNA polymerase. Since pfu DNA polymerase has proof-reading activity, it is less error prone as compared to Taq DNA polymerase. The PCR fragments are subjected to "Cold SSCP" with temperature optimized for each fragment. Aberrant bands from SSCP gels are reamplified and sequenced.

(2) Analysis of Allelic Loss at the anx7 Gene Locus in the Tumor Samples

Defined areas of the tumor cells are scraped with a fresh razor blade, taking care not to scrape adjacent normal tissues as described above. The scraped tissue are digested with proteinase K, extracted with phenol/chloroform, followed by ethanol precipitation. The integrity and concentration of genomic DNA from frozen tissue is determined on agarose gels. The matching normal DNA is extracted from histologically normal tissue sections that did not contain tumor cells. To detect polymorphism and deletions in the anx7 locus, Southern blot analysis is carried out using high molecular weight DNA digested with restriction enzymes. The bands are fractionated by electrophoresis on 0.6% agarose gel and transferred onto nylon membranes. The nylon membranes are hybridized with nick translated cDNA anx7 probe. The polymorphic changes in the disease samples are then analyzed.

(3) PCR and Polymorphism Analysis

Primers flanking the dinucleotide repeat sequences have been identified in the anx7 gene (Shirvan et al., 1994). The PCR is performed on the genomic DNA samples using the following conditions: 5 nanograms (ng) of DNA template, 50 ng of each primer, 0.5 unit of AmpliTaq Gold (Perkin Elmer Emeryville, Calif.), 1×PCR buffer, 200 $\mu$l dNTP mix in a 50 $\mu$l final volume. PCR conditions are identical for all primers used. PCR cycles includes 1 cycle of 95° C. for 10 min. followed by 25 cycles of 95° C. for 30 sec., 55° C. for 45 sec. and 72° C. for 1 min. One of the primers is end labeled using $^{32}$P-ATP and T4 polynucleotide kinase kit (Life Technology, Gaithersburg, Md.). Each locus exhibiting allelic loss/gain is co-amplified with β-actin to ascertain that we have used similar amounts of the input DNA in PCR reactions. Human placental DNA is used as a positive control for PCR reactions. For samples which will be analyzed by radioactive methods, PCR products are subjected to electrophoresis on a 7% acrylamide/urea/formamide gel. The gel is dried and processed for autoradiography.

(4) Mutational Analysis of anx7 by "Cold SSCP"/DNA Sequencing

PCR products representing anx7 cDNA are denatured with methyl mercury hydroxide and electrophoresed through pre-made 20% polyacrylamide minigels (Novex) at a high voltage and a constant temperature. Temperature of the buffer and gel is accurately maintained by constant temperature water circulation through a specially designed cooling system. It is also important to point out that SSCP is more sensitive than direct DNA sequencing in detecting mutant anx7 alleles in the presence of wt anx7 sequences. These wt anx7 sequences are unavoidably present due to the presence of normal cells in tumor tissue architecture, or due to tumor cell heterogeneity where all the cells in tumor tissue may not contain anx7 mutations. It is difficult to make a call for mutation by direct DNA sequence analysis of PCR products containing 30% or less of the mutant allele in the presence of wt sequence. However, due to mobility shifts of the mutant alleles in SSCP, ~10% mutant alleles are confidently detected in the large excess of the wt allele. Once the mutant conformation is identified it can be isolated from the SSCP gel and selectively amplified for DNA sequencing. These issues are especially relevant for tumor DNAs from primary samples of cancer, where tumor heterogeneity is well recognized. Silver staining or SYBR green staining of the gels, are responsible for the increased sensitivity of detection of SSCP bands on gel. The aberrant SSCP bands identified by "Cold SSCF" procedure are cut from the gel and reamplified using the same primers. PCR products are purified and sequenced using the (Rhodamine-terminator cycle sequencing kit (PE Applied Biosystem) following the supplier's recommended methods. DNA sequences are analyzed on an automated DNA sequencer (310 Genetic Analyzer, Applied Biosystem).

(5) Assessment of LOH

After PCR, LOH "Loss of Heterozysosity" of tumor samples will be initially determined visually by comparing the intensity of bands representing the alleles between normal DNA and tumor DNA. A decrease of >50% signal intensity in tumor DNA, as compared to normal, on more than one of the alleles in tumor DNA is scored as LOH. Quantitation is undertaken by exposing the dried gels to phosphor storage screens for 4–5 hours and images are collected on a Molecular Dynamics Phosphorimager and analyzed with Image Quant software (Sunnyvale, Calif.). Quantitation is done by subtracting the background and by the volume integration method within equal-sized rectangular regions that are placed manually over bands.

EXAMPLE XI

Levels of ANX7 Protein Expression in Human Prostate Tumor Tissue Micrarrays

Figure 16A:
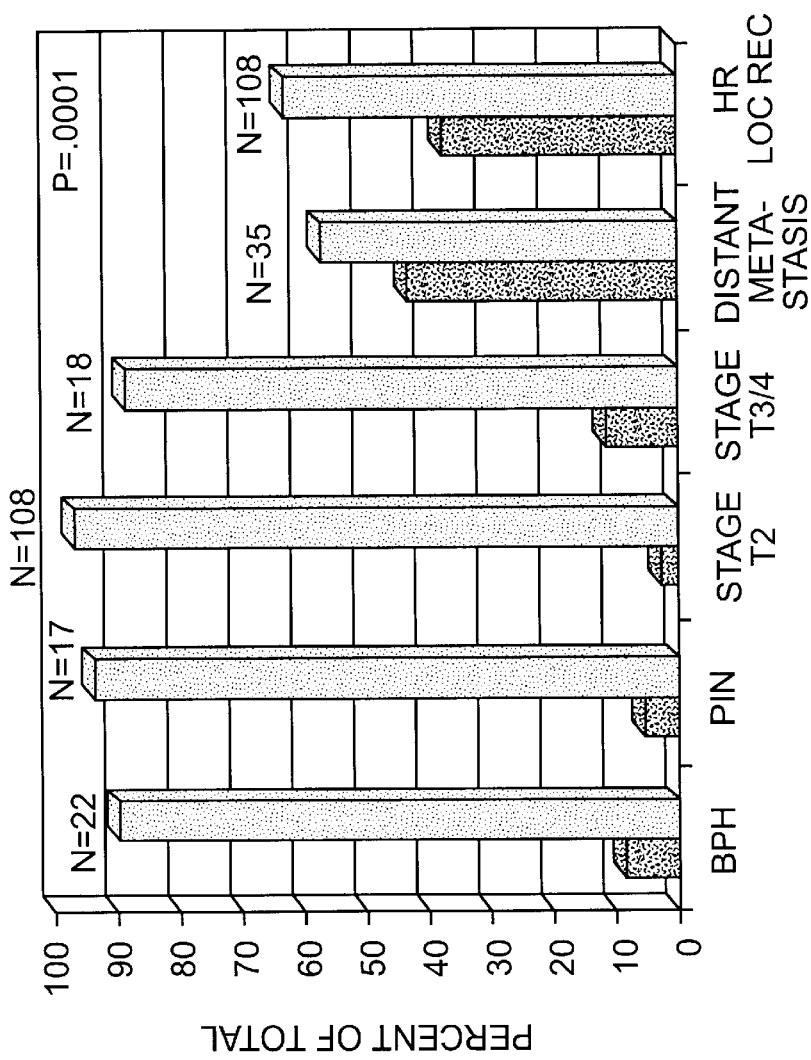
FIG. 16A depicts the frequency of ANX7 expression in a stage specific manner in a prostate tissue microarray containing 301 specimens from all stages of human prostate tumor progression.
Figure 16B:
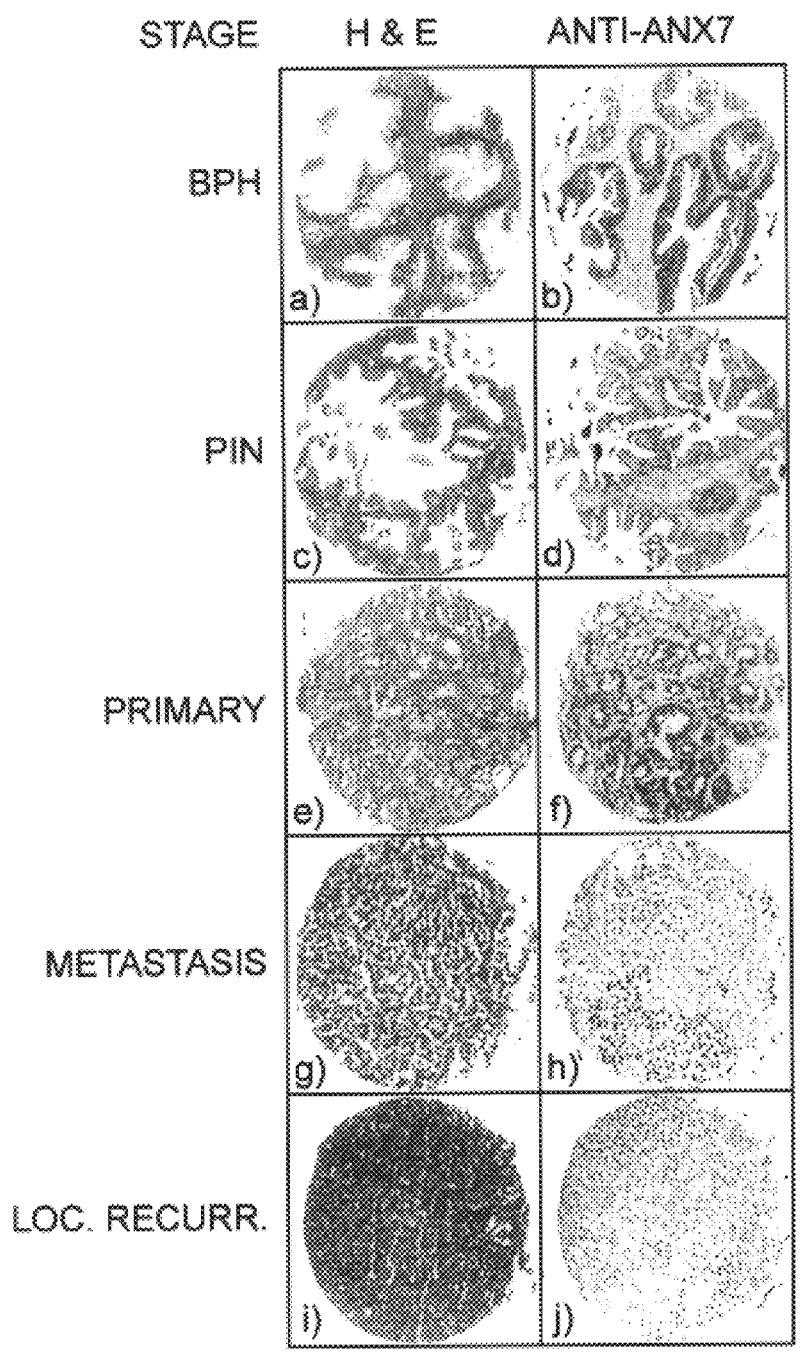
FIG. 16B depicts H&E stained sections (left side) and brown diaminobenzidine (DAB) stain from an anti-ANX-7 monoclonal antibody immunostaining (right side) of typical examples taken from samples of the human tumor microarray shown in FIG. 16A. (BPH—benign prostatic hypertrophy; PIN—primary intraepithelial neoplasms.)

We determined the level of ANX7 protein expression in a prostate tissue microarray containing 301 specimens taken from all stages of human prostate tumor progression. As shown in FIG. 16A, significant reductions in ANX7 expression were found to occur in a stage-specific manner. ANX7 expression was completely lost in a high proportion of metastases (57%) and in local recurrences of hormonal refractory prostate cancer (63%). By contrast, ANX7 occurs at close to normal levels in benign prostate glands, high grade prostatic intraepithelial neoplasms (PIN), and stage T2 and T3/4 primary tumors (all in the range of 89–96%). In FIG. 16B, typical examples taken from samples used in the human tumor microarray were stained with H&E (left side) and brown diaminobenzidine (DAB) using an anti-ANX-7 monoclonal antibody (right side). (BPH—benign prostatic hypertrophy.) The top three sections are heavily stained, while the bottom two sections, representing metastatic and locally recurrent tumors, respectively, are negative. The p value for stage-specific loss is p=0.0001. This visual comparison reinforces the statistically significant lack of ANX7 in the two worst prognostic situations.

EXAMPLE XII

Figure 17A:
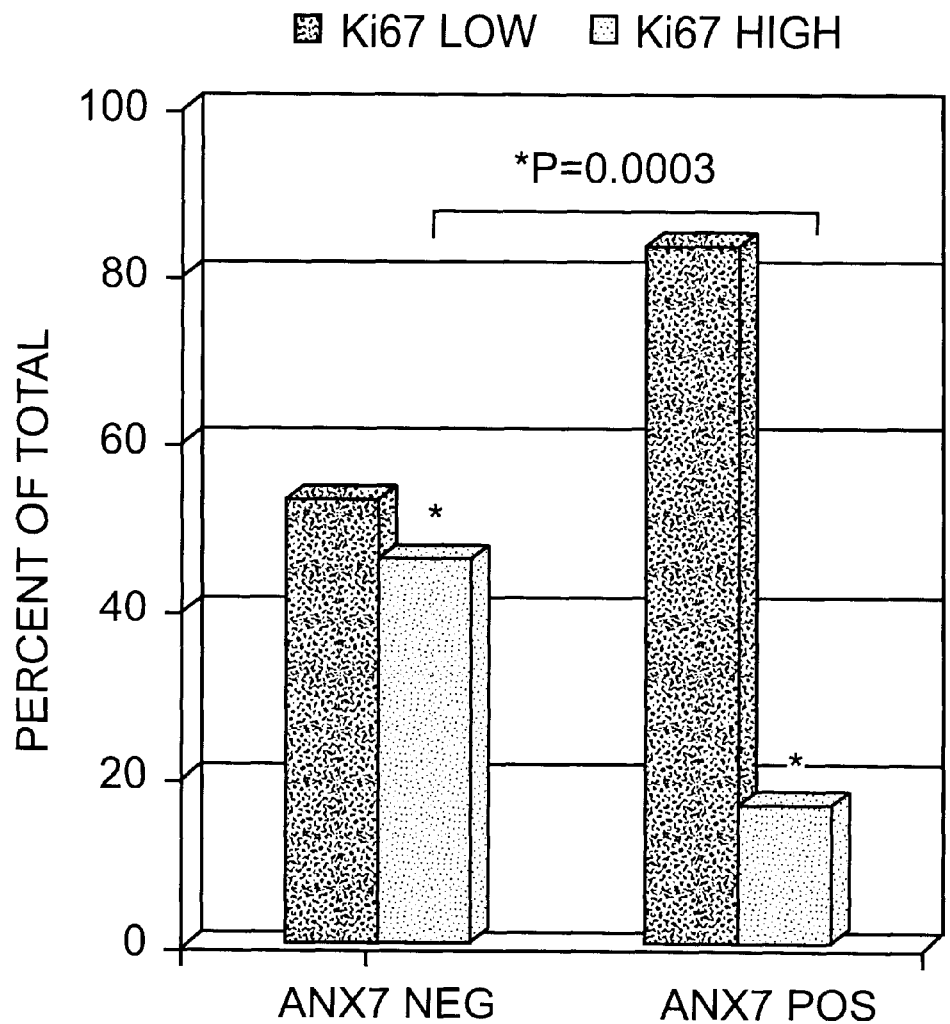
FIG. 17A depicts the immunostaining of human prostate cancer cells by Ki67 antibody.

Association Between Ki67 (Growth Fraction) and ANX7 Expression in Prostate Cancers Using Ki67 immunostaining as an index of tumor cell proliferation, we found a positive correlation between a high Ki67 labeling index and a lack of ANX7 expression, as well as a correlation with advanced stage prostate cancer and high Gleason score. As seen in FIG. 17A, ANX7 positive human prostate cancer cells have significantly fewer cells with high levels of immunostaining by Ki67 antibody (red bar), as compared to the percentage of cells with a low level of immunostaining (purple bar). In contrast, ANX7 negative human prostate cancer cells have a higher percentage of cells with high levels of immunostaining by Ki67 antibody (red bar). These data are based on the analysis of 301 tumors and are statistically significant (p=0.0003).

Figure 17B:
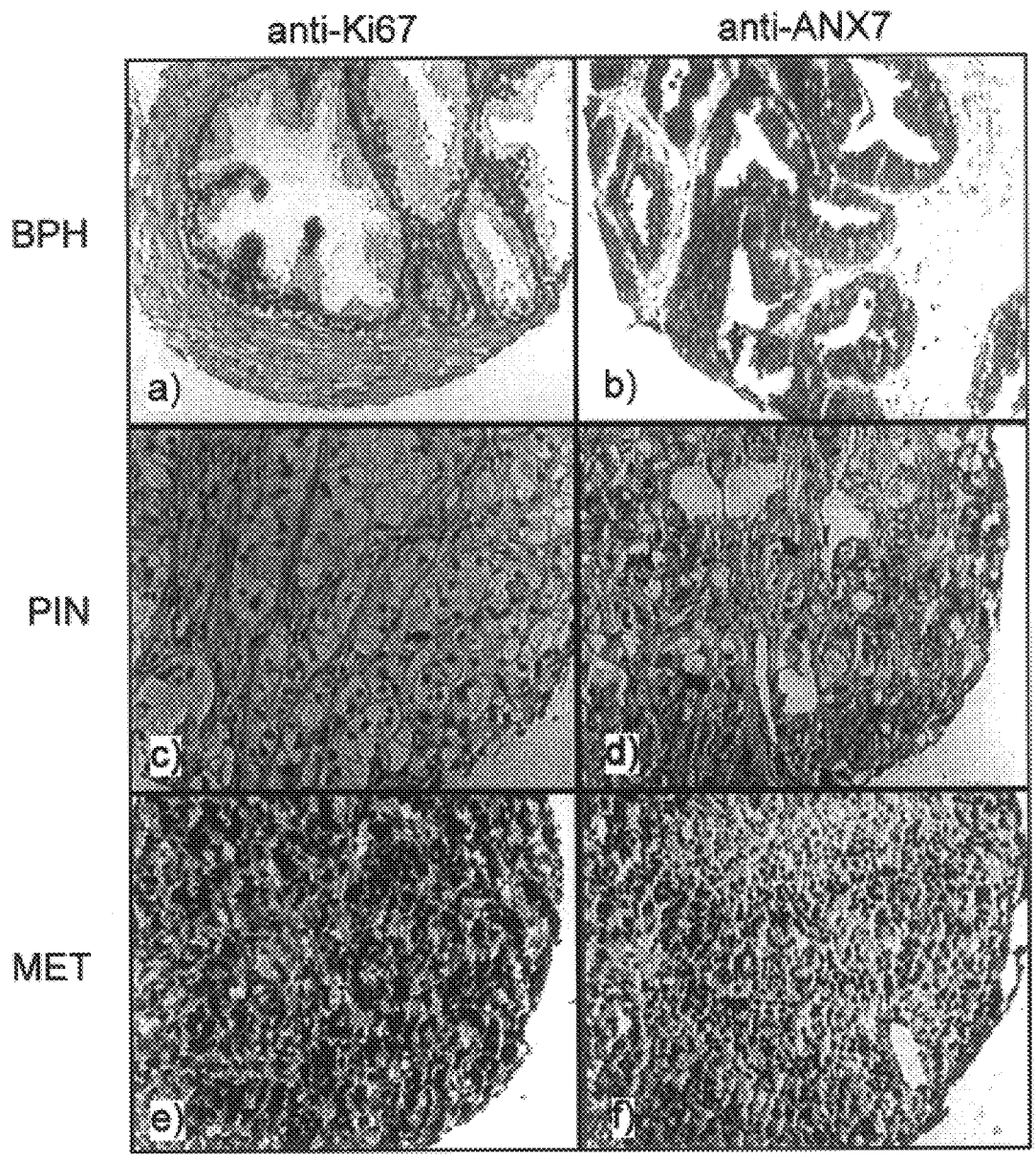
FIG. 17B depicts example histological images stained by antibody Ki67 (left column) or consecutive sections stained for ANX7 protein (right column). (BPH—benign prostatic hypertrophy; PIN—primary intraepithelial neoplasms; MET—metastatic prostate cancer.)
Figure 18:
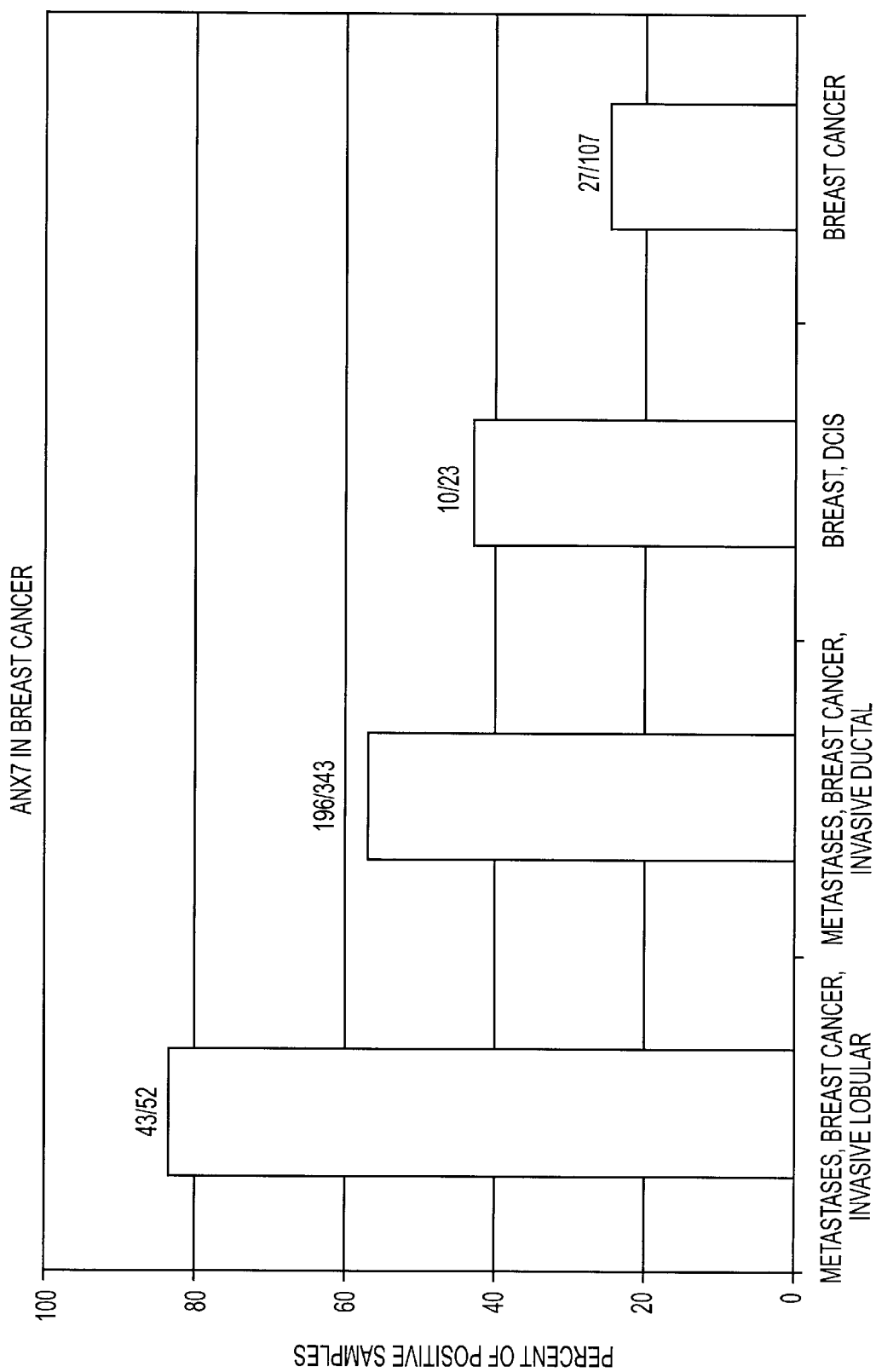
FIG. 18 depicts data from a breast cancer tissue microarray; normal breast tissue expresses virtually no ANX7 (see FIG. 26). The percent of samples that are positive for ANX7 become progressively greater as the diagnostic category gets "worse". Fractions are number of cases that are positive/total cases in this diagnostic category. Abbreviations: dcis (ductal carcinoma in situ).

FIG. 17B shows example histological images taken from the samples used in FIG. 17A. The samples in the left column were stained by Ki67, which is indicative of the proliferative state. The samples in the right column are consecutive sections stained for ANX7 protein. Samples exhibiting benign prostatic hypertrophy (BPH) and primary intraepithelial neoplasms (PIN) were low in Ki67, but high in ANX7 protein. In contrast, samples exhibiting metastatic prostate cancer (MET) had high levels of Ki67, but virtually no ANX7 staining.

EXAMPLE XIII

Levels of ANX7 Protein Expression in Human Breast Cancer Tissue Micrarrays

Figure 19:
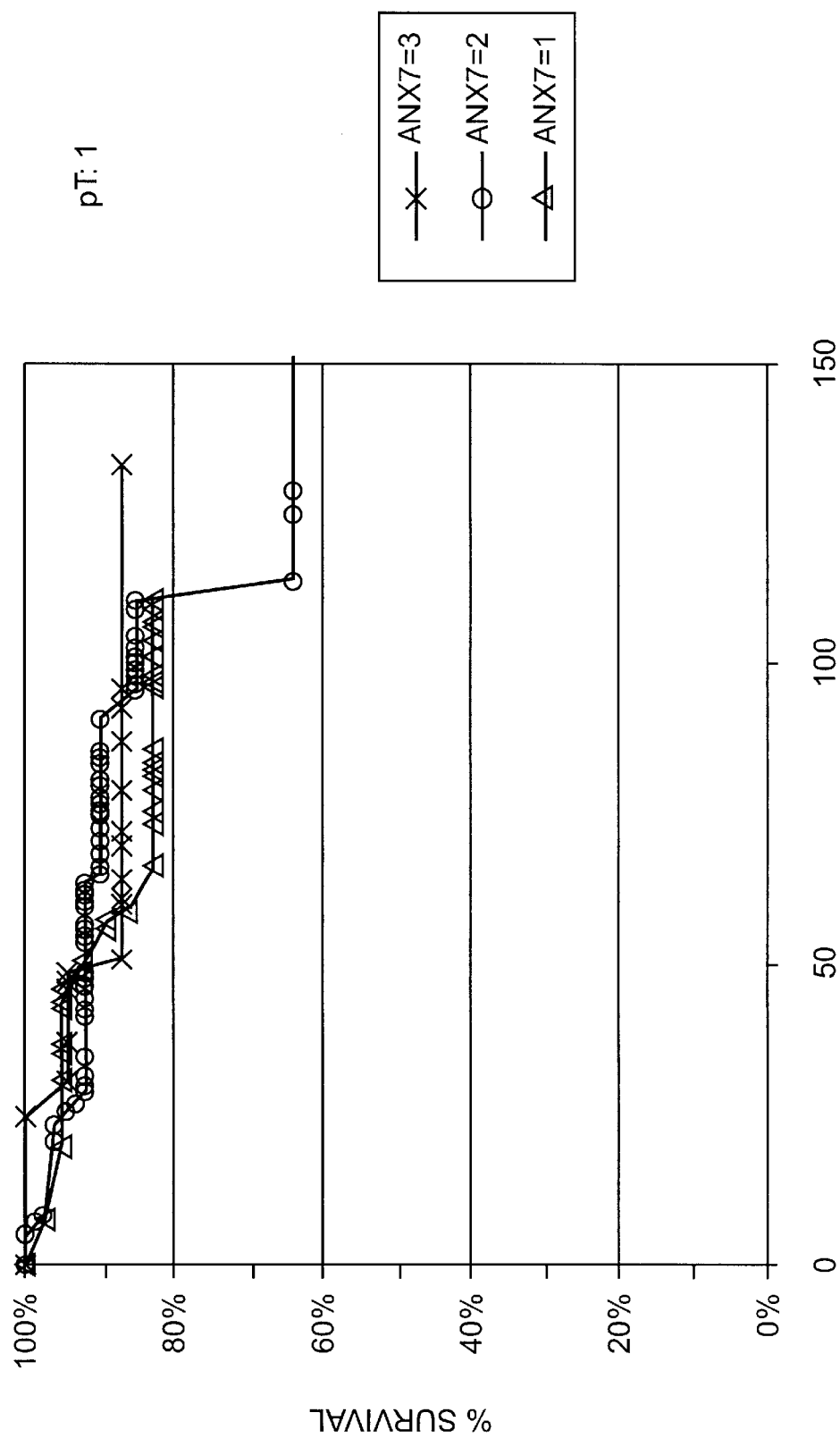
FIG. 19. Survival curves for patients in the pathological stage pT:1. ANX7=3, 2, and 1 are descending relative expression levels of ANX7 protein. Relative expression is assessed in terms of percent positive cells in the sample. Samples were taken for analysis at time=0. Note that for pT:1, ANX7 levels do not seem to affect or be affected by survival.
Figure 20:
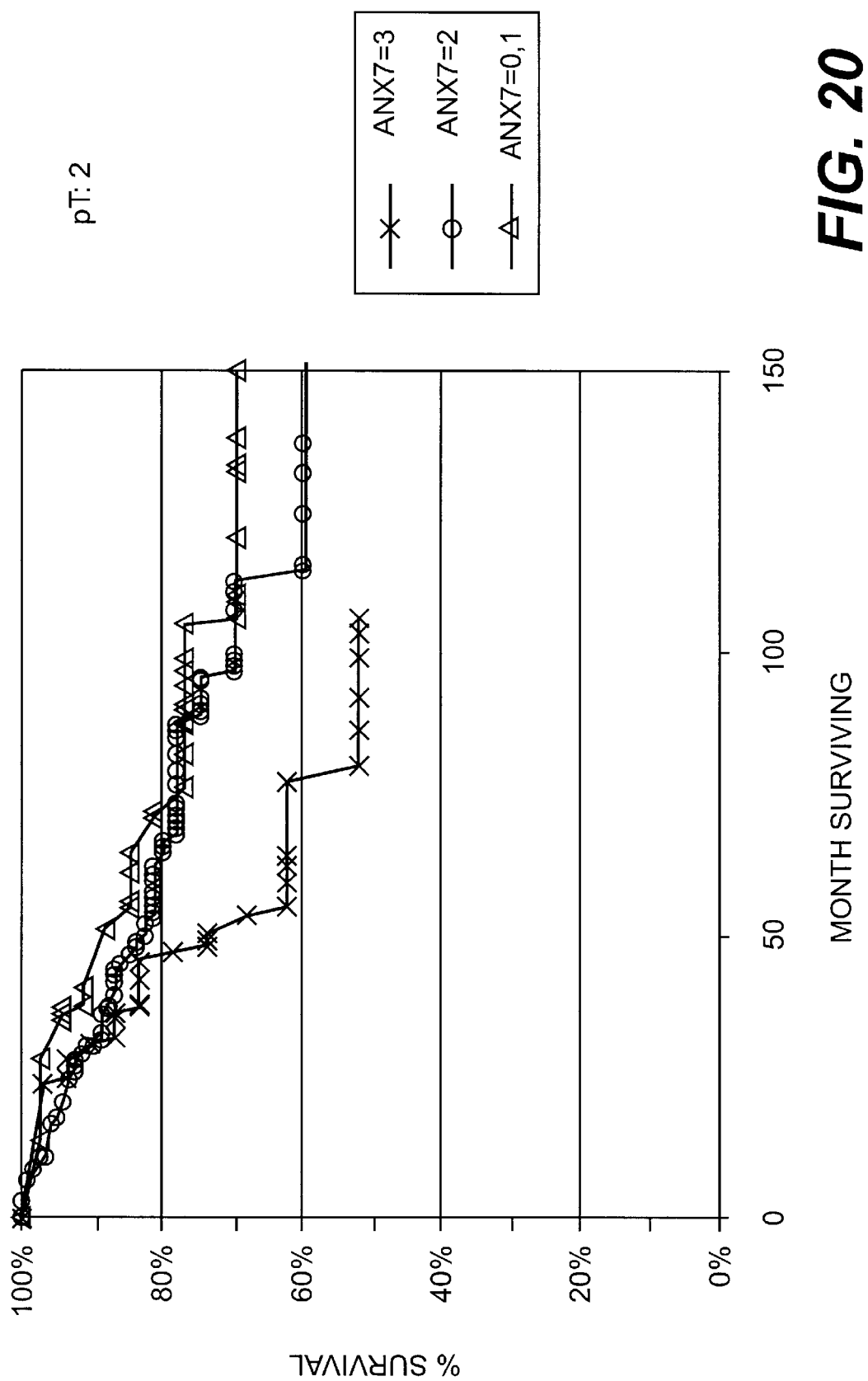
FIG. 20. Survival curves for patients in the pathological stage pT:2. ANX7=3, 2 and 1,0 are descending relative expression levels of ANX7 protein. Relative expression is assessed in terms of percent positive cells in the sample. Samples were taken for analysis at time=0. Note that for this slightly worse pathological stage, survival seems to be less likely as ANX7 levels rise.
Figure 21:
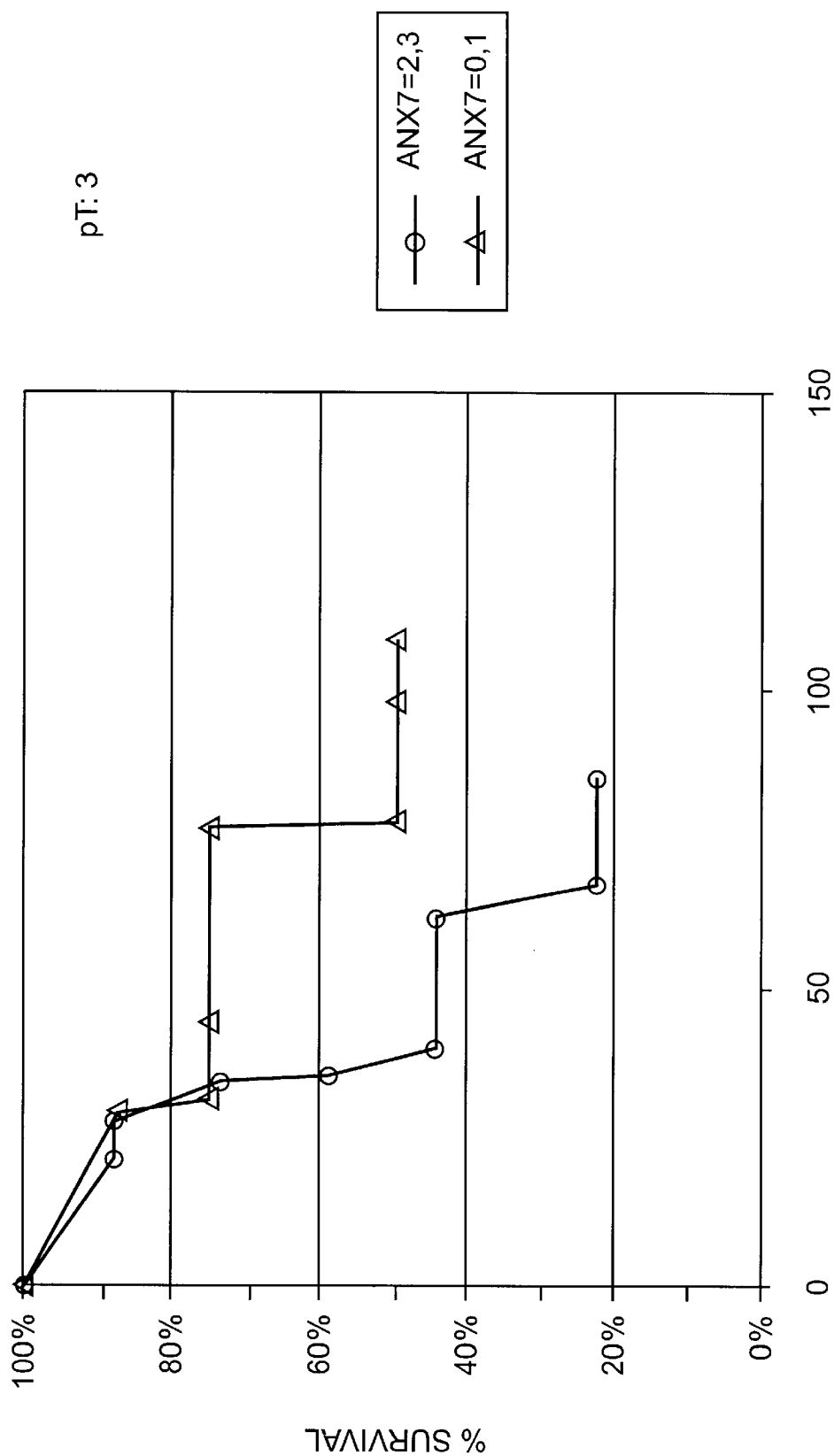
FIG. 21. Survival curves for patients in the pathological stage pT:3. ANX7=3, 2 and 1,0 are descending relative expression levels of ANX7 protein. Relative expression is assessed in terms of percent positive cells in the sample. Samples were taken for analysis at time=0. Note that for this even worse pathological stage, survival is less likely with higher ANX7 levels.
Figure 22:
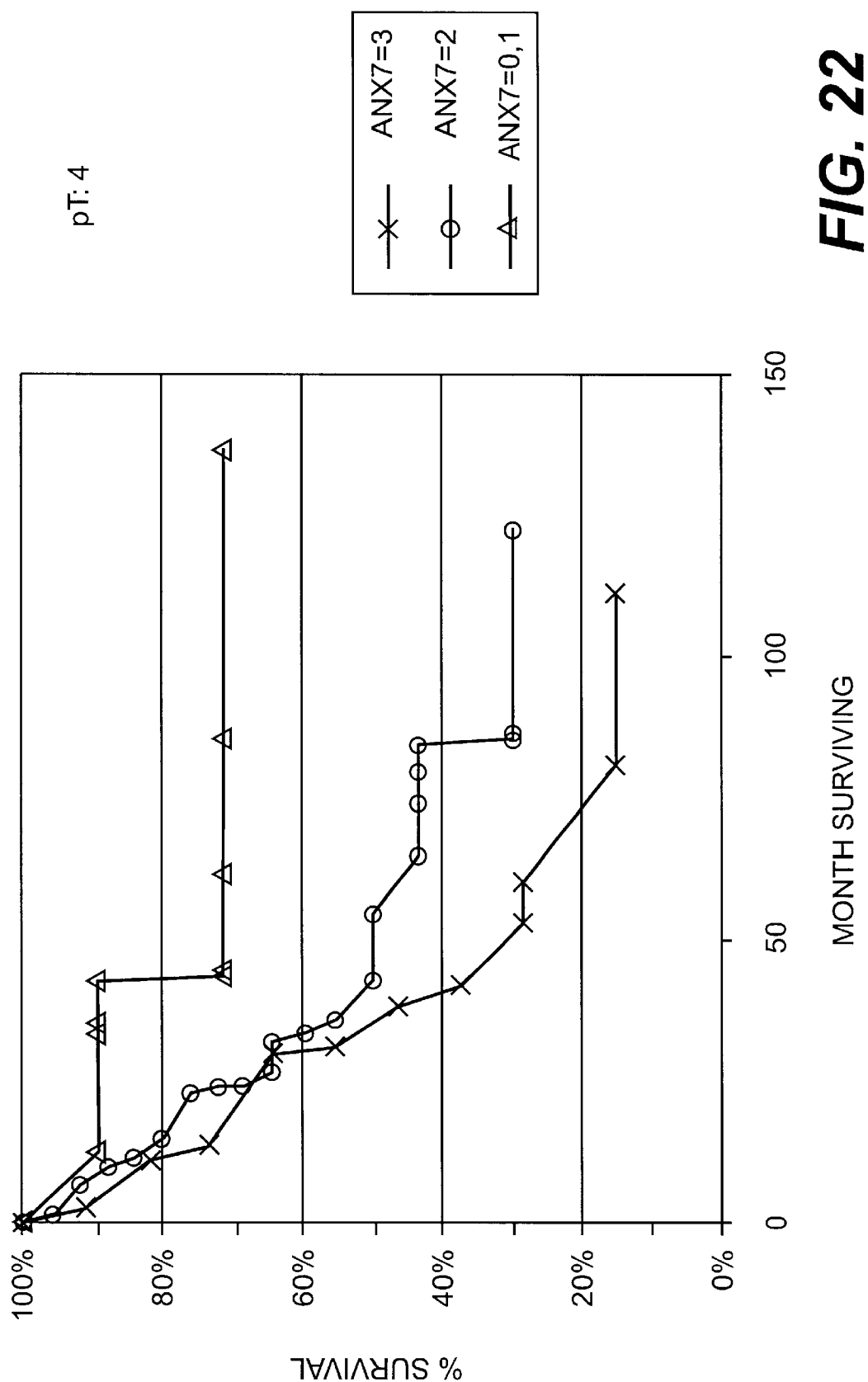
FIG. 22. Survival curves for patients in the pathological stage pT:4. ANX7=3, 2 and 1,0 are descending relative expression levels of ANX7 protein. Relative expression is assessed in terms of percent positive cells in the sample. Samples were taken for analysis at time=0. Note that for this even worse pathological stage, survival is less likely with higher ANX7 levels. The values for separate ANX7 levels are more clearly delineated for the different levels of ANX7.
Figure 23:
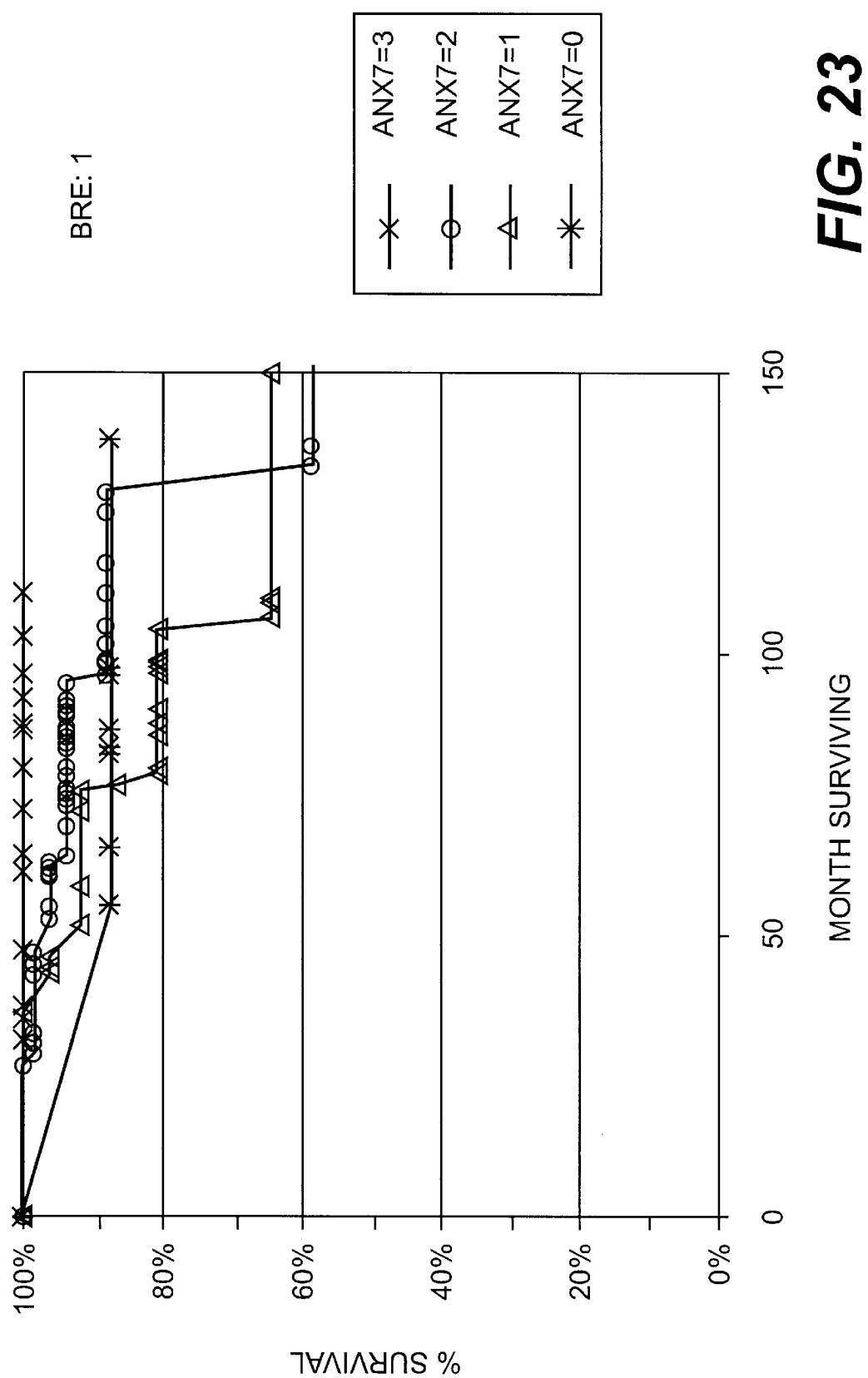
FIG. 23. Survival curves for patients in the clinical stage BRE:1. ANX7=3, 2 and 1 are descending relative expression levels of ANX7 protein. Relative expression is assessed in terms of percent positive cells in the sample. Samples were taken for analysis at time=0. At this mild stage, the survival frequency is not apparently affected by the level of ANX7 protein.
Figure 24:
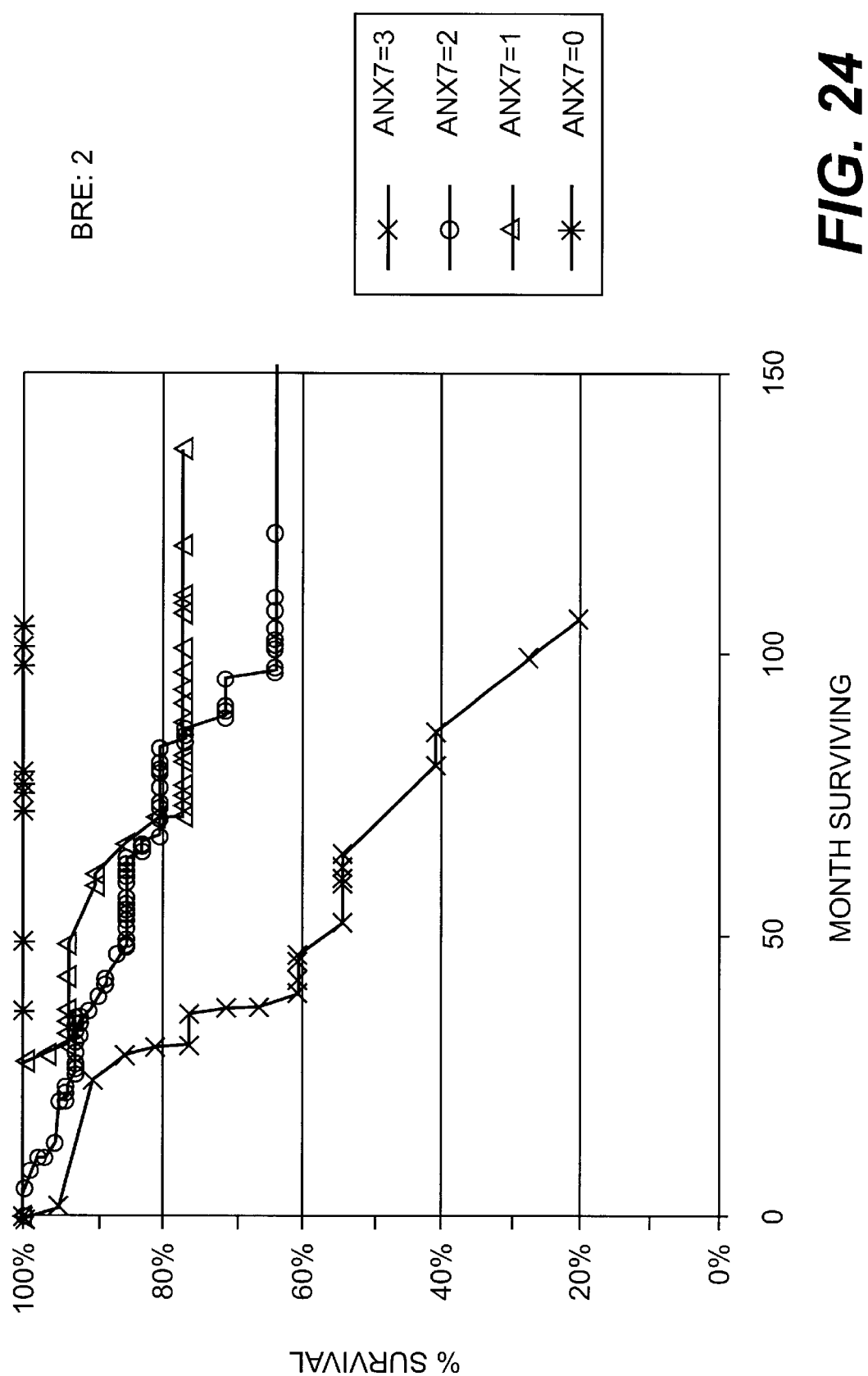
FIG. 24. Survival curves for patients in the clinical stage BRE:2. ANX7=3, 2 and 1 are descending relative expression levels of ANX7 protein. Relative expression is assessed in terms of percent positive cells in the sample. Samples were taken for analysis at time=0. At this more aggressive stage, the survival frequency is profoundly affected by the highest level of ANX7 protein, ANX7=3.
Figure 25:
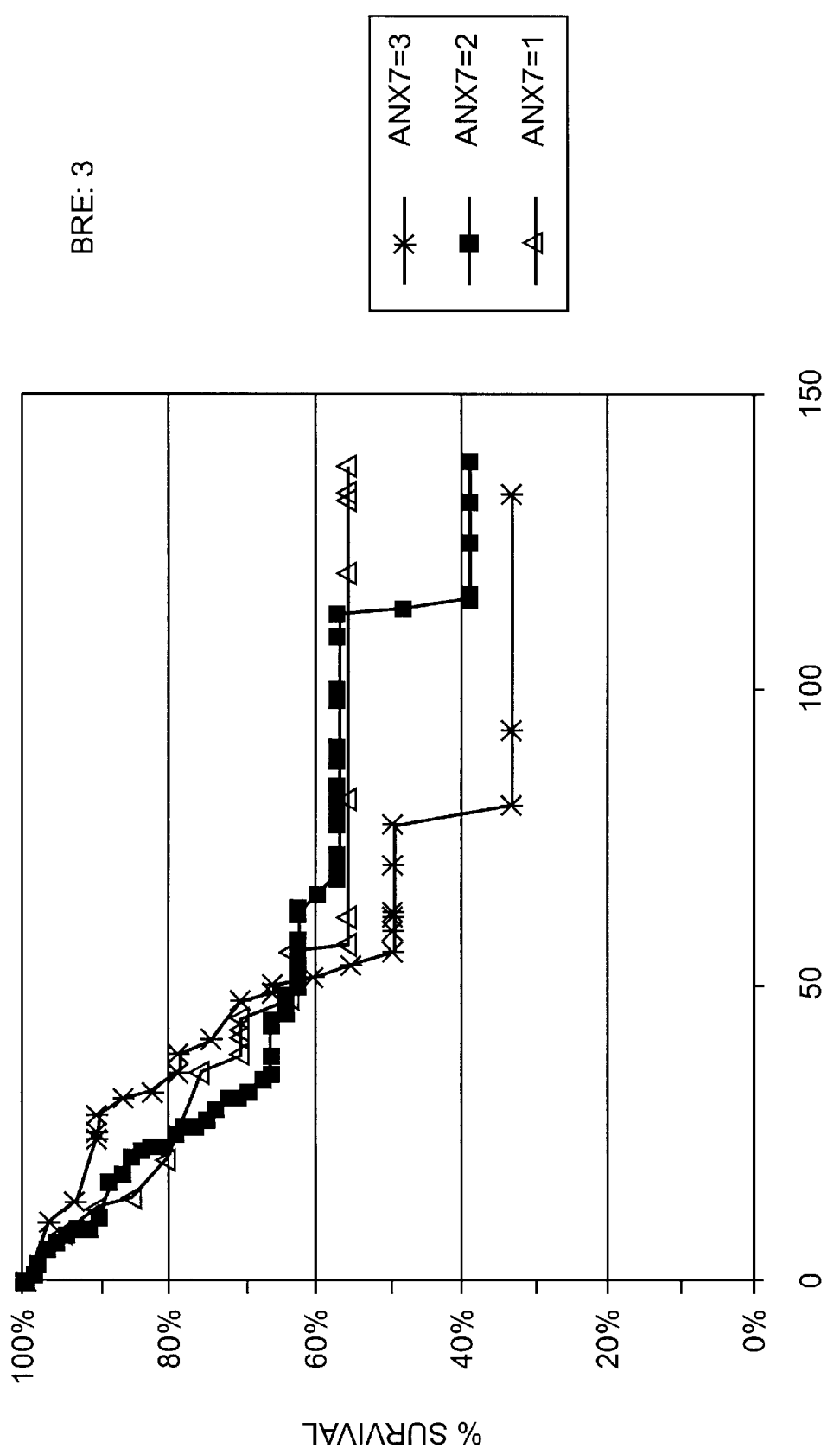
FIG. 25. Survival curves for patients in the clinical stage BRE:3. ANX7=3, 2 and 1 are descending relative expression levels of ANX7 protein. Relative expression is assessed in terms of percent positive cells in the sample. Samples were taken for analysis at time=0. At this even more aggressive stage, the survival frequency is profoundly affected by the highest level of ANX7 protein, ANX7=3. However, the general level of survival is not good in general.
Figure 26A:
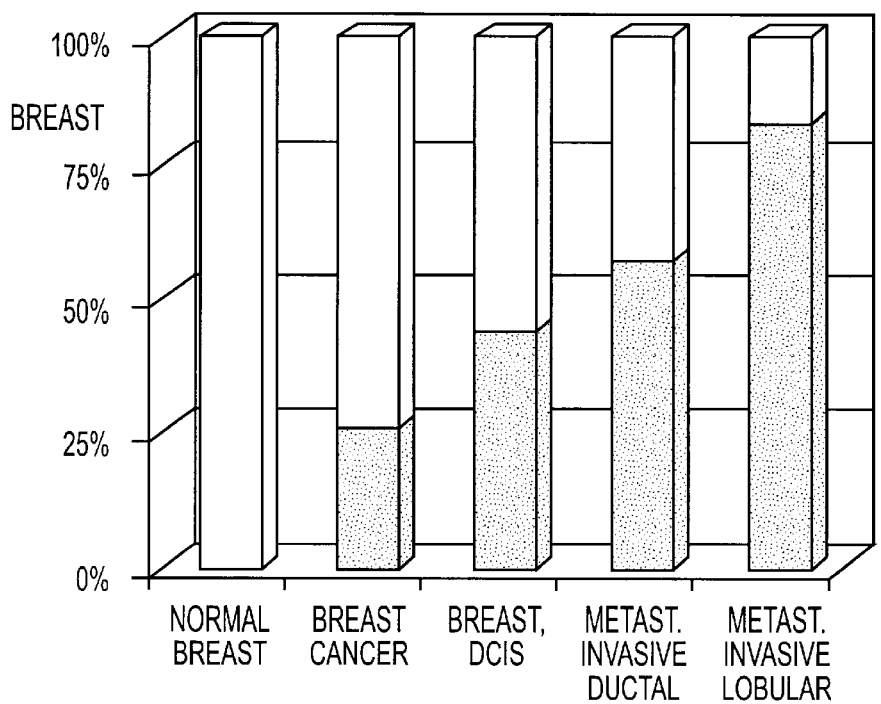
FIG. 26. Tumor types in which the normal tissue is low in ANX7, and where some of the tumors tend to be higher. Data are given as percent of tumor cells positive for ANX7 protein. Upper left panel: Breast cancer; see FIG. 18 for these data without control. Upper right panel: Sarcoma's. Lower left panel: lung cancer; note that normal adult lung is virtually deficient in ANX7, while fetal lung is 25% positive. Carcinoid, small, and large cell lung cancers are profoundly distinct from ANX7 levels found in normal tissue. Lower right panel: testes; ledig tumor seems to be the most distinct from normal tissue.
Figure 26B:
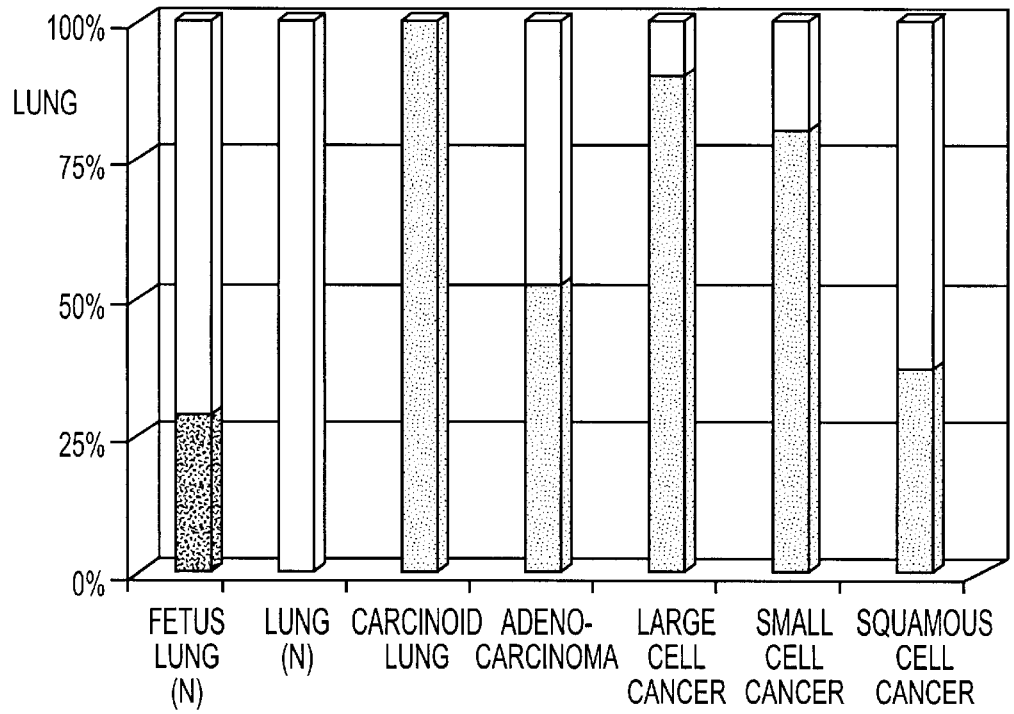
Figure 26C:
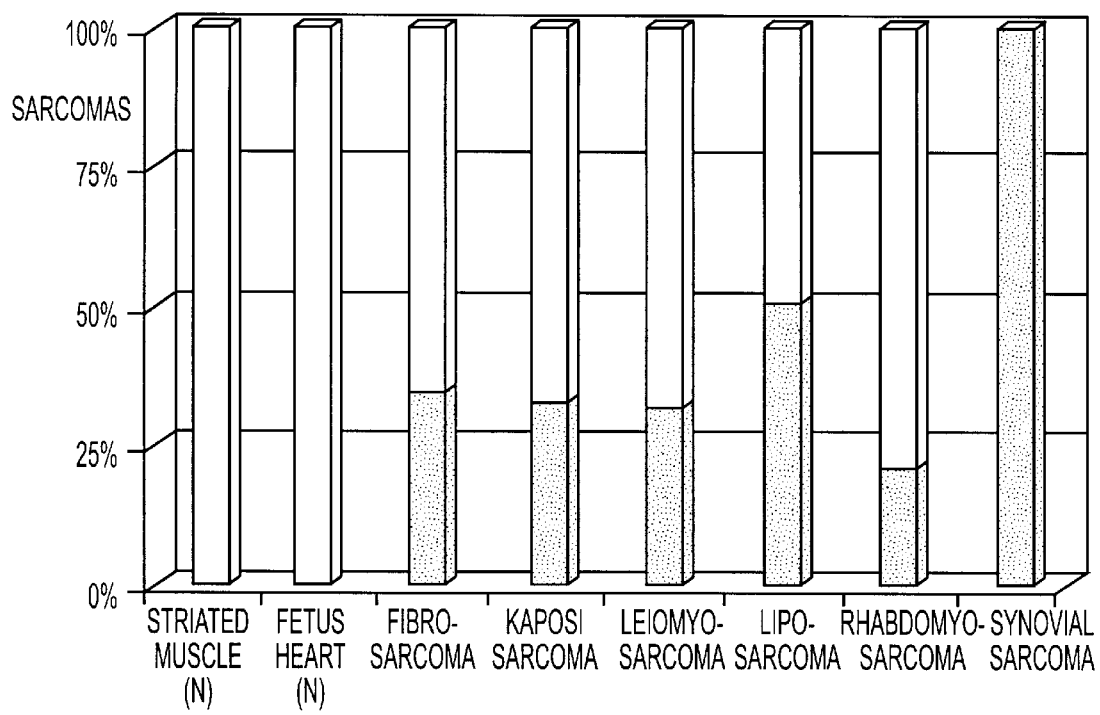
Figure 26D:
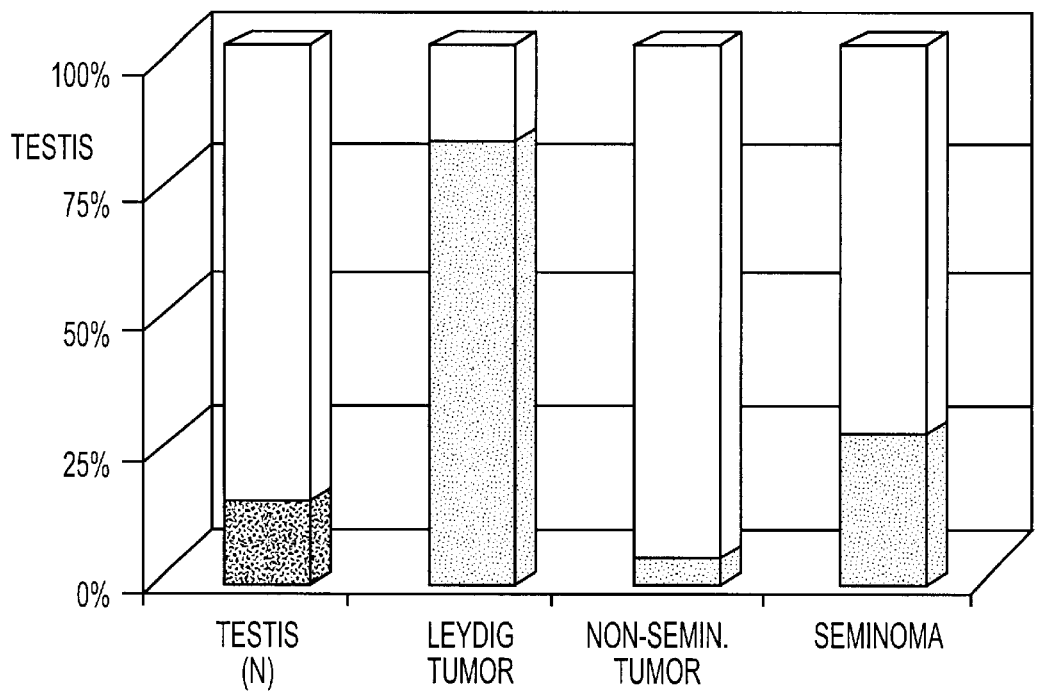
Figure 27A:
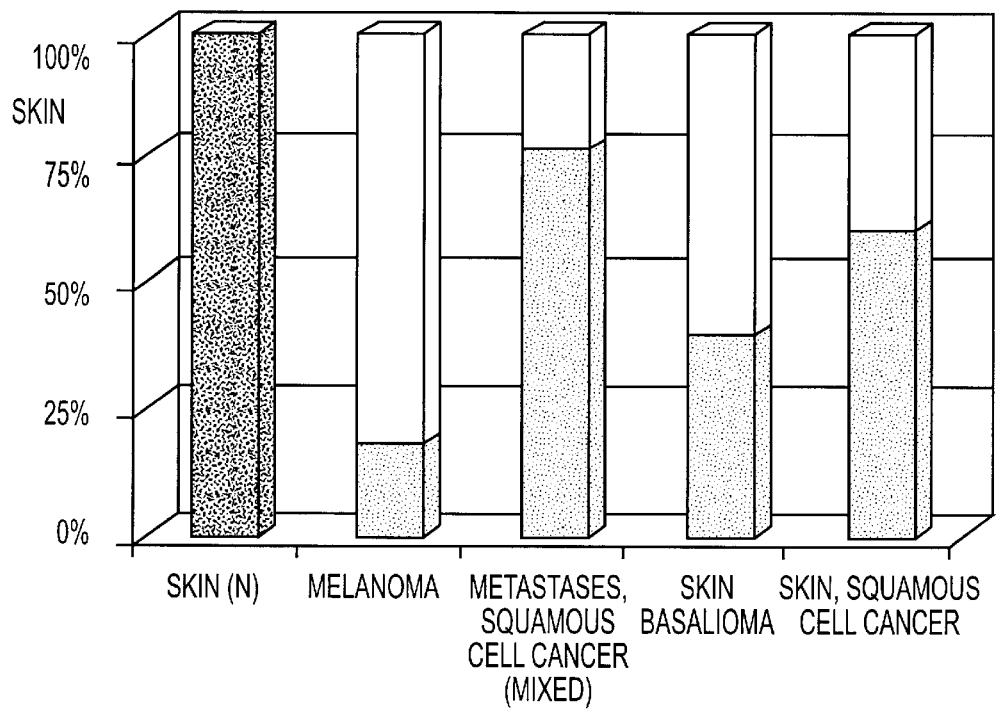
FIG. 27. Tumor types in which the normal tissue is high in ANX7, and where some of the tumors tend to be low. Upper left panel: skin; melanomas appear to be the most distinct. Upper right panel: lymphoid tissue; the three types of tumors studied appear to be distinct from normal lymph node tissue. Lower left panel: prostate; see earlier parts of this description for detailed studies on the prostate. Lower right panel: nerve. Another type of tumor with as aspect of this pattern of behavior is gynecological (see FIG. 28).
Figure 27B:
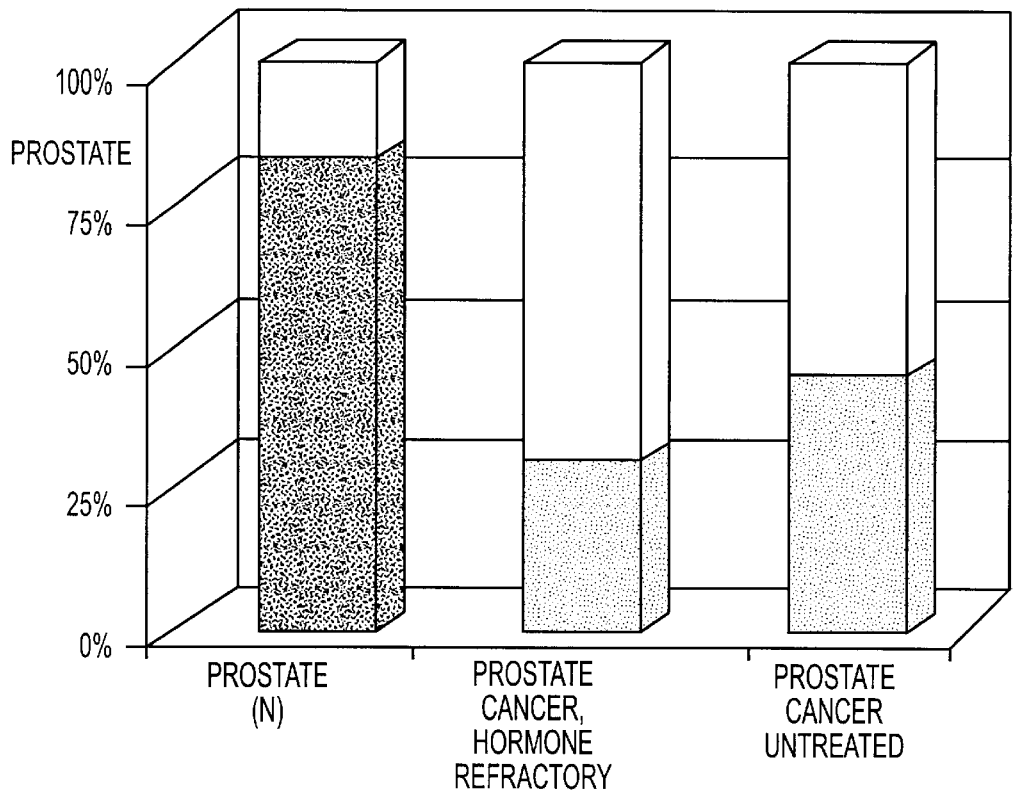
Figure 27C:
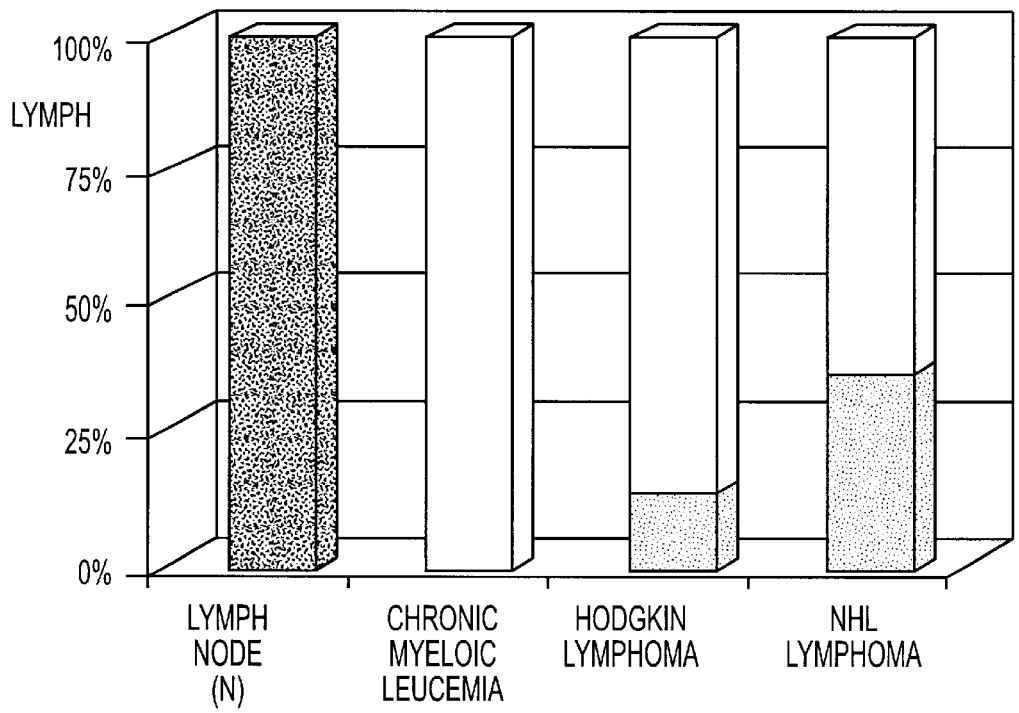
Figure 27D:
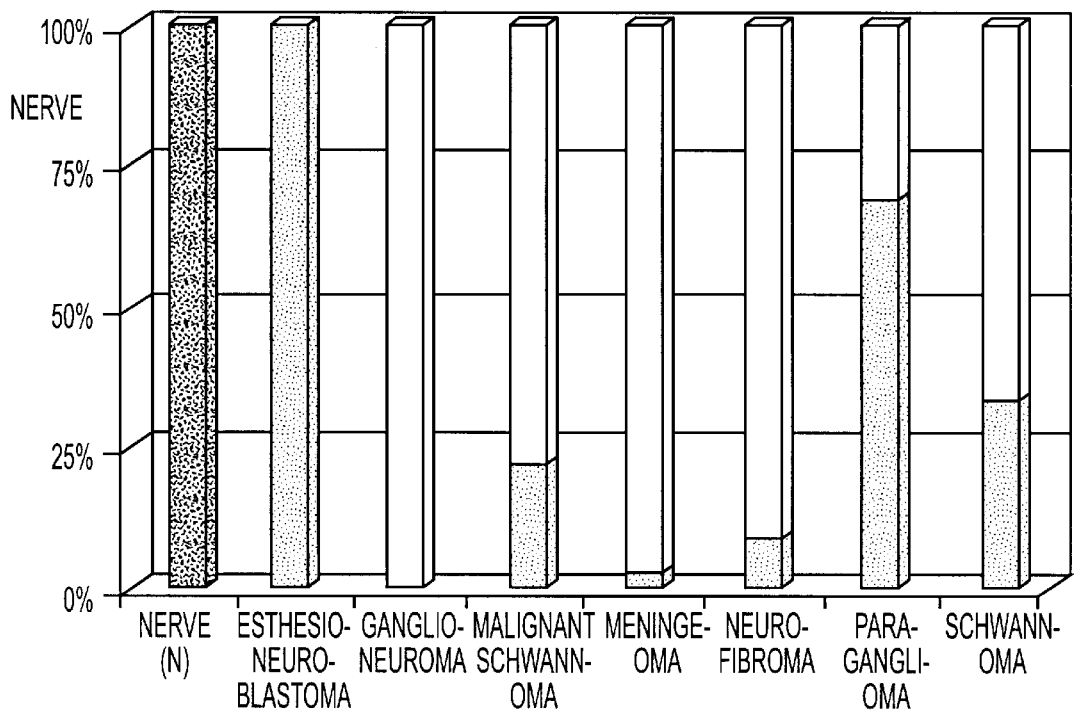
Figure 28A:
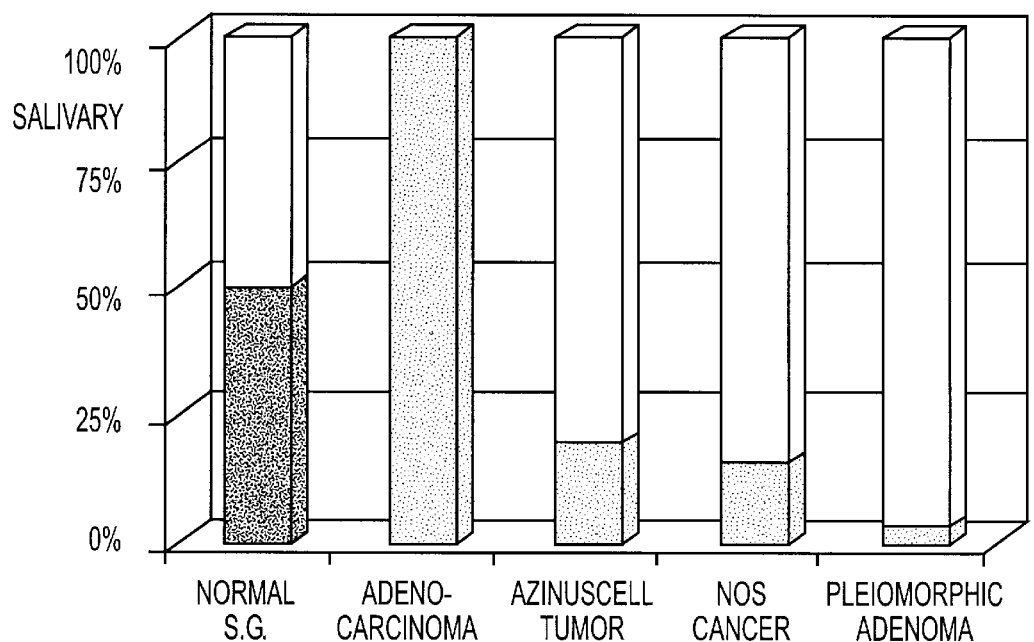
FIG. 28. Tumor types in which the normal levels of ANX7 protein can be ca. 50%, and where tumors also vary in the same range. Upper left panel: salivary gland tumors; note that adenocarcinoma is completely positive. Upper right panel: renal. Lower left panel: gynecological; while the normal uterine cervix is completely positive, the normal placenta is intermediate. Lower right panel: thyroid.
Figure 28B:
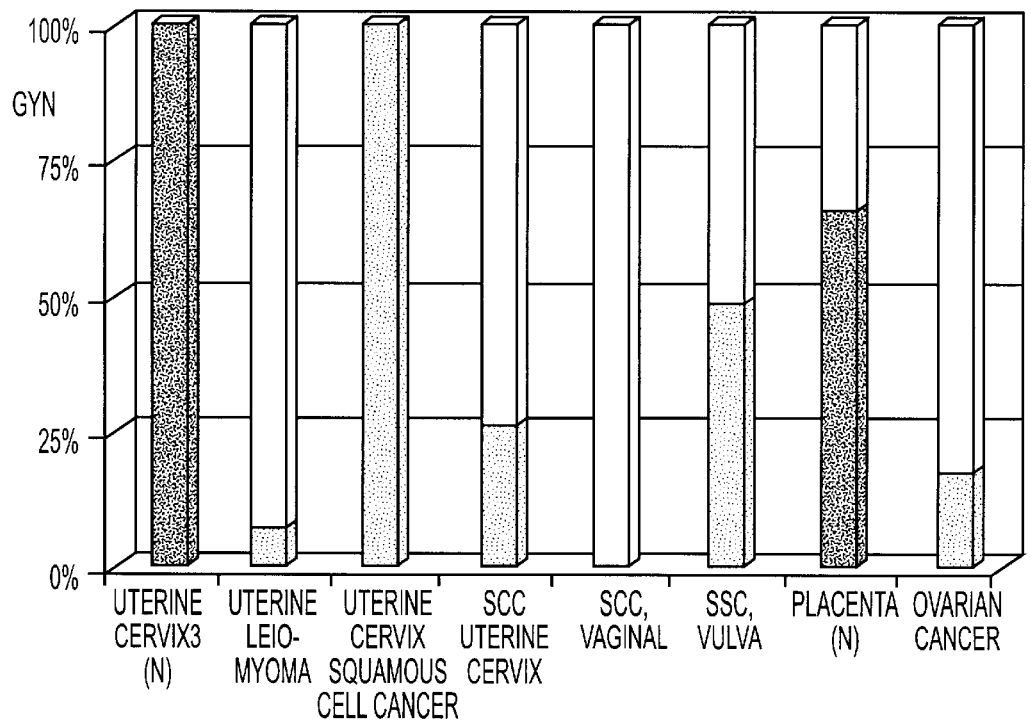
Figure 28C:
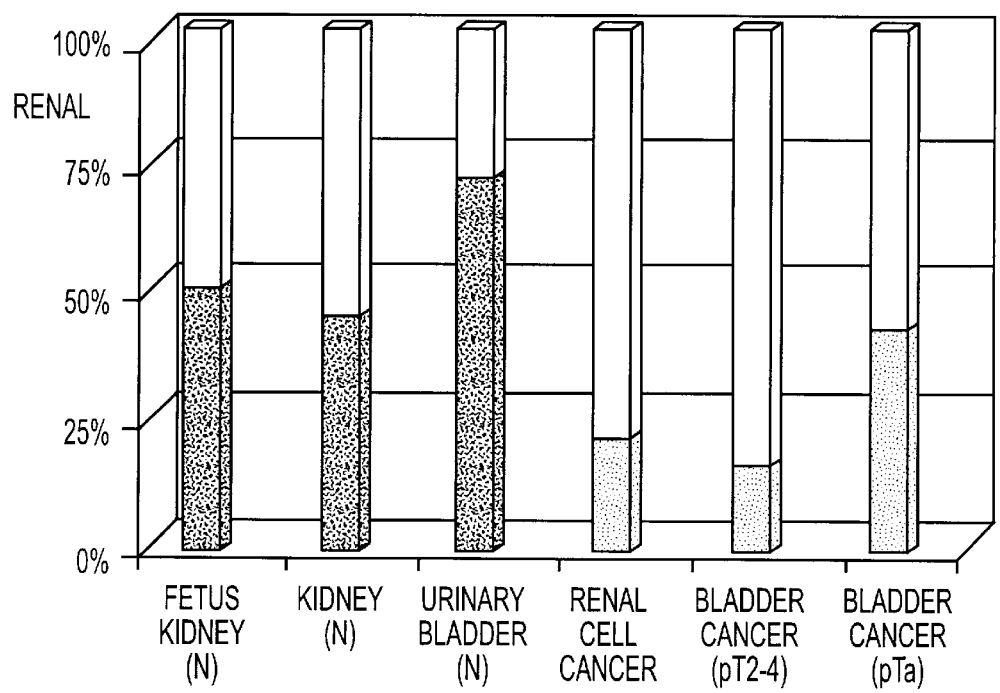
Figure 28D:
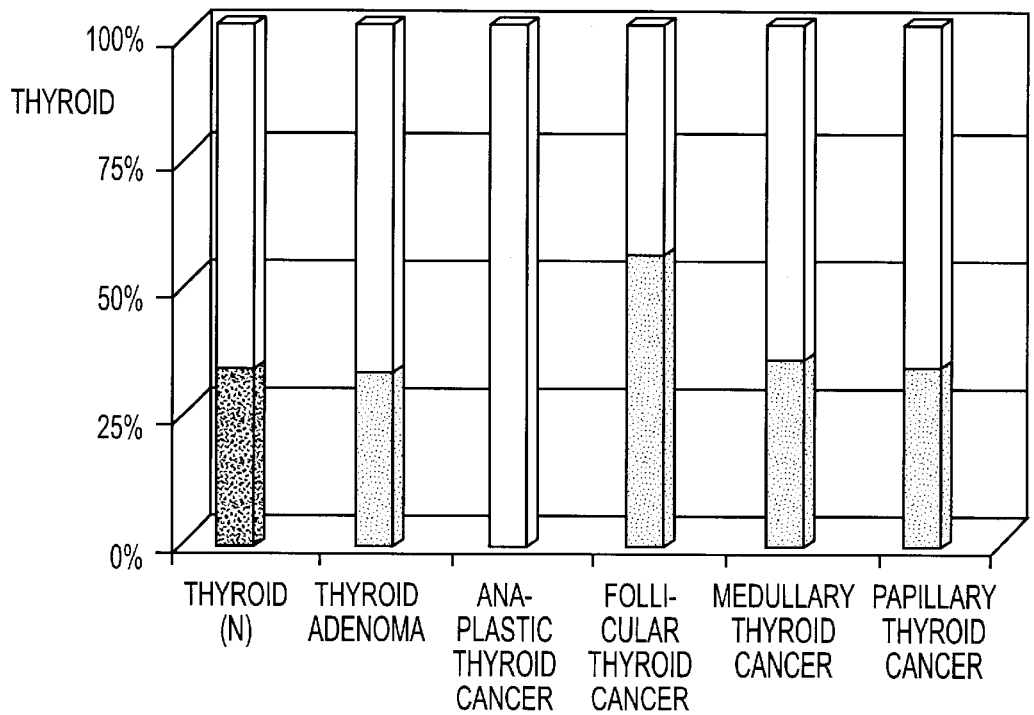
Figure 29:
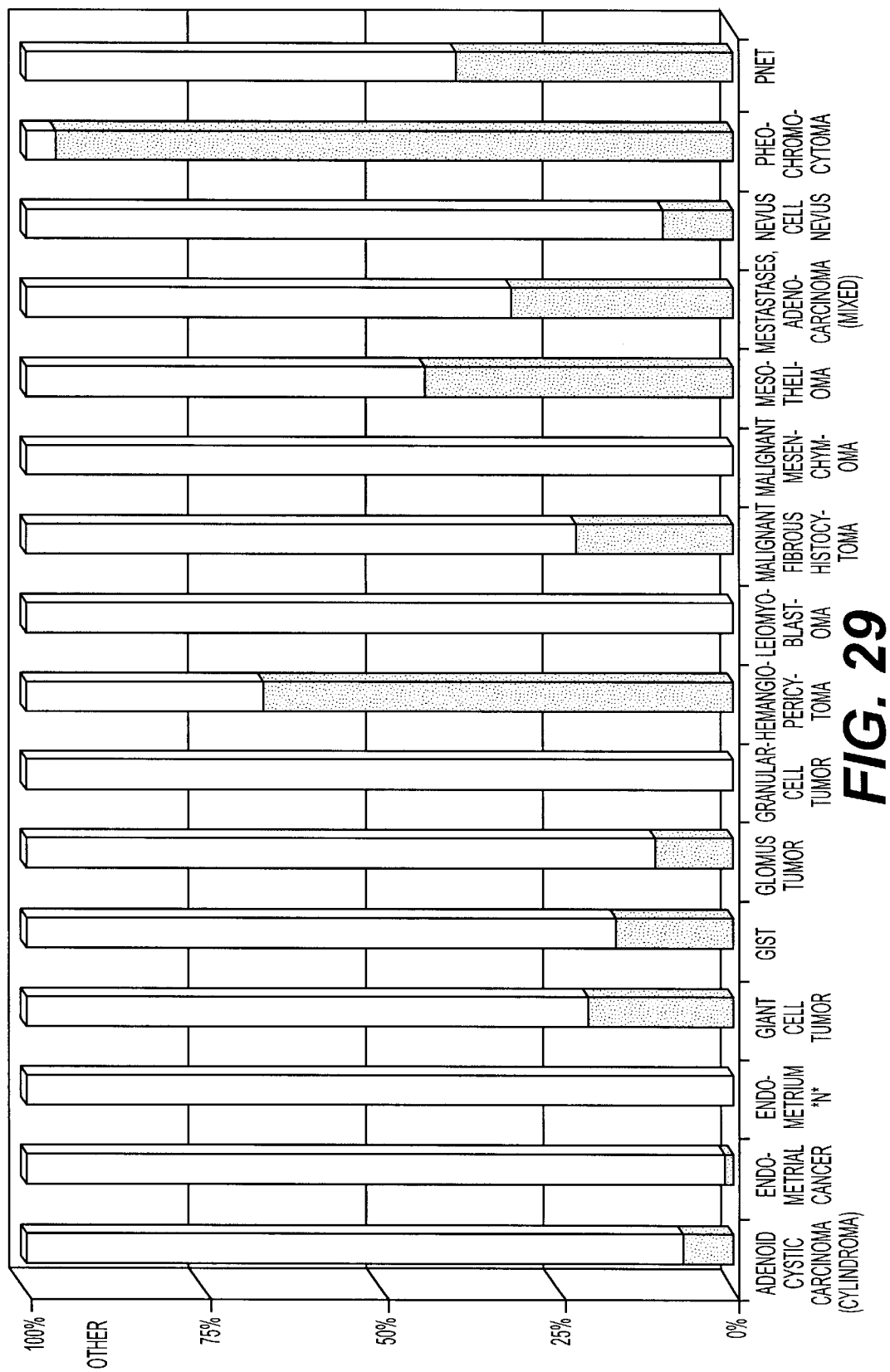
FIG. 29. Other tumors for which controls are not necessarily obvious.

Different normal tissues are characterized by either "high" or "low" levels of ANX7 gene expression. As seen above, in the case of prostate cancer, the normal prostate has high levels of ANX7, while metastatic and hormone insensitive local recurrences have very low levels of ANX7. By contrast, normal breast tissue has quite low levels (see FIG. 26), while cancerous forms have increasingly more ANX7 levels (see FIG. 19). We also show in FIGS. 19–25 that increasing levels of ANX7 protein expression in breast cancer strongly correlates with lower likelihood of survival.

EXAMPLE XIV

Levels of ANX7 Protein Expression in Other Tumor Types

We determined the level of ANX7 protein expression in a variety of other tumor types in which the normal tissue was found to have a low level of ANX7, as well as tumor types that tend to have higher levels. Data are given as percent of tumor cells positive for ANX7 protein. These tumor types include sarcoma, lung cancer, and testes, and the results are depicted in FIG. 26. Normal adult lung was found to be virtually deficient in ANX7, while fetal lung was 25% positive. Carcinoid, small and large cell lung cancers are profoundly distinct from normal tissue ANX7 levels.

For the tumor types depicted in FIG. 27, normal tissue gave high levels of ANX7, but some of the tumors tend to have low levels. The tissues represented in FIG. 27 include skin, lymphoid tissue, prostate (see earlier parts of this description for detailed studies on the prostate), and nerve tissue.

In FIG. 28, we found that the tumor types had normal levels of ANX7 protein of ca. 50%. These included salivary gland tumors (adenocarcinoma is completely positive), renal, gynecological, and thyroid.

Figure 30:
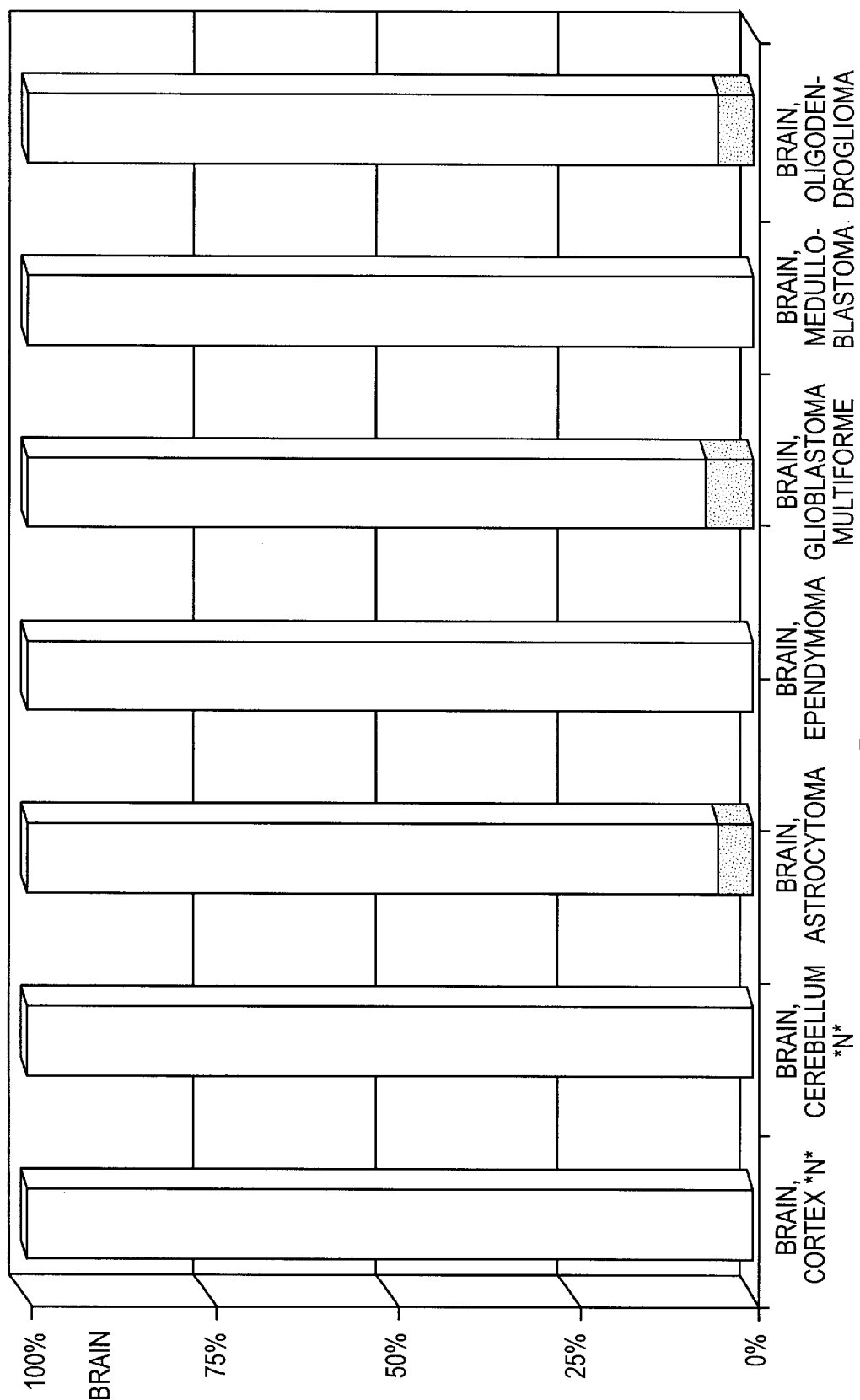
FIG. 30. Brain; levels of ANX7 are generally low in this tissue, and in derived tumors.

Brain tissue had generally low levels of ANX7, as did derived tumors from this tissue. (See FIG. 30).

Figure 31:
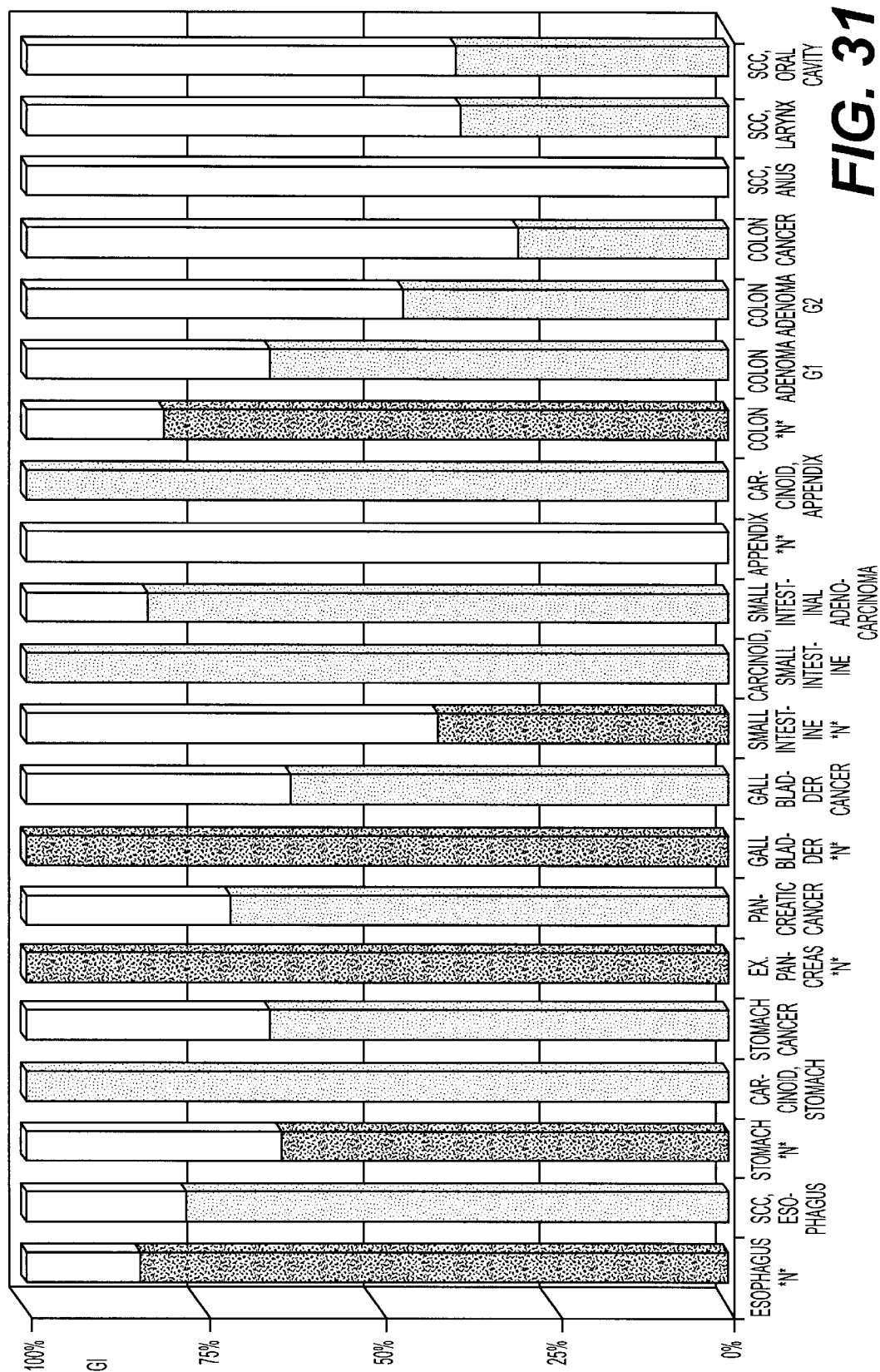
FIG. 31. GI tumors vary in level of ANX7. Normal exocrine pancreas is 100% positive, while normal colon is in the range of 80%. Note that for the progression of colon adenoma G1 (grade 1), colon adenoma G2 (grade 2), and colon cancer, there is the appearance of a steady downward projection in ANX7 positive cells.

GI tumors vary in level of ANX7 (See FIG. 31.) Normal exocrine pancreas is 100% positive, while normal colon is in the range of 80%. Note that for the progression of colon adenoma GI (grade 1), colon adenoma G2 (grade 2), and colon cancer, there is the appearance of a steady downward projection in ANX7 positive cells.

Figure 32:
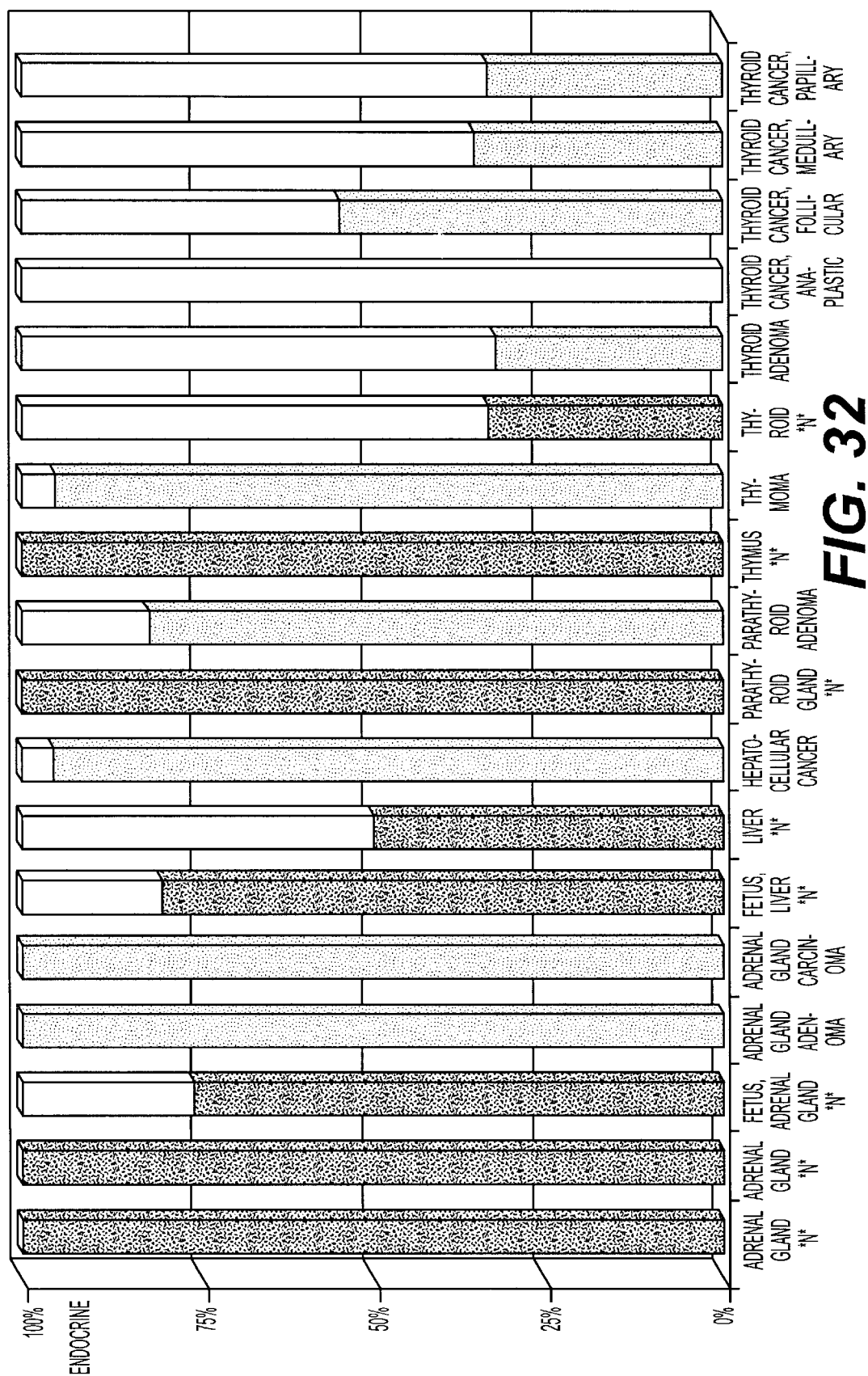
FIG. 32. Endocrine tumors for which normal tissue is available for comparison, but where variation by the tumors is not dramatic. Normal endocrine tissues tend to be high in ANX7 protein.

Variation in endocrine tumors is not dramatic. Normal endocrine tissues tend to be high in ANX7 protein. (See FIG. 32.)

The specification is most thoroughly understood in light of the teachings of the references cited within the specification which are hereby incorporated by reference. The embodiments within the specification provide an illustration of embodiments of the invention and should not be construed to limit the scope of the invention. The skilled artisan readily recognizes that many other embodiments are encompassed by the invention.

We claim:

1. A transgenic mouse having cells comprising a chromosomally incorporated transgene that comprises a detectable marker sequence, wherein one allele of a genomic Anx VII gene is functionally disrupted by said transgene, wherein said transgenic mouse exhibits an increased susceptibility to formation of tumors as compared to a wild type mouse, and wherein said tumors are one or more of insulinoma, hepatocellular carcinoma, and lymphoma of the thymus.

2. The transgenic mouse of claim 1, wherein all cells of the mouse comprise said chromosomally incorporated transgene.

3. The transgenic mouse of claim 2, wherein the mouse is formed by crossing a mouse according to claim 1 with a second mouse.

4. The transgenic mouse of claim 1, wherein the tumors are lymphosarcoma of the thymus.

5. The transgenic mouse of claim 1, wherein the tumors are insulinoma.

6. The transgenic mouse of claim 1, wherein the tumors are hepatocellular carcinoma.

7. A transgenic mouse embryo having cells comprising a chromosomally incorporated transgene that comprises a detectable marker sequence, wherein at least one allele of the Anx VII gene is functionally disrupted by said transgene, and wherein said mouse embryo is aged E10 or less.

8. A method for generating a transgenic mouse having an endogenous Anx VII gene that is functionally disrupted, comprising the steps of:
   a) constructing a transgene construct containing
      (i) a recombination region having all or a portion of the endogenous Anx VII gene, and
      (ii) a marker sequence, which provides a detectable signal for identifying the presence of the transgene in a cell;
   b) transferring the transgene into embryonic stem cells of a mouse by the process of homologous recombination;
   c) selecting embryonic stem cells having a correctly targeted homologous recombination between the transgene construct and the Anx VII gene;
   d) transferring the cells of step (c) into a blastocyst and implanting the resulting chimeric blastocyst into a female mouse; and
   e) selecting offspring harboring an endogenous Anx VII gene allele comprising the correctly targeted recombination.

9. A method for generating an isolated transgenic mouse embryonic stem cell having an endogenous Anx VII gene that is functionally disrupted, comprising the steps of:
   a) constructing a transgene construct containing
      (i) a recombination region having all or a portion of the endogenous Anx VII gene, and
      (ii) a marker sequence which provides a detectable signal for identifying the presence of the transgene in a cell;
   b) transferring the transgene into an embryonic stem cell of a mouse by the process of homologous recombination; and
   c), selecting a mouse embryonic stem cell having a correctly targeted homologous recombination between the transgene construct and the endogenous Anx VII gene.

10. A method for evaluating the carcinogenic potential of an agent, comprising the steps of:
   a) contacting the transgenic mouse of claim 1 with a test agent, and
   b) comparing the number of transformed cells in a sample of the treated transgenic mouse with the number of transformed cells in a sample from an untreated transgenic mouse or a transgenic mouse treated with a control agent, wherein the difference in the number of transformed cells in the treated mouse, relative to the number of transformed cells in the absence of treatment or in the presence of a control agent, indicates the carcinogenic potential of the test agent.

11. A method of testing a substance for efficacy in the treatment of an Anx VII tumor suppressor disease, said method comprising exposing the mouse of claim 1 to a test agent, and determining the progression of said disease in said mouse, wherein an arrest, delay or reversal in said progression as compared to an untreated mouse indicates that said substance is useful for the treatment of said Anx VII tumor suppressor disease.

12. The method of claim 11, wherein the Anx VII tumor suppressor disease is one or more of insulinoma, hepatocellular carcinoma, and lymphoma of the thymus.

13. The method of claim 12, wherein the Anx VII tumor suppressor disease is insulinoma.

14. The method of claim 12, wherein the Anx VII tumor suppressor disease is hepatocellular carcinoma.

15. The method of claim 12, wherein the Anx VII tumor suppressor disease is lymphoma of the thymus.

16. A transgene construct comprising a recombination region having all or a portion of an endogenous Anx VII gene; wherein the Anx VII gene comprises an inserted marker sequence which provides a detectable signal for identifying the presence of the transgene in a mammalian cell; wherein the Anx VII gene is functionally disrupted.

17. An isolated mammalian cell containing the transgene construct of claim 16, wherein one allele of a genomic Anx VII gene is functionally disrupted by said transgene.

18. An isolated cell containing the transgene construct of claim 17, wherein one allele of a genomic Anx VII gene is functionally disrupted by said transgene.

19. An isolated cell obtained from the transgenic mouse embryo of claim 7.

* * * * *

UNITED STATES PATENT AND TRADEMARK OFFICE
CERTIFICATE OF CORRECTION

PATENT NO. : 6,747,187 B1  Page 1 of 1
APPLICATION NO. : 09/633278
DATED : June 8, 2004
INVENTOR(S) : Srivastava et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (128) days Delete the phrase "by 128 days" and insert -- by 174 days --

Signed and Sealed this

Fourteenth Day of October, 2008

JON W. DUDAS
*Director of the United States Patent and Trademark Office*